US008541002B2

(12) United States Patent
Truneh et al.

(10) Patent No.: US 8,541,002 B2
(45) Date of Patent: Sep. 24, 2013

(54) VACCINE FOR TREATMENT AND PREVENTION OF HERPES SIMPLEX VIRUS INFECTION

(75) Inventors: Alemseged Truneh, Sudbury, MA (US); Daniel L. Levey, Boston, MA (US); Xiaoyan Mo, Boxborough, MA (US); Kenneth P. Leclair, Needham, MA (US); Ramesh S. Kashi, Warren, NJ (US); Chuanliang Liu, King of Prussia, PA (US)

(73) Assignee: Agenus Inc., Lexington, MA (US)

( * ) Notice: Subject to any disclaimer, the term of this patent is extended or adjusted under 35 U.S.C. 154(b) by 1686 days.

(21) Appl. No.: 10/571,716

(22) PCT Filed: Sep. 13, 2004

(86) PCT No.: PCT/US2004/029908
§ 371 (c)(1),
(2), (4) Date: Feb. 6, 2007

(87) PCT Pub. No.: WO2005/028496
PCT Pub. Date: Mar. 31, 2005

(65) Prior Publication Data
US 2011/0059041 A1 Mar. 10, 2011

Related U.S. Application Data

(60) Provisional application No. 60/503,148, filed on Sep. 12, 2003.

(51) Int. Cl.
*A61K 39/385* (2006.01)
*A61K 38/02* (2006.01)
*A61K 39/245* (2006.01)

(52) U.S. Cl.
USPC ............... 424/196.11; 424/231.1; 424/278.1; 435/5

(58) Field of Classification Search
None
See application file for complete search history.

(56) References Cited

U.S. PATENT DOCUMENTS

| | | | |
|---|---|---|---|
| 4,618,578 A | 10/1986 | Burke et al. |
| 4,642,333 A | 2/1987 | Person |
| 4,690,915 A | 9/1987 | Rosenberg |
| 4,709,011 A | 11/1987 | Cohen et al. |
| 4,761,470 A | 8/1988 | Emini et al. |
| 4,762,708 A | 8/1988 | Cohen et al. |
| 4,818,694 A | 4/1989 | Watson et al. |
| 4,855,224 A | 8/1989 | Berman et al. |
| 4,912,040 A | 3/1990 | Kaufman et al. |
| 5,149,660 A | 9/1992 | Cohen et al. |
| 5,171,568 A | 12/1992 | Burke et al. |
| 5,188,964 A | 2/1993 | McGuire et al. |
| 5,232,833 A | 8/1993 | Sanders et al. |
| 5,244,792 A | 9/1993 | Burke et al. |
| 5,288,639 A | 2/1994 | Burnie et al. |
| 5,348,945 A | 9/1994 | Berberian et al. |
| 5,464,758 A | 11/1995 | Gossen et al. |
| 5,583,112 A | 12/1996 | Kensil et al. |
| 5,633,152 A | 5/1997 | McKnight |
| 5,648,079 A | 7/1997 | Burke et al. |
| 5,652,115 A | 7/1997 | Marks et al. |
| 5,652,122 A | 7/1997 | Frankel et al. |
| 5,670,617 A | 9/1997 | Frankel et al. |
| 5,674,980 A | 10/1997 | Frankel et al. |
| 5,714,152 A | 2/1998 | Burke et al. |
| 5,750,119 A | 5/1998 | Srivastava |
| 5,759,814 A | 6/1998 | Burke et al. |
| 5,795,579 A | 8/1998 | Burke et al. |
| 5,795,721 A | 8/1998 | Rabin et al. |
| 5,804,604 A | 9/1998 | Frankel et al. |
| 5,807,557 A | 9/1998 | Dubin |
| 5,814,618 A | 9/1998 | Bujard et al. |
| 5,830,464 A | 11/1998 | Srivastava |
| 5,837,251 A | 11/1998 | Srivastava |
| 5,837,261 A | 11/1998 | Inglis et al. |
| 5,851,533 A | 12/1998 | Berman et al. |
| 5,859,310 A | 1/1999 | Bujard et al. |
| 5,888,981 A | 3/1999 | Bujard et al. |
| 5,912,411 A | 6/1999 | Bujard et al. |
| 5,935,576 A | 8/1999 | Srivastava |
| 5,961,979 A | 10/1999 | Srivastava |
| 5,985,270 A | 11/1999 | Srivastava |
| 5,997,873 A | 12/1999 | Srivastava |
| 6,004,941 A | 12/1999 | Bujard et al. |
| 6,017,544 A | 1/2000 | Srivastava |
| 6,030,618 A | 2/2000 | Srivastava |
| 6,048,530 A | 4/2000 | Srivastava |
| 6,136,315 A | 10/2000 | Srivastava |
| 6,136,954 A | 10/2000 | Bujard et al. |
| 6,156,319 A | 12/2000 | Cohen et al. |
| 6,162,436 A | 12/2000 | Srivastava |
| 6,168,793 B1 | 1/2001 | Srivastava et al. |
| 6,180,613 B1 | 1/2001 | Kaplitt et al. |
| 6,197,497 B1 | 3/2001 | Goade et al. |
| 6,200,577 B1 | 3/2001 | McLauchlan et al. |
| 6,242,667 B1 | 6/2001 | Bujard et al. |

(Continued)

FOREIGN PATENT DOCUMENTS

| AU | 198432423 | 11/1988 |
| AU | 198930061 | 6/1989 |

(Continued)

OTHER PUBLICATIONS

Koelle et al., Clinical and Vaccine Immunology, May 2008, 15(5):773-782.*

(Continued)

*Primary Examiner* — Stacy B. Chen
(74) *Attorney, Agent, or Firm* — Wolf, Greenfield & Sacks, P.C.

(57) ABSTRACT

The present invention relates to methods and compositions for the prevention and treatment of herpes virus infections. The invention provides antigenic peptides, and pharmaceutical compositions comprising complexes of antigenic peptides and adjuvants that can activate an immune response against herpes viruses. The invention also provides methods of making the antigenic peptides and complexes of antigenic peptides and adjuvants. Methods of use of the pharmaceutical compositions are also provided.

43 Claims, 4 Drawing Sheets

(56) References Cited

U.S. PATENT DOCUMENTS

Figure 1:
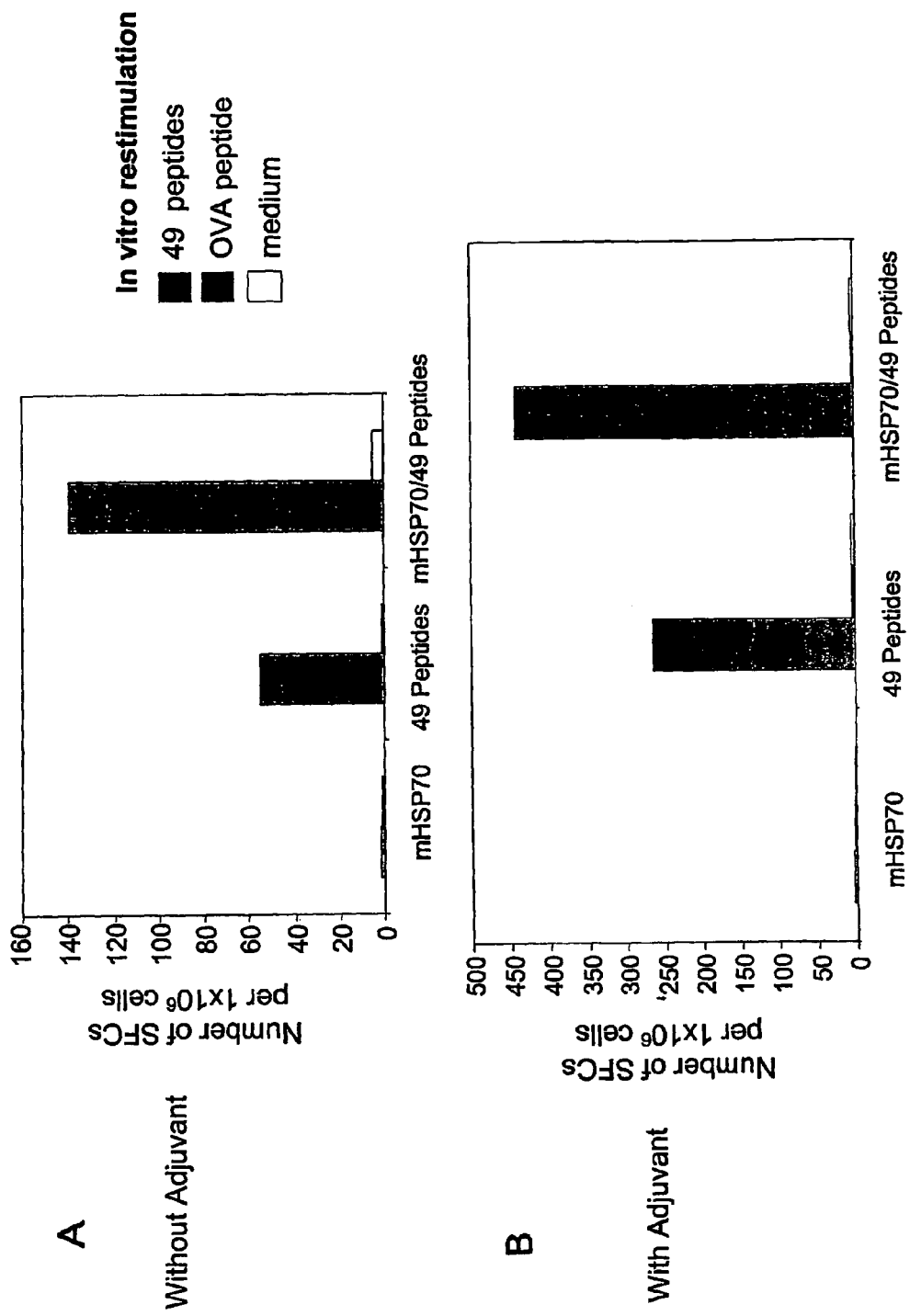

| | | |
|---|---|---|
| 6,252,136 B1 | 6/2001 | Bujard et al. |
| 6,271,348 B1 | 8/2001 | Bujard et al. |
| 6,316,003 B1 | 11/2001 | Frankel et al. |
| 6,337,074 B1 | 1/2002 | Marsden et al. |
| 6,375,952 B1 | 4/2002 | Koelle et al. |
| 6,413,518 B1 | 7/2002 | Koelle et al. |
| 6,455,503 B1 | 9/2002 | Srivastava |
| 6,461,615 B1 | 10/2002 | Srivastava |
| 6,468,540 B1 | 10/2002 | Srivastava |
| 6,572,860 B1 | 6/2003 | Zimmerman et al. |
| 6,586,573 B1 | 7/2003 | Besman et al. |
| 6,610,659 B1 | 8/2003 | Pramod |
| 7,309,491 B2 | 12/2007 | Flechtner et al. |
| 7,420,037 B2 | 9/2008 | Slusarewicz et al. |
| 7,666,581 B2 | 2/2010 | Srivastava |
| 2002/0044948 A1 | 4/2002 | Khleif et al. |
| 2002/0061316 A1 | 5/2002 | Srivastava |
| 2002/0090382 A1 | 7/2002 | Glorioso |
| 2002/0090610 A1 | 7/2002 | Hosken et al. |
| 2002/0182220 A1 | 12/2002 | Srivastava |
| 2002/0187159 A1 | 12/2002 | Srivastava |
| 2003/0118611 A1 | 6/2003 | Koelle et al. |
| 2003/0165515 A1 | 9/2003 | Srivastava |
| 2003/0165516 A1 | 9/2003 | Srivastava |
| 2006/0093612 A1 | 5/2006 | Srivastava |

FOREIGN PATENT DOCUMENTS

| | | |
|---|---|---|
| DE | 196 02 985 A1 | 7/1997 |
| DE | 19851413 | 5/2000 |
| DE | 19851415 | 5/2000 |
| EP | 101655 | 7/1983 |
| EP | 170169 | 7/1985 |
| EP | 229546 | 11/1986 |
| EP | 236145 | 3/1987 |
| EP | 410713 | 7/1990 |
| EP | 541692 | 2/1992 |
| GB | 2 251 186 A | 7/1992 |
| JP | 62115288 | 5/1987 |
| JP | 3218397 | 9/1991 |
| JP | 3220200 | 9/1991 |
| WO | WO 85/04587 | 10/1985 |
| WO | WO 87/03206 | 6/1987 |
| WO | WO 88/02634 | 4/1988 |
| WO | WO 89/10965 | 11/1989 |
| WO | WO 89/12455 | 12/1989 |
| WO | WO 90/02564 | 3/1990 |
| WO | WO 90/13652 | 11/1990 |
| WO | WO 91/13175 | 9/1991 |
| WO | WO 91/15572 | 10/1991 |
| WO | WO 92/01717 | 2/1992 |
| WO | WO 92/08484 | 5/1992 |
| WO | WO 92/08488 | 5/1992 |
| WO | WO 93/01301 | 1/1993 |
| WO | WO 93/14118 | 7/1993 |
| WO | WO 93/17712 | 9/1993 |
| WO | WO 93/18146 | 9/1993 |
| WO | WO 93/18147 | 9/1993 |
| WO | WO 93/18150 | 9/1993 |
| WO | WO 93/21529 | 10/1993 |
| WO | WO 93/24136 | 12/1993 |
| WO | WO 94/00575 | 1/1994 |
| WO | WO 94/02149 | 2/1994 |
| WO | WO 94/03208 | 2/1994 |
| WO | WO 94/03599 | 2/1994 |
| WO | WO 94/04676 | 3/1994 |
| WO | WO 94/04686 | 3/1994 |
| WO | WO 94/21807 | 9/1994 |
| WO | WO 94/29442 | 12/1994 |
| WO | WO 94/29459 | 12/1994 |
| WO | WO 95/06055 | 3/1995 |
| WO | WO 95/16779 | 6/1995 |
| WO | WO 95/18148 | 7/1995 |
| WO | WO 95/24923 | 9/1995 |
| WO | WO 96/01313 | 1/1996 |
| WO | WO 96/10411 | 4/1996 |
| WO | WO 96/32962 | 10/1996 |
| WO | WO 96/40892 | 12/1996 |
| WO | WO 96/40956 | 12/1996 |
| WO | WO 97/03199 | 1/1997 |
| WO | WO 97/06685 | 2/1997 |
| WO | WO 97/06821 | 2/1997 |
| WO | WO 97/06828 | 2/1997 |
| WO | WO 97/10000 | 3/1997 |
| WO | WO 97/10001 | 3/1997 |
| WO | WO 97/10002 | 3/1997 |
| WO | WO 97/26910 | 7/1997 |
| WO | WO 98/00567 | 1/1998 |
| WO | WO 98/03543 | 1/1998 |
| WO | WO 98/04708 | 2/1998 |
| WO | WO 98/04709 | 2/1998 |
| WO | WO 98/20016 | 5/1998 |
| WO | WO 98/46637 | 10/1998 |
| WO | WO 98/55145 | 12/1998 |
| WO | WO 99/01464 | 1/1999 |
| WO | WO 99/06540 | 2/1999 |
| WO | WO 99/16710 | 4/1999 |
| WO | WO 99/45126 | 9/1999 |
| WO | WO 99/45127 | 9/1999 |
| WO | WO 99/53043 | 10/1999 |
| WO | WO 00/01720 | 1/2000 |
| WO | WO 00/08051 | 2/2000 |
| WO | WO 00/15255 | 3/2000 |
| WO | WO 00/22110 | 4/2000 |
| WO | WO 00/31238 | 6/2000 |
| WO | WO 00/62800 A2 | 10/2000 |
| WO | WO 00/66623 | 11/2000 |
| WO | WO 00/75347 | 12/2000 |
| WO | WO 01/16163 | 3/2001 |
| WO | WO 01/18036 | 3/2001 |
| WO | WO 01/23414 | 4/2001 |
| WO | WO 01/29233 | 4/2001 |
| WO | WO 01/36616 | 5/2001 |
| WO | WO 01/37868 | 5/2001 |
| WO | WO 01/40503 | 6/2001 |
| WO | WO 01/48014 | 7/2001 |
| WO | WO 01/49832 | 7/2001 |
| WO | WO 01/51516 | 7/2001 |
| WO | WO 01/63278 A2 | 8/2001 |
| WO | WO 01/83518 | 11/2001 |
| WO | WO 01/89304 | 11/2001 |
| WO | WO 01/91787 A1 | 12/2001 |
| WO | WO 01/97847 | 12/2001 |
| WO | WO 02/02131 | 1/2002 |
| WO | WO 02/04492 | 1/2002 |
| WO | WO 02/09645 | 2/2002 |
| WO | WO 02/10410 | 2/2002 |
| WO | WO 02/16420 | 2/2002 |
| WO | WO 03/011893 A2 | 2/2003 |
| WO | WO 03/015712 A2 | 2/2003 |
| WO | WO 03/072595 | 9/2003 |
| WO | WO 03/086308 A2 * | 10/2003 |
| WO | WO 2004/091493 | 10/2004 |
| WO | WO 2010/003053 A2 * | 1/2010 |

OTHER PUBLICATIONS

L. Aurelian, Clinical and Diagnostic Laboratory Immunology, May 2004, 11(3):437-445.*
McGeoch et al., Journal of General Virology, 1987, 68:19-38.*
U.S. Appl. No. 60/503,148, filed Sep. 12, 2003, Truneh et al.
U.S. Appl. No. 90/657,722, filed Sep. 8, 2000, Srivastava.
Supplementary European Search Report for EP 04809742.2. mailed Sep. 17, 2007 (5 pgs.).
Kumaraguru et al. (2002) "Immunization with Chaperone-Peptide Complex Induces Low-Avidity Cytotoxic T Lymphocytes Providing Transient Protection Against Herpes Simplex Virus Infection,"*J. Virol.* 76:136-141.
Hoos et al. (2003) "Vaccination with Heat Shock Protein-Peptide Complexes: From Basic Science to Clinical Applications." *Expert Rev. Vaccines* 2:369-379.
Kensil et al. (2004) "Current Vaccine Adjuvants: An Overview of a Diverse Class," *Frontiers in Bioscience* 9:2972-2988.
Varnavski et al. (2005) "Effective Induction of CD8 T-Cell Memory Response by Noncovalent Complex of Heat Shock Protein 70 and Herpes Simplex Virus (HSV) Antigenic Peptide—Implication for HSV-2 Peptide Vaccine Development," Immunology 114:141-154 (Abstract No. R16).

Chenail et al. (2005) "Characterization of Peptide Binding of a Multivalent HSV-2 Vaccine Using LC/MS," Abstract of Papers, American Chemical Society. 229th ACS National Meeting Mar. 13-17, 2005 (Abstract No. 184).

Abe et al., 1993, "Different susceptibility to the IL-3 induced-protective effects between Strongyloides ratti and Nippostrongylus brasiliensis in C57BL/6 mice," Parasite Immunol. 15:643-645.

Afonso et al., 1993, "The adjuvant effect of interleukin-12 in a vaccine against Leishmanis major," Science 263:235-237.

Aldovini et al, 1992, "The new vaccines," Tech. Rev. pp. 24-31.

Auger et al., 1996, "HLA-DR4 and HLA-DR10 motifs that carry susceptibility to rheumatoid arthritis bind 70-kD heat shock proteins," Nat. Med. 2(3):306-10.

Barrios et al., 1992, "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming," Eur. J. Immunol. 22(6):1365-72.

Basombrio, 1970, "Search for common antigenicities among twenty-five sarcomas induced by methylcholanthrene", The Institute for Cancer Res. 30:2458-2462.

Basu et al., 1999, "Calreticulin, a peptide-binding chaperone of the endoplasmic reticulum, elicits tumor- and peptide-specific immunity," J. Exp. Med. 189(5):797-802.

Bensaude et al., 1983, "Spontaneous high expression of heat-shock proteins in mouse embryonal carcinoma cells and ectoderm from day 8 mouse embryo," Embo J. 2:173-177.

Blachere et al., 1993, "Heat shock protein vaccines against cancer," J. Immunotherapy 14:352-356.

Blachere et al., 1993, "Immunization with GP96 heat shock proteins isolated from tumors or influenza virus infected cells elicits MHC-restricted, antigen-specific cytotoxic T lymphocytes against the corresponding cells/antigens," J. Cell. Biochem. 17D:124 Abstract NZ 502.

Blond-Elguindi et al., 1993, "Affinity panning of a library of peptides displayed on bacteriophages reveals the binding specificity of BiP," Cell 75(4):717-28.

Boon, 1992 "Toward a genetic analysis of tumor rejection antigens," Adv. in Cancer Res. 58:177-210.

Browning et al., 1993, "Lymphotoxin β, a novel member of the TNF family that forms a heteromeric complex with lymphotoxin on the cell surface," Cell 72:847-856.

Clarke et al., 1988, "Purification of complexes of nuclear oncogene p53 with rat and Escherichia coli heat shock proteins: in vitro dissociation of hsc70 and dnaK from murine p53 by ATP," Mol. Cell Biol. 8(3):1206-1215.

Cohen, 1993, "Cancer Vaccines Get a Shot in the Arm," Science 262:841-843.

Corey et al., 1999, "Recombinant glycoprotein vaccine for the prevention of genital HSV-2 infection: two randomized controlled trials. Chiron HSV Vaccine Study Group," JAMA 282(4):331-40.

Craig, 1993, "Chaperones: helpers along the pathways to protein folding," Science 260(5116):1902-3.

Davidoff et al., 1992, "Immune response to p53 is dependent upon p53/HSP70 complexes in breast cancers," Proc. Natl. Acad. Sci. USA 89(8):3439-3442.

Dolan et al., 1998, "The genome sequence of herpes simplex virus type 2," J. Virol. 72(3):2010-21.

Durum et al., 1993, "Proinflammatory cytokines and immunity" Fundamental Immunology (Raven Press, Ltd. New York) Chapter 21 pp. 801 and 815-819.

Durum et al., 1993, "Proinflammatory cytokines and immunity" in Chapter 21 of Fundamental Immunology, 3d Ed., edited by William E. Paul, Raven Press, Ltd., New York pp. 820-822.

Ebert et al., 1987, "Characterization of an immunosuppressive factor derived from colon cancer cells," J. Immunol. 138(7):2161-2168.

Elliot et al., 1990, "Naturally processed peptides," Nature 348:195-197.

Falk et al., 1990, "Cellular peptide composition governed by major histocompatibility complex class I Molecules," Nature 348:248-251.

Falk et al., 1991 "Allele-specific motifs revealed by sequencing of self-peptides eluted from mhc molecules," Nature 351:290-296.

Feldweg et al., "Evidence for biochemical heterogeneity of gp96 heat shock protein/tumor rejecion antigen," Mount Sinai School of Medicine NZ 206, p. 108.

Finkelman et al., 1991, "Regulation and biological function of helminth-induced cytokine responses," Immunol. Today 12:A62-A66.

Flynn et al., 1989, "Peptide binding and release by proteins implicated as catalysts of protein assembly," Science 245(4916):385-90.

Flynn et al., 1991, "Peptide-binding specificity of the molecular chaperone BiP," Nature 353:726-730.

Franklin, 1993, "Making vaccines fit the cancer," New Scientist 140:17.

Gething et al., 1992, "Protein folding in the cell," Nature 355(6355):33-45.

Globerson et al., 1964, "Antigenic specificity of benzo[a]pyrene-induced sarcomas," Journal of the National Cancer Institute 32(6):1229-1242.

Gragerov et al., 1994, "Specificity of DnaK-peptide binding," J. Mol. Biol. 235(3):848-54.

Grenics et al., 1991, "Host protective immunity to Trichinella spiralis in mice: activation of Th cell subsets and lymphokine secretion in mice expressing different response phenotypes," Immunol. 74:329-332.

Gullo et al., 2004, "Heat shock proteins: to present or not, that is the question," Immunol. Lett. 94(1-2):1-10.

Hakim et al., 1991, "CD8+ T cells from mice vaccinated against Toxoplasma gondil are cytotoxic for parasite-infected or antigen-pulsed host cells," J. Immunol. 147:2310-2316.

Halevy et al., 1990, "Different tumor-derived p53 mutants exhibit distinct biological activities," Science 250(4977):113-116.

Hinds et al., 1987, "Immunological evidence for the association of p53 with a heat shock protein, hsc70, in p53-plus-ras-transformed cell lines," Mol. Cell. Biol. 7(8):2863-2869.

Hinds et al., 1990, "Mutant p53 DNA clones from human colon carcinomas cooperate with ras in transforming primary rat cells: a comparison of the "hot spot" mutant phenotypes," Cell Growth Differ. 1(12):571-580.

Howard et al., 1993, "T-cell-derived cytokines and their receptors", in Chapter 20 of Fundamental Immunology, 3d Ed., edited by William E. Paul, Raven Press, Ltd., New York pp. 763-776.

Huber et al., 1992, "Protease inhibitors interfere with the transforming growth factor-β-dependent but not the transforming growth factor-β-independent pathway of tumor cell-mediated immunosuppression," J. Immunol. 148(1):277-284.

Jakob et al., 1993, "Small heat shock proteins are molecular chaperones," J. Biol. Chem. 268:1517-1520.

Jardetzky et al., 1991, "Identification of self peptides bound to purified HLA-B27," Nature 353:326-329.

Jindal et al., 1992, "Vaccinia virus infection induces a stress response that leads to association of Hsp70 with viral proteins," J. Virol. 66(9):5357-62.

Kaufmann, 1988, "CD8+ T lymphocytes in intracellular microbial infections," Immunol. Today 9:168-174.

Kaufmann, 1993, "Immunity to intracellular bacteria," Ann. Rev. Immunol. 11:129-163.

Koelle et al., 2001, "CD8 CTL from genital herpes simplex lesions: recognition of viral tegument and immediate early proteins and lysis of infected cutaneous cells," J. Immunol. 166(6):4049-58.

Korenaga et al., 1991, "The role of interleukin-5 in protective immunity to Strongyloides venezuelensis infection in mice," Immunol. 72:502-507.

Lakey et al, 1987, "Identification of a peptide binding protein that plays a role in antigen presentation," Proc. Natl. Acad. Sci. USA 84:1659-1663.

Lanza Vecchia, 1993, "Identifying Strategies for Immune Intervention," Science 260:937-944.

Levinson et al., 1979, "Metal binding drugs induce synthesis of four proteins in normal cells," Biol. Trace Element Res. 1:15-23.

Levy, 1991, "ATP is required for in vitro assembly of mhc class I antigens but not for transfer of peptides across the membrane," Cell 67:265-274.

Li et al., 1993, "Tumor rejection antigen gp96/grp94 is an ATPase: implications for protein folding and antigen presentation," EMBO J. 12(8):3143-51.

Lin et al., 1993, "The 170-kDa glucose-regulated stress protein is an endoplasmic reticulum protein that binds immunoglobulin," Mol. Biol. Cell 4(11):1109-19.

Lindquist et al., 1988, "The heat-shock proteins," Annu. Rev. Genet. 22:631-77.

Lotz et al., 1993, "TGFβ and HIV infection," Ann. N.Y. Acad. Sci. 685:501-511.

Luescher et al., 1991 "Specific binding of antigenic peptides to cell-associated mhc class I molecules," Nature 351:72-77.

Lukacs et al., 1993,"Tumor cells transfected with a bacterial heat-shock gene lose tumorigenicity and induce protection against tumors," J. Exp. Med. 178:343-348.

Lussow et al., 1991 "Mycobacterial heat-shock proteins as carrier molecules," Eur. J. Immunol. 21:2297-2302.

Macejak et al., 1992, "Association of heat shock protein 70 with enterovirus capsid precursor P1 in infected human cells," J. Virol. 66(3):1520-7.

Madden et al., 1991 "The structure of hla-b27 reveals nonamer self-peptides bound in an extended conformation," Nature 353:321-325.

Maki et al., 1990, "Human homologue of murine tumor rejection antigen gp96: 5'-Regulatory and coding regions and relationship to stress-induced proteins," Proc. Natl. Acad. Sci. USA 87:5658-5663.

Maki, 1991, "The Human Homologue of the Mouse Tumor Rejection Antigen GP96," Ph.D. thesis, Cornell University.

Maki et al., 1993, "Mapping of the Genes for Human Endoplasmic Reticular Heat Shock Protein gp96/grp94," Somatic Cell Mol. Genetics 19(1):73-81.

McCall et al., 1989 "Biotherapy: A New Dimension in Cancer Treatment," Biotechnology 7:231-240.

Melnick, 1985, "Virus vaccines: an overview", Proceedings of the First Annual Southwest Foundation for Biomedical Research International Symposium, Houston, Texas, Nov. 8-10, 1984 American Society for Microbiology pp. 1-13.

Mikloska et al., 1998, "Herpes simplex virus type 1 glycoproteins gB, gC and gD are major targets for CD4 T-lymphocyte cytotoxicity in HLA-DR expressing human epidermal keratinocytes," J. Gen. Virol. 79 (Pt 2):353-61.

Mizoguchi et al., 1992, "Alterations in signal transduction molecules in T lymphocytes from tumorbearing mice," Science 258:1795-1798.

Moroi et al., 2000, "Induction of cellular immunity by immunization with novel hybrid peptides complexed to heat shock protein 70," Proc. Natl. Acad. Sci. U. S. A. 97(7):3485-90.

Murray, 1990, "Gamma interferon, cytokine-induced macrophage activation, and antimicrobial host defense," Diagn. Microbiol. Infect. Dis. 13:411-421.

Murray, 1993, "Cytokines as antimicrobial therapy for the T cell-deficient patient: prospects for treatment of nonviral opportunistic infections," Clin. Infect. Dis. 17:S407-413.

Nelson et al., 1992, "The translation machinery and 70 kd heat shock protein cooperate in protein synthesis," Cell 71:97-105.

Nieland et al., 1996, "Isolation of an immunodominant viral peptide that is endogenously bound to the stress protein GP96/GRP94," Proc. Natl. Acad. Sci. USA 93:6135-6139.

Novak et al., 2001, "Tetramer-guided epitope mapping: rapid identification and characterization of immunodominant CD4+ T cell epitopes from complex antigens," J. Immunol. 166(11):6665-70.

Palladino et al., 1987 "Expression of shared tumor-specific antigen by two chemically induced BALB/c sarcomas," Cancer Res. 47:5074-5079.

Peng et al., 1997, "Purification of immunogenic heat shock protein 70-peptide complexes by ADP-affinity chromatography," J. Immunol. Methods 204(1):13-21.

Pinhashi-Kimhi, 1986, "Specific interaction between the p53 cellular tumour antigen and major heat shock proteins," Nature 320(6058):182-184.

Prehn et al., 1957, "Immunity to methylcholanthrene-induced sarcomas," J. of the Natl. Cancer Inst. 18(6):769-778.

Rothman, 1989, "Polypeptide chain binding proteins: catalysts of protein folding and related processes in cells," Cell 59:591-601.

Rotzschke et al., 1990, "Isolation and analysis of naturally processed viral peptides as recognized by Cytotoxic T cells", Nature 348:252-254.

Rudensky et al., 1991, "Sequence analysis of peptides bound to MHC class II molecules," Nature 353:622-627.

Salk et al., 1993, "A strategy for prophylactic vaccination against HIV," Science 260:1270-1272.

Sawai et al., 1989, "Association of a cellular heat shock protein with simian virus 40 large T antigen in transformed cells," J. Virol. 63(9):3961-73.

Schumacher et al., 1991 "Peptide selection by mhc class I molecules," Nature 350:703-706.

Scott et al., 1993, "Immunoparasitology" Fundamental Immunology (Raven Press, ltd., New York) Capter 33 pp. 1179 and 1188-1189.

Srivastava et al., 1984 "The serologically unique cell surface antigen of zajdela ascitic hepatoma is also its tumor-associated transplantation antigen," Int. J. Cancer 33:417-422.

Srivastava et al., 1986, "Tumor rejection antigens of chemically induced sarcomas of inbred mice," Proc. Natl. Acad. Sci. U. S. A. 83(10):3407-11.

Srivastava et al., 1986, "Tumor-specific immunogenicity of stress-induced proteins: Convergence of two evolutionary pathways of antigen presentation?," Seminars in Immunol. 3:57-64.

Srivastava et al. ,1987, "5'-Structural analysis of genes encoding polymorphic antigens of chemically induced tumors," Proc. Natl. Acad. Sci. USA 84:3807-3811.

Srivastava et al., 1988, "Individually distinct transplantation antigens of chemically induced mouse tumors," Immunol. Today 9(3):78-83.

Srivastava et al., 1988, "Chromosomal assignment of the gene encoding the mouse tumor rejection antigen gp96," Immunogenetics 28(3):205-7.

Srivastava et al., 1989, "Gp96 Molecules: Recognition Elements in Tumor Immunity," Human Tumor Antigens and Specific Tumor Therapy, pp. 63-71.

Srivastava et al., 1989, "Identification of a Human Homologue of the Murine Tumor Rejection Antigen GP96," Cancer Res. 49:1341-1343.

Srivastava et al., 1990, "Immunization with Soluble Gp96 Antigens Elicits Tumor-Specific Cellular Immunity," Cellular Immunity and the Immunotherapy of Cancer, pp. 307-314.

Srivastava, 1991,"Protein tumor antigens," Curr. Opin. Immunol. 3:654-658.

Srivastava et al., 1991, "Stress-induced proteins in immune response to cancer," Curr. Top. Microbiol. Immunol. 167:109-23.

Srivastava, 1993, "Peptide-binding heat shock proteins in the endoplasmic reticulum: role in immune response to cancer and in antigen presentation," Adv. Cancer Res. 62:153-77.

Srivastava et al., Mar. 13, 1993, "Evidence for peptide-chaperoning by the endoplasmic reticular heat shock protein GP96: implications for vaccination against cancer and infectious diseases," J. Cell. Biochem. Suppl. 17D:94, Abstract NZ014.

Srivastava et al., 1994 "Heat shock proteins transfer peptides during antigen processing and CTL priming," Immunogenetics 39:93-98.

Srivastava, 1994, "Heat shock proteins in immune response to cancer: the fourth paradigm," Experientia. 50(11-12):1054-60.

Srivastava et al., 1994, "Heat shock protein-peptide complexes in cancer immunotherapy," Curr. Opin. Immunol. 6(5):728-32.

Stingley et al., 2000, "Global analysis of herpes simplex virus type 1 transcription using an oligonucleotide-based DNA microarray," J. Virol. 74(21):9916-27.

Straus et al., 1997, "Immunotherapy of recurrent genital herpes with recombinant herpes simplex virus type 2 glycoproteins D and B: results of a placebo-controlled vaccine trial," J. Infect. Dis. 176(5):1129-34.

Subbarao et al., 1992,"A General Overview of Viral Vaccine Development," Genetically Engineered Vaccines 327:51-57.

Suto et al., 1995, "A mechanism for the specific immunogenicity of heat shock protein-chaperoned peptides," Science 269(5230):1585-1.

Swain et al., 1991, "Transforming growth factor-beta and IL-4 cause helper T cell precursors to develop into distinct effector helper cells that differ in lymphokine secretion pattern and cell surface phenotype," J. Immunol. 1:2991-3000.

Szikora et al., 1990, "Structure of the gene of tum-transplantation antigen P35B presence of a point mutation in the antigenic allele," EMBO J. 9(4):1041-1050.

Thomas et al., 1982, "Molecular and cellular effects of heat shock and related treatments of mammalian tissue-culture cells," Cold Spring Habor Symp. Quant. Biol. 46:985-996.

Tigges et al., 1992, "Human CD8+ herpes simplex virus-specific cytotoxic T-lymphocyte clones recognize diverse virion protein antigens," J. Virol. 66(3):1622-34.

Troye-Blomberg et al., 1994, "T-cell control of immunity to the asexual blood stages of the malaria parasite", Crit. Rev. Immunol. 14:131-155.

Udono et al., 1993, "Heat shock protein 70-associated peptides elicit specific cancer immunity," J. Exp. Med. 178(4):1391-6.

Udono, 1993, "Heat shock proteins HSP70, HSP90 and GP96 elicit tumor specific immunity to the tumors from which they are isolated," J. Cell. Biochem. Suppl. 17D:113, Abstract NZ225.

Udono et al., 1994, "Comparison of tumor-specific immunogenicities of stress-induced proteins gp96, hsp90, and hsp70," J. Immunol. 152(11):5398-403.

Ullrich et al., 1986, "A mouse tumor-specific transplantation antigen is a heat shock-related protein," Proc. Natl. Acad. Sci. U. S. A. 83(10):3121-5.

Urban, Jr. et al., 1992, "The importance of Th2 cytokines in protective immunity to nematodes," Immunol. Rev. 127:205-220.

Van Den Enyde et al., 1991, "The gene coding for a major tumor rejection antigen of tumor P815 is identical to the normal gene of synergistic DBA/2 mice," J. Exp. Med. 173:1373-1384.

Vanbuskirk et al., 1989, "A peptide binding protein having a role in antigen presentation is a member of the hsp70 heat shock family," J. Exp. Med. 170:1799-1809.

Viitanen et al., 1992, "Mammalian mitochondrial chaperonin 60 functions as a single toroidal ring", J. Biol. Chem. 267:695-698.

Wang et al., 2001, "Characterization of heat shock protein 110 and glucose-regulated protein 170 as cancer vaccines and the effect of fever-range hyperthermia on vaccine activity," J. Immunol. 166(1):490-7.

Welch et al., 1982, "Purification of the major mammalian heat shock proteins," J. Biol. Chem. 257:14949-14959.

Welch et al., 1985, "Rapid purification of mammalian 70,000-dalton stress proteins: affinity of the proteins for nucleotides," Mol. Cell. Biol. 5:1229-1237.

Welch, 1993, "How cells respond to stress," Sci. Am. 268(5):56-64.

White et al., 1988, "Differential Distribution of the Adenovirus E1A Proteins and Colocalization of E1A with the 70-Kilodalton Cellular Heat Shock Protein in Infected Cells," J. Virol. 62(11):4153-4166.

Yin et al., 1992, "Enhancement of in vitro and in vivo antigen-specific antibody responses by interleukin 11," J. Exp. Med. 175:211-216.

Young, 1990, "Stress proteins and immunology," Annu. Rev. Immunol. 8:401-20.

No author listed. Scientific Discussion, http://www.ema.europa.eu/does/en_GB/document_library/EPAR_-_Scientific_Discussion/human/000607/WC50043692.pdf, EMEA 2006, 1-29.

Belshe R.B. et al., 2012, "Efficacy Results of a Trial of a Herpes Simplex Vaccine," NEJM, 366, 34-43.

Belshe R.B. et al., Supplementary Appendix to Efficacy results of a trial of a herpes simplex vaccine, N Engl J Med 2012;366:34-43.

Bernstein D.I., et al., 2005, "Safety and immunogenicity of glycoprotein D-adjuvant genital herpes vaccine," Clin Infect Dis, 40(9):1271-1281.

Cassanova G., et al., 2002, "A double-blind study of the efficacy and safety of the ICP10deltaPK vaccine against recurrent genital HSV-2 infections," Cutis. 70(4):235-239.

Cattamanchi A. et al., 2008, "Phase I study of a herpes simplex virus type 2 (HSV-2) DNA vaccine administered to healthy, HSV-2-seronegative adults by a needle-free injection system," Clin Vaccine Immunol. 15(11):1638-1643.

Cohen, 2010, "Painful Failure of Promising Genital Herpes Vaccine," Science (330), p. 304.

Haberthur K. et al., 2011, "CD4 T Cell Immunity Is Critical for the Control of Simian Varicella Virus Infection in a Nonhuman Primate Model of VZV Infection," PLOS Pathogens, 7(11):1-16.

de Bruyn G. et al., 2006, "A randomized controlled trial of a replication defective (gH deletion) herpes simplex virus vaccine for the treatment of recurrent genital herpes among immunocompetent subjects," Vaccine, 24(7):914-920.

Jing L. et al., 2012, "Cross-presentation and genome-wide screening reveal candidate T cells antigens for a herpes simplex virus type 1 vaccine," J Clin Invest. 1-20.

Johnston C. et al., 2011, "HSV-2: in pursuit of a vaccine," J Clin Investigation, 121(12):4600-4609.

Kumaraguru U. et al., 2004, "Concomitant Helper Response Recues Otherwise Low Avidity CD8+ Memory CTLs to Become Efficient Effectors In Vivo," J of Immunology, 172;3719-3724.

Kumaraguru, U. et al. 2002 "Immunization with Chaperone-Peptide Complex Induces Low-Avidity Cytotoxic T Lymphocytes Providing Transient Protection Against Herpes Simplex Virus Infection"; Journal of Virology, Jan. 2002, p. 136-141.

Kutinova L. et al., 1988, "Placebo-controlled study with subunit herpes simplex virus vaccine in subjects suffering from frequent herpetic recurrences," Vaccine, 6(3):223-228.

Langenberg, A.G., et al., 1995, A recombinant glycoprotein vaccine for herpes simplex virus type 2: safety and immunogenicity [corrected], Ann Intern Med 122(12):889-898.

Levin, M.J. et al., 2008, "Varicella-Zoster Virus-Specific Immune Responses in Elderly Recipients of a Herpes Zoster Vaccine," JID; 197:825-835.

Mertz, G.J. et al., 1984, "Herpes simplex virus type-2 glycoprotein-subunit vaccine: tolerance and humoral and cellular responses in human," J. Infect. Dis. 150(2):242-249.

Mertz, G.J. et al., 1990, "Double-blind, placebo-controlled trial of a herpes simplex virus type 2 glycoprotein vaccine in persons at high risk for genital herpes infection," J. Infect. Dis. 161(4):653-660.

Messaoudi I. et al., 2009, "Simian Varicella Virus Infection of Rhesus Macaques Recapitulates Essential Features of Varicella Zoster Virus Infection in Humans," PLOS Pathogens, 5(11): 1-14.

Oxman M.N. et al., 2005; "A Vaccine to Prevent Herpes Zoster and Postherpetic Neuralgia in Older Adults," NEJM 2271-2284.

Peters and Sette, 2005, "Generating quantitative models describing the sequence specificity of biological processes with the stabilized matrix method," BMC Bioinformatics, 6:132:1-9.

Schacker T. et al., 1998, "Frequency of Symptomatic and Asymptomatic Herpes Simplex Virus Type 2 Reactivations among Human Immunodeficiency Virus-Infected Men," JID, 178:1616-22.

Skinner G.R. et al., 1997, The efficacy and safety of Skinner herpes simplex vaccine towards modulation of herpes genitalis; report of a prospective double-blind placebo-controlled trial., Med Microbiol Immunol 186(1):31-36.

Stanberry, L.R. et al., 2002, "Glycoprotein-D-adjuvant vaccine to prevent genital herpes," N Engl J Med, 347(21):1652-1661.

Straus S.E. et al., 1994, "Placebo-controlled trail of vaccination with recombinant glycoprotein D of herpes simplex virus type 2 for immunotherapy of genital herpes," Lancet, 343(8911):1460-1463.

Vergans G. et al., 2007 "Selective retention of herpes simplex virus-specific T cells in latently infected human trigeminal ganglia," PNAS, 104(9):3496-3501.

Weinberg A. et al., 2009, "Varicella-Zoster Virus-Specific Immune Responses to Herpes Zoster in Elderly Participants in a Trial of a Clinically effective Zoster Vaccine," J Infect Diseases, 200; 1068-1077.

Weinberg & Levin, 2010, "VZV Cell-Mediated Immunity," Curr Top Microbiol Immunol.;342:341-57.

Zhu J. et al. 2007,"Virus-specific CD8+ T cells accumulate near sensory nerve endings in genital skin during subclinical HSV-2 reactivation," JEM, 204(3):595-603.

Zhu J. et al., 2009 "Persistence of HIV-1 receptor—positive cells after HSV-2 reactivation is a potential mechanism for increased HIV-1 acquisition," Nature Medicine 15(8):886-893.

Chentoufi et al., "HLA-A*0201-Restricted CD8+ Cytotoxic T Lymphocyte Epitopes Identified from Herpes Simplex Virus Glycoprotein D" J. Immunol. 180; 426-437 (2008).

Kim et al., "Immunodominant Epitopes in Herpes Simplex Virus Type 2 Glycoprotein D are Recognized by CD4 Lymphocytes from Both HSV-1 and HSV-2 Seropositive Subjects" J. Immunol. 181; 6604-6615 (2008).

Koelle et al., "Identification of CD8+ T Cell Epitopes in Human Herpes Virus 1" *Immune Epitope Database and Analysis Resource* http://www.iedb.org/assayId/1810282 (Nov. 10, 2011) (2 pages).

Laing et al., "Diversity in CD8+ T Cell Function and Epitope Breadth Among Persons with Genital Herpes" *J. Clin. Immunol.* (2010).

Mo et al., "A Heat Shock Protein Based Polyvalent Vaccine Targeting HSV-2: CD4$^+$ and CD8$^+$ Cellular Immunity and Protective Efficacy" *Vaccine* 29; 8350-8541 (2011).

Posavad et al., "Detailed Characterization of T Cell Responses to Herpes Simplex Virus-2 in Immune Seronegative Persons" *J. of Immunol.* 184; 3250-3259 (2010).

Wald et al. "Safety and Immunogenicity of long HSV-2 peptides complexed with rhHsc70 in HSV-2 Seropositive Persons" *Vaccine* 29; 8520-8529 (2011).

[No Author Listed] Abstracts from the IV International Conference on heat shock proteins in immune response. Farmington, Connecticut, USA. Oct. 10-13, 2004. Immunology. Jan. 2005;114(1):141-54.

Posavad et al., T cell immunity to herpes simplex viruses in seronegative subjects: silent infection or acquired immunity? J Immunol. Apr. 15, 2003;170(8):4380-8.

Posavad et al., Tipping the scales of herpes simplex virus reactivation: the important responses are local. Nat Med. Apr. 1998;4(4):381-2.

Ramachandran et al., Potential prophylactic and therapeutic vaccines for HSV infections. Curr Pharm Des. 2007;13(19):1965-73.

Draper et al., Characterization of the genes encoding herpes simplex virus type 1 and type 2 alkaline exonucleases and overlapping proteins. J Virol. Mar. 1986;57(3):1023-36.

Everett et al., Comparative DNA sequence analysis of the host shutoff genes of different strains of herpes simplex virus: type 2 strain HG52 encodes a truncated UL41 product. J Gen Virol. Jun. 1990;71 ( Pt 6):1387-90.

Galloway et al., Organization of the left-hand end of the herpes simplex virus type 2 BgIII N fragment. J Virol. Mar. 1984;49(3):724-30.

Greaves et al., Sequence, function, and regulation of the Vmw65 gene of herpes simplex virus type 2. J Virol. Dec. 1991;65(12):6705-13.

McGeoch et al., Comparative sequence analysis of the long repeat regions and adjoining parts of the long unique regions in the genomes of herpes simplex viruses types 1 and 2. J Gen Virol. Dec. 1991;72 ( Pt 12):3057-75.

Stuve et al., Structure and expression of the herpes simplex virus type 2 glycoprotein gB gene. J Virol. Feb. 1987;61(2):326-35.

Swain et al., Characterization of the gene encoding herpes simplex virus type 2 glycoprotein C and comparison with the type 1 counterpart. J Virol. Feb. 1985;53(2):561-9.

Watson, DNA sequence of the Herpes simplex virus type 2 glycoprotein D gene. Gene. Dec. 1983;26(2-3):307-12.

* cited by examiner

Fig. 1A-B

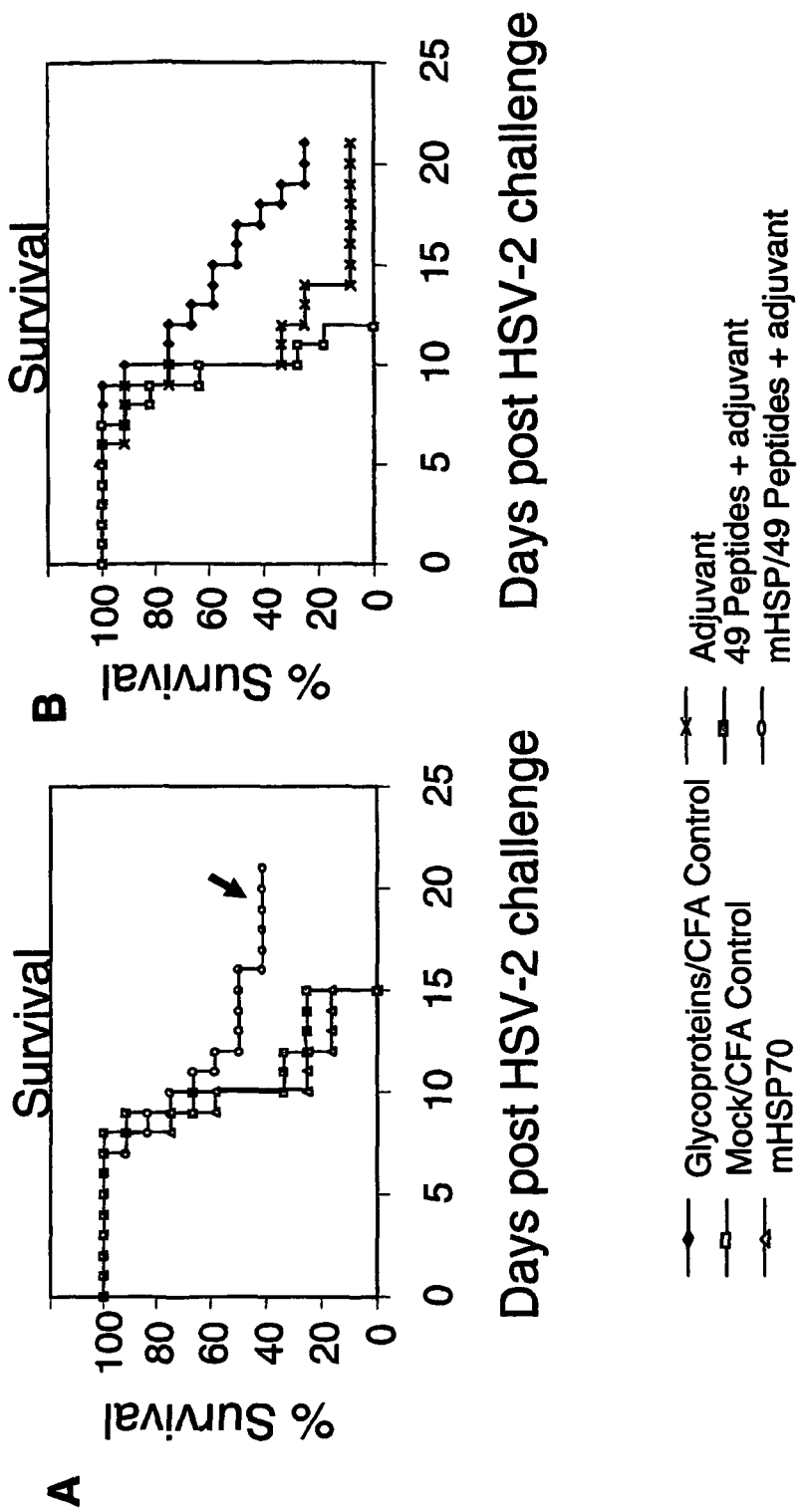
Fig. 3A-B

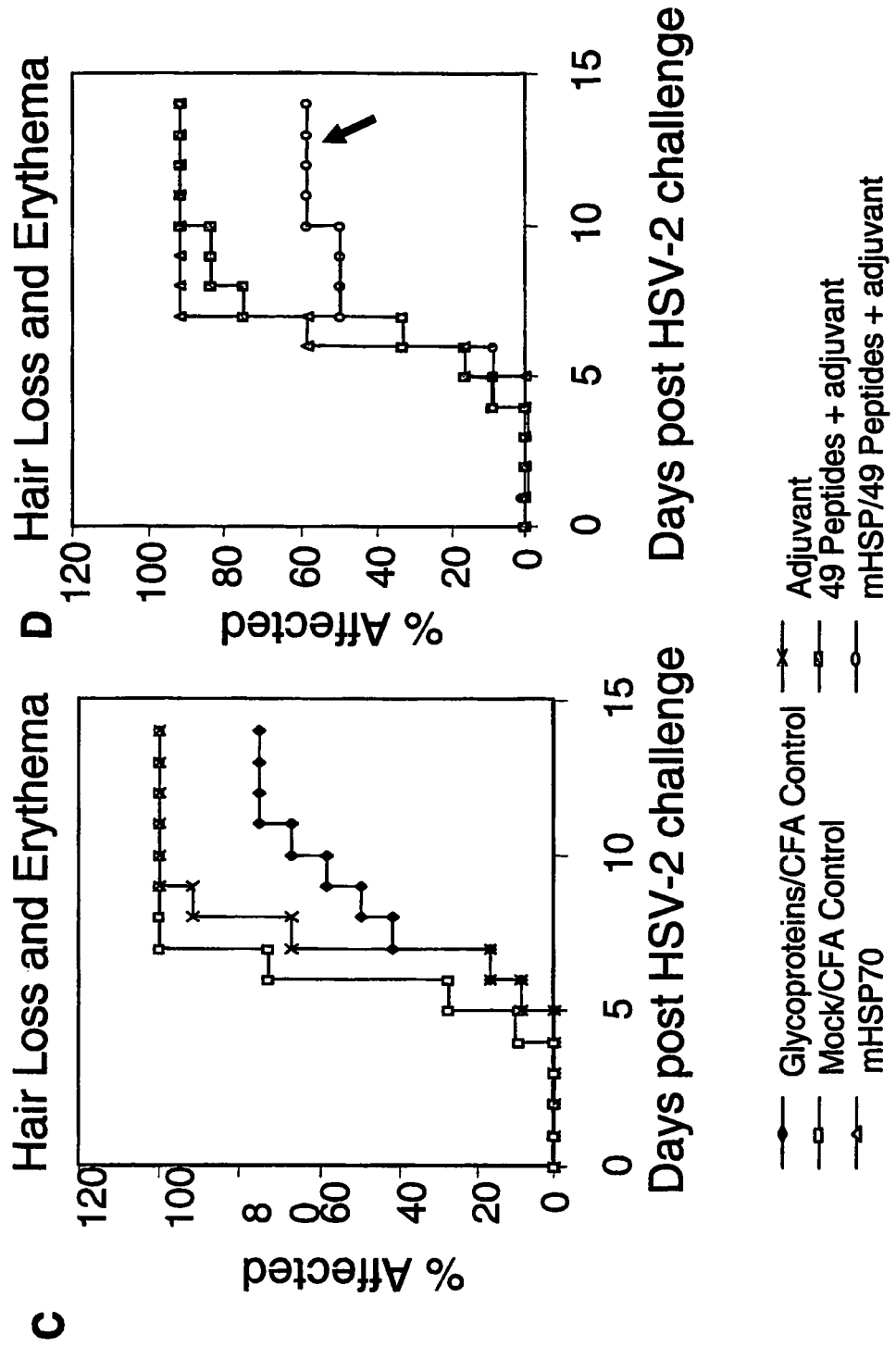
Fig. 3C-D

SEQUENCE LISTING

```
<160> NUMBER OF SEQ ID NOS: 102

<210> SEQ ID NO 1
<211> LENGTH: 35
<212> TYPE: PRT
<213> ORGANISM: Herpesvirus

<400> SEQUENCE: 1

Gly Asn Pro Arg Thr Ala Pro Arg Ser Leu Ser Leu Gly Gly His Thr
1               5                   10                  15

Val Arg Ala Leu Ser Pro Thr Pro Pro Trp Pro Gly Thr Asp Asp Glu
            20                  25                  30

Asp Asp Asp
        35

<210> SEQ ID NO 2
<211> LENGTH: 35
<212> TYPE: PRT
<213> ORGANISM: Herpesvirus

<400> SEQUENCE: 2

Arg Tyr Leu Pro Ile Ala Gly Val Ser Ser Val Val Ala Leu Ala Pro
1               5                   10                  15

Tyr Val Asn Lys Thr Val Thr Gly Asp Cys Leu Pro Val Leu Asp Met
```

```
                    20                  25                  30

Glu Thr Gly
        35

<210> SEQ ID NO 3
<211> LENGTH: 35
<212> TYPE: PRT
<213> ORGANISM: Herpesvirus

<400> SEQUENCE: 3

Ala Met Ser Arg Arg Tyr Asp Arg Ala Gln Lys Gly Phe Leu Leu Thr
1               5                   10                  15

Ser Leu Arg Arg Ala Tyr Ala Pro Leu Leu Ala Arg Glu Asn Ala Ala
                    20                  25                  30

Leu Thr Gly
        35

<210> SEQ ID NO 4
<211> LENGTH: 35
<212> TYPE: PRT
<213> ORGANISM: Herpesvirus

<400> SEQUENCE: 4

Arg Ala Tyr Leu Val Asn Pro Phe Leu Phe Ala Ala Gly Phe Leu Glu
1               5                   10                  15

Asp Leu Ser His Ser Val Phe Pro Ala Asp Thr Gln Glu Thr Thr Thr
                    20                  25                  30

Arg Arg Ala
        35

<210> SEQ ID NO 5
<211> LENGTH: 35
<212> TYPE: PRT
<213> ORGANISM: Herpesvirus

<400> SEQUENCE: 5

Ala Ser Ser Gln Ser Lys Pro Leu Ala Thr Gln Pro Pro Val Leu Ala
1               5                   10                  15

Leu Ser Asn Ala Pro Pro Arg Arg Val Ser Pro Thr Arg Gly Arg Arg
                    20                  25                  30

Arg His Thr
        35

<210> SEQ ID NO 6
<211> LENGTH: 35
<212> TYPE: PRT
<213> ORGANISM: Herpesvirus

<400> SEQUENCE: 6

Asp Glu Val Ala Pro Asp His Glu Ala Glu Leu Tyr Ala Arg Val Gln
1               5                   10                  15

Arg Pro Gly Pro Val Pro Asp Ala Glu Pro Ile Tyr Asp Thr Val Glu
                    20                  25                  30

Gly Tyr Ala
        35

<210> SEQ ID NO 7
<211> LENGTH: 35
<212> TYPE: PRT
<213> ORGANISM: Herpesvirus

<400> SEQUENCE: 7
```

```
Val Asn Ser Ala Glu Thr Asn Thr His Gly Leu Ala Tyr Asp Val Pro
 1              5                   10                  15

Glu Gly Ile Arg Arg His Leu Arg Asn Pro Lys Ile Arg Arg Ala Phe
            20                  25                  30

Thr Glu Gln
        35

<210> SEQ ID NO 8
<211> LENGTH: 35
<212> TYPE: PRT
<213> ORGANISM: Herpesvirus

<400> SEQUENCE: 8

Glu Gly Val Ser Thr Gln Asp Pro Arg Phe Val Gly Ala Phe Met Ala
 1              5                   10                  15

Ala Lys Ala Ala His Leu Glu Leu Glu Ala Arg Leu Lys Ser Arg Ala
            20                  25                  30

Arg Leu Glu
        35

<210> SEQ ID NO 9
<211> LENGTH: 35
<212> TYPE: PRT
<213> ORGANISM: Herpesvirus

<400> SEQUENCE: 9

Val Lys Ile Arg Val Glu Glu Gln Ala Ala Arg Arg Asp Phe Leu Thr
 1              5                   10                  15

Ala His Arg Arg Tyr Leu Asp Pro Ala Leu Ser Glu Arg Leu Asp Ala
            20                  25                  30

Ala Asp Asp
        35

<210> SEQ ID NO 10
<211> LENGTH: 35
<212> TYPE: PRT
<213> ORGANISM: Herpesvirus

<400> SEQUENCE: 10

Arg Thr Leu Ala Val Arg Gly Asp Ala Ser Leu Cys Gln Leu Leu Phe
 1              5                   10                  15

Gly His Pro Val Asp Ala Val Ile Leu Arg Gln Ala Thr Arg Arg Pro
            20                  25                  30

Arg Ile Thr
        35

<210> SEQ ID NO 11
<211> LENGTH: 35
<212> TYPE: PRT
<213> ORGANISM: Herpesvirus

<400> SEQUENCE: 11

Leu Gly Glu Val Thr Arg Arg Phe Pro Val Leu Leu Glu Asn Leu Met
 1              5                   10                  15

Arg Ala Leu Glu Gly Thr Ala Pro Asp Ala Phe Phe His Thr Ala Tyr
            20                  25                  30

Ala Leu Ala
        35

<210> SEQ ID NO 12
```

-continued

```
<211> LENGTH: 35
<212> TYPE: PRT
<213> ORGANISM: Herpesvirus

<400> SEQUENCE: 12

Ser Arg Leu Pro Pro His Thr Gln Pro Val Phe Ser Lys Arg Val Val
1               5                   10                  15

Met Phe Ala Trp Ser Phe Leu Val Leu Lys Pro Leu Glu Leu Val Ala
            20                  25                  30

Ala Gly Met
        35

<210> SEQ ID NO 13
<211> LENGTH: 35
<212> TYPE: PRT
<213> ORGANISM: Herpesvirus

<400> SEQUENCE: 13

Val Ala Pro Ala Cys Ile Ile Ala Ala Val Leu Ala Tyr Tyr Val Thr
1               5                   10                  15

Trp Leu Ala Arg Ala Leu Leu Leu Tyr Val Asn Ile Lys Arg Asp Arg
            20                  25                  30

Leu Pro Leu
        35

<210> SEQ ID NO 14
<211> LENGTH: 35
<212> TYPE: PRT
<213> ORGANISM: Herpesvirus

<400> SEQUENCE: 14

Val Thr Thr Ala Glu Phe Pro Arg Asp Pro Gly Gln Leu Leu Tyr Ile
1               5                   10                  15

Pro Lys Thr Tyr Leu Leu Gly Arg Pro Arg Asn Ala Ser Leu Pro Glu
            20                  25                  30

Leu Pro Glu
        35

<210> SEQ ID NO 15
<211> LENGTH: 35
<212> TYPE: PRT
<213> ORGANISM: Herpesvirus

<400> SEQUENCE: 15

Ser Ser Asp Val Pro Ser Val Ala Leu Leu Leu Phe Pro Asn Gly Thr
1               5                   10                  15

Val Ile His Leu Leu Ala Phe Asp Thr Leu Pro Ile Ala Thr Ile Ala
            20                  25                  30

Pro Gly Phe
        35

<210> SEQ ID NO 16
<211> LENGTH: 35
<212> TYPE: PRT
<213> ORGANISM: Herpesvirus

<400> SEQUENCE: 16

Ala Arg Leu Arg Leu Glu Ala Arg Leu Gly His Leu Val Ala Ala Ile
1               5                   10                  15

Leu Glu Arg Glu Gln Ser Leu Val Ala His Ala Leu Gly Tyr Gln Leu
            20                  25                  30
```

```
Ala Phe Val
        35

<210> SEQ ID NO 17
<211> LENGTH: 35
<212> TYPE: PRT
<213> ORGANISM: Herpesvirus

<400> SEQUENCE: 17

Met Leu Glu Asp His Glu Phe Val Pro Leu Glu Val Tyr Thr Arg His
1               5                   10                  15

Glu Ile Lys Asp Ser Gly Leu Leu Asp Tyr Thr Glu Val Gln Arg Arg
            20                  25                  30

Asn Gln Leu
        35

<210> SEQ ID NO 18
<211> LENGTH: 35
<212> TYPE: PRT
<213> ORGANISM: Herpesvirus

<400> SEQUENCE: 18

Tyr Ser Arg Pro Leu Val Ser Phe Arg Tyr Glu Asp Gln Gly Pro Leu
1               5                   10                  15

Ile Glu Gly Gln Leu Gly Glu Asn Asn Glu Leu Arg Leu Thr Arg Asp
            20                  25                  30

Ala Leu Glu
        35

<210> SEQ ID NO 19
<211> LENGTH: 35
<212> TYPE: PRT
<213> ORGANISM: Herpesvirus

<400> SEQUENCE: 19

Leu Glu Val Ile Phe Pro Thr Thr Asp Ala Lys Leu Asn Tyr Leu Ser
1               5                   10                  15

Arg Thr Gln Arg Leu Ala Ser Leu Leu Thr Tyr Ala Gly Pro Ile Lys
            20                  25                  30

Ala Pro Asp
        35

<210> SEQ ID NO 20
<211> LENGTH: 35
<212> TYPE: PRT
<213> ORGANISM: Herpesvirus

<400> SEQUENCE: 20

Thr Gln Asp Thr Ala Cys Val His Gly Glu Leu Leu Ala Arg Lys Arg
1               5                   10                  15

Glu Arg Phe Ala Ala Val Ile Asn Arg Phe Leu Asp Leu His Gln Ile
            20                  25                  30

Leu Arg Gly
        35

<210> SEQ ID NO 21
<211> LENGTH: 35
<212> TYPE: PRT
<213> ORGANISM: Herpesvirus

<400> SEQUENCE: 21

Asp Glu Ala Phe Pro Ile Glu Tyr Val Leu Arg Leu Met Asn Asp Trp
```

```
                1               5                  10                 15
Ala Asp Val Pro Cys Asn Pro Tyr Leu Arg Val Gln Asn Thr Gly Val
                20                 25                 30

Ser Val Leu
        35

<210> SEQ ID NO 22
<211> LENGTH: 35
<212> TYPE: PRT
<213> ORGANISM: Herpesvirus

<400> SEQUENCE: 22

Pro Gln Pro Pro Leu Pro Gln Pro Pro Leu Pro Gln Pro Pro Leu Pro
1               5                  10                 15

Gln Pro Pro Leu Pro Pro Val Thr Arg Thr Leu Thr Pro Gln Ser Arg
                20                 25                 30

Asp Ser Val
        35

<210> SEQ ID NO 23
<211> LENGTH: 35
<212> TYPE: PRT
<213> ORGANISM: Herpesvirus

<400> SEQUENCE: 23

Ala Arg Asp Val Ile Arg Glu Thr Asp Ala Phe Tyr Gly Asp Leu Ala
1               5                  10                 15

Asp Leu Asp Leu Gln Leu Arg Ala Ala Pro Pro Ala Asn Leu Tyr Ala
                20                 25                 30

Arg Leu Gly
        35

<210> SEQ ID NO 24
<211> LENGTH: 35
<212> TYPE: PRT
<213> ORGANISM: Herpesvirus

<400> SEQUENCE: 24

Leu Pro Glu Thr Ala Leu Leu Ala Glu Asn Leu Pro Gly Leu Leu Val
1               5                  10                 15

His Arg Met Ala Val Ala Leu Pro Glu Thr Pro Glu Ala Ala Phe Arg
                20                 25                 30

Glu Met Asp
        35

<210> SEQ ID NO 25
<211> LENGTH: 35
<212> TYPE: PRT
<213> ORGANISM: Herpesvirus

<400> SEQUENCE: 25

Ile Leu Ser Pro Gly Ala Leu Ala Ala Ile Glu Asn Tyr Val Arg Phe
1               5                  10                 15

Ser Ala Asp Arg Leu Leu Gly Leu Ile His Met Gln Pro Leu Tyr Ser
                20                 25                 30

Ala Pro Ala
        35

<210> SEQ ID NO 26
<211> LENGTH: 35
<212> TYPE: PRT
```

```
<213> ORGANISM: Herpesvirus

<400> SEQUENCE: 26

Val His Ser Arg Val Tyr Asn Ile Ile Gln Leu Val Leu Phe His Asn
1               5                   10                  15

Asn Asp Gln Ala Arg Arg Ala Tyr Val Ala Arg Thr Ile Asn His Pro
            20                  25                  30

Ala Ile Arg
        35

<210> SEQ ID NO 27
<211> LENGTH: 35
<212> TYPE: PRT
<213> ORGANISM: Herpesvirus

<400> SEQUENCE: 27

Ala Ala Pro Ser Gly Ala Pro Ser Lys Pro Ala Leu Arg Leu Ala His
1               5                   10                  15

Leu Phe Cys Ile Arg Val Leu Arg Ala Leu Gly Tyr Ala Tyr Ile Asn
            20                  25                  30

Ser Gly Gln
        35

<210> SEQ ID NO 28
<211> LENGTH: 35
<212> TYPE: PRT
<213> ORGANISM: Herpesvirus

<400> SEQUENCE: 28

Thr Ile Ala Glu Leu Val Glu His Arg Tyr Val Lys Tyr Val Ile Ser
1               5                   10                  15

Leu Ile Ser Pro Lys Glu Arg Gly Pro Trp Thr Leu Leu Lys Arg Leu
            20                  25                  30

Pro Ile Tyr
        35

<210> SEQ ID NO 29
<211> LENGTH: 35
<212> TYPE: PRT
<213> ORGANISM: Herpesvirus

<400> SEQUENCE: 29

Gly Tyr Phe Thr Pro Ile Ala Val Asp Leu Trp Asn Val Met Tyr Thr
1               5                   10                  15

Leu Val Val Lys Tyr Gln Arg Arg Tyr Pro Ser Tyr Asp Arg Glu Ala
            20                  25                  30

Ile Thr Leu
        35

<210> SEQ ID NO 30
<211> LENGTH: 35
<212> TYPE: PRT
<213> ORGANISM: Herpesvirus

<400> SEQUENCE: 30

Gly Pro Gly Ala Ser Pro Arg Leu Tyr Ser Val Val Gly Pro Leu Gly
1               5                   10                  15

Arg Gln Arg Leu Ile Ile Glu Glu Leu Thr Leu Glu Thr Gln Gly Met
            20                  25                  30

Tyr Tyr Trp
        35
```

<210> SEQ ID NO 31
<211> LENGTH: 35
<212> TYPE: PRT
<213> ORGANISM: Herpesvirus

<400> SEQUENCE: 31

Asp Arg Pro Ser Ala Tyr Gly Thr Trp Val Arg Val Arg Val Phe Arg
1               5                   10                  15

Pro Pro Ser Leu Thr Ile His Pro His Ala Val Leu Glu Gly Gln Pro
            20                  25                  30

Phe Lys Ala
        35

<210> SEQ ID NO 32
<211> LENGTH: 35
<212> TYPE: PRT
<213> ORGANISM: Herpesvirus

<400> SEQUENCE: 32

Pro Ala Thr Leu Ile Pro Arg Ala Ala Ala Lys His Leu Ala Ala Leu
1               5                   10                  15

Thr Arg Val Gln Ala Glu Arg Ser Ser Gly Tyr Trp Trp Val Asn Gly
            20                  25                  30

Asp Gly Ile
        35

<210> SEQ ID NO 33
<211> LENGTH: 35
<212> TYPE: PRT
<213> ORGANISM: Herpesvirus

<400> SEQUENCE: 33

Asp Pro Ala Gly Asp Cys Asp Pro Ser Leu His Val Leu Leu Arg Pro
1               5                   10                  15

Thr Leu Leu Pro Lys Leu Leu Val Arg Ala Pro Phe Lys Ser Gly Ala
            20                  25                  30

Ala Ala Ala
        35

<210> SEQ ID NO 34
<211> LENGTH: 35
<212> TYPE: PRT
<213> ORGANISM: Herpesvirus

<400> SEQUENCE: 34

Ala Asp Pro Ser Arg Pro Ser Thr Asp Thr Ala Leu Arg Leu Ser Glu
1               5                   10                  15

Leu Leu Ala Tyr Val Ser Val Leu Tyr His Trp Ala Ser Trp Met Leu
            20                  25                  30

Trp Thr Ala
        35

<210> SEQ ID NO 35
<211> LENGTH: 35
<212> TYPE: PRT
<213> ORGANISM: Herpesvirus

<400> SEQUENCE: 35

Phe Arg Arg Gly Ala Gly Pro Met Arg Ala Arg Pro Arg Gly Glu Val
1               5                   10                  15

```
Arg Phe Leu His Tyr Asp Glu Ala Gly Tyr Ala Leu Tyr Arg Asp Ser
        20                  25                  30

Ser Ser Asp
        35

<210> SEQ ID NO 36
<211> LENGTH: 35
<212> TYPE: PRT
<213> ORGANISM: Herpesvirus

<400> SEQUENCE: 36

Ser Pro Thr Ala Pro Trp Thr Pro Arg Val Ala Gly Phe Asn Lys Arg
1               5                   10                  15

Val Phe Cys Ala Ala Val Gly Arg Leu Ala Ala Thr His Ala Arg Leu
        20                  25                  30

Ala Ala Val
        35

<210> SEQ ID NO 37
<211> LENGTH: 35
<212> TYPE: PRT
<213> ORGANISM: Herpesvirus

<400> SEQUENCE: 37

Ala Thr Tyr Leu Leu Asn Tyr Ala Gly Arg Ile Val Ser Ser Val Phe
1               5                   10                  15

Leu Gln Tyr Pro Tyr Thr Lys Ile Thr Arg Leu Leu Cys Glu Leu Ser
        20                  25                  30

Val Gln Arg
        35

<210> SEQ ID NO 38
<211> LENGTH: 35
<212> TYPE: PRT
<213> ORGANISM: Herpesvirus

<400> SEQUENCE: 38

Leu Ser Gly Ile Ala Val Arg Leu Cys Tyr Ile Ala Val Ala Gly
1               5                   10                  15

Val Val Leu Val Ala Leu Arg Tyr Glu Gln Glu Ile Gln Arg Arg Leu
        20                  25                  30

Phe Asp Leu
        35

<210> SEQ ID NO 39
<211> LENGTH: 35
<212> TYPE: PRT
<213> ORGANISM: Herpesvirus

<400> SEQUENCE: 39

Val Ser Ile Ile Ala Leu Thr Glu Leu Tyr Phe Ile Leu Arg Arg Gly
1               5                   10                  15

Ser Ala Pro Lys Asn Ala Glu Pro Ala Ala Pro Arg Gly Arg Ser Lys
        20                  25                  30

Gly Trp Ser
        35

<210> SEQ ID NO 40
<211> LENGTH: 35
<212> TYPE: PRT
<213> ORGANISM: Herpesvirus
```

```
<400> SEQUENCE: 40

Asp Pro Ile Ile Gly Thr Ala Ala Val Leu Glu Asn Leu Ala Thr
 1               5                  10                  15

Arg Leu Arg Pro Phe Leu Gln Cys Tyr Leu Lys Ala Arg Gly Leu Cys
            20                  25                  30

Gly Leu Asp
        35

<210> SEQ ID NO 41
<211> LENGTH: 35
<212> TYPE: PRT
<213> ORGANISM: Herpesvirus

<400> SEQUENCE: 41

Leu Asp Asp Leu Cys Ser Arg Arg Leu Ser Asp Ile Lys Asp Ile
 1               5                  10                  15

Ala Ser Phe Val Leu Val Ile Leu Ala Arg Leu Ala Asn Arg Val Glu
            20                  25                  30

Arg Gly Val
        35

<210> SEQ ID NO 42
<211> LENGTH: 35
<212> TYPE: PRT
<213> ORGANISM: Herpesvirus

<400> SEQUENCE: 42

Ile Val Gly Ile Leu Gly Cys Ala Ala Val Gly Ala Ala Pro Thr Gly
 1               5                  10                  15

Pro Ala Ser Asp Thr Thr Asn Ala Thr Ala Arg Leu Pro Thr His Pro
            20                  25                  30

Pro Leu Ile
        35

<210> SEQ ID NO 43
<211> LENGTH: 35
<212> TYPE: PRT
<213> ORGANISM: Herpesvirus

<400> SEQUENCE: 43

Arg Trp Ser Tyr Tyr Asp Ser Phe Ser Ala Val Ser Glu Asp Asn Leu
 1               5                  10                  15

Gly Phe Leu Met His Ala Pro Ala Phe Glu Thr Ala Gly Thr Tyr Leu
            20                  25                  30

Arg Leu Val
        35

<210> SEQ ID NO 44
<211> LENGTH: 35
<212> TYPE: PRT
<213> ORGANISM: Herpesvirus

<400> SEQUENCE: 44

Ser Lys Ala Tyr Gln Gln Gly Val Thr Val Asp Ser Ile Gly Met Leu
 1               5                  10                  15

Pro Arg Phe Ile Pro Glu Asn Gln Arg Thr Val Ala Leu Tyr Ser Leu
            20                  25                  30

Lys Ile Ala
        35
```

```
<210> SEQ ID NO 45
<211> LENGTH: 35
<212> TYPE: PRT
<213> ORGANISM: Herpesvirus

<400> SEQUENCE: 45

Asp Ser Val Arg Ser Ser Ala Ser Val Pro Leu Tyr Pro Ala Ala Ser
1               5                   10                  15

Pro Val Pro Ala Glu Ala Tyr Tyr Ser Glu Ser Glu Asp Glu Ala Ala
            20                  25                  30

Asn Asp Phe
        35

<210> SEQ ID NO 46
<211> LENGTH: 35
<212> TYPE: PRT
<213> ORGANISM: Herpesvirus

<400> SEQUENCE: 46

Ala Gly Leu Pro Ser Pro Val Pro Tyr Ala Pro Leu Gly Ser Pro Asp
1               5                   10                  15

Pro Ser Ser Pro Arg Gln Arg Thr Tyr Val Leu Pro Arg Val Gly Ile
            20                  25                  30

His Asn Ala
        35

<210> SEQ ID NO 47
<211> LENGTH: 35
<212> TYPE: PRT
<213> ORGANISM: Herpesvirus

<400> SEQUENCE: 47

Asp Arg Pro Pro Glu Ser Pro Gly Ser Glu Leu Tyr Pro Leu Asn Ala
1               5                   10                  15

Gln Ala Leu Ala His Leu Gln Met Leu Pro Ala Asp His Arg Ala Phe
            20                  25                  30

Phe Arg Thr
        35

<210> SEQ ID NO 48
<211> LENGTH: 35
<212> TYPE: PRT
<213> ORGANISM: Herpesvirus

<400> SEQUENCE: 48

Val Ser Pro Ala His Pro Gln Thr Pro Val Gly Ala Gly Ser Arg Asp
1               5                   10                  15

Leu Ser Leu Lys Gly Thr Pro Ser Asp Gly Met Gln Pro Arg Gly Ala
            20                  25                  30

Asp Thr Leu
        35

<210> SEQ ID NO 49
<211> LENGTH: 35
<212> TYPE: PRT
<213> ORGANISM: Herpesvirus

<400> SEQUENCE: 49

Ala Ala Gly Lys Arg Gly Asp Ser Gly Leu Leu Arg Val Cys Ala Ala
1               5                   10                  15

Leu Ser Ile Pro Lys Pro Ser Glu Ala Val Arg Pro Ser Arg Ile Pro
            20                  25                  30
```

Arg Ala Pro
        35

<210> SEQ ID NO 50
<211> LENGTH: 35
<212> TYPE: PRT
<213> ORGANISM: Herpesvirus

<400> SEQUENCE: 50

Thr Gly His Ile Gly Ala Tyr Val Val Leu Val Asp Gln Thr Gly Asn
1               5                   10                  15

Val Ala Asp Leu Leu Arg Ala Ala Ala Pro Ala Trp Ser Arg Arg Thr
            20                  25                  30

Leu Leu Pro
        35

<210> SEQ ID NO 51
<211> LENGTH: 35
<212> TYPE: PRT
<213> ORGANISM: Herpesvirus

<400> SEQUENCE: 51

Val Arg Pro Pro Asp Tyr Pro Thr Pro Pro Ala Ser Glu Trp Asn Ser
1               5                   10                  15

Leu Trp Met Thr Pro Val Gly Asn Met Leu Phe Asp Gln Gly Thr Leu
            20                  25                  30

Val Gly Ala
        35

<210> SEQ ID NO 52
<211> LENGTH: 35
<212> TYPE: PRT
<213> ORGANISM: Herpesvirus

<400> SEQUENCE: 52

Gly Asp Val Ala Leu Asp Gln Ala Cys Phe Arg Ile Ser Gly Ala Ala
1               5                   10                  15

Arg Asn Ser Ser Ser Phe Ile Ser Gly Ser Val Ala Arg Ala Val Pro
            20                  25                  30

His Leu Gly
        35

<210> SEQ ID NO 53
<211> LENGTH: 35
<212> TYPE: PRT
<213> ORGANISM: Herpesvirus

<400> SEQUENCE: 53

Gly Ala Pro Asp Val Ser Ala Leu Gly Ala Gln Gly Val Leu Leu Leu
1               5                   10                  15

Ser Thr Arg Asp Leu Ala Phe Ala Gly Ala Val Glu Phe Leu Gly Leu
            20                  25                  30

Leu Ala Gly
        35

<210> SEQ ID NO 54
<211> LENGTH: 35
<212> TYPE: PRT
<213> ORGANISM: Herpesvirus

<400> SEQUENCE: 54

Ser Gly Glu Ala Val Asp Glu Pro Ala Ala Asp Gly Val Val Ser Pro
1               5                   10                  15

Arg Gln Leu Ala Leu Leu Ala Ser Met Val Asp Glu Ala Val Arg Thr
            20                  25                  30

Ile Pro Ser
        35

<210> SEQ ID NO 55
<211> LENGTH: 35
<212> TYPE: PRT
<213> ORGANISM: Herpesvirus

<400> SEQUENCE: 55

Arg Thr Pro Ala Asp Asp Val Ser Trp Arg Tyr Glu Ala Pro Ser Val
1               5                   10                  15

Ile Asp Tyr Ala Arg Ile Asp Gly Ile Phe Leu Arg Tyr His Cys Pro
            20                  25                  30

Gly Leu Asp
        35

<210> SEQ ID NO 56
<211> LENGTH: 35
<212> TYPE: PRT
<213> ORGANISM: Herpesvirus

<400> SEQUENCE: 56

Ala Trp Leu Leu Gln Ile Thr Val Leu Leu Leu Ala His Arg Ile Ser
1               5                   10                  15

Gln Leu Ala His Leu Ile Tyr Val Leu His Phe Ala Cys Leu Val Tyr
            20                  25                  30

Leu Ala Ala
        35

<210> SEQ ID NO 57
<211> LENGTH: 35
<212> TYPE: PRT
<213> ORGANISM: Herpesvirus

<400> SEQUENCE: 57

Ser Ala Pro Ser Met Leu Ile Cys Leu Thr Thr Leu Phe Ala Leu Leu
1               5                   10                  15

Val Val Ser Leu Leu Leu Val Val Glu Gly Val Leu Cys His Tyr Val
            20                  25                  30

Arg Val Leu
        35

<210> SEQ ID NO 58
<211> LENGTH: 35
<212> TYPE: PRT
<213> ORGANISM: Herpesvirus

<400> SEQUENCE: 58

Val Pro Leu Arg Leu Asp Thr Gln Ser Leu Leu Ala Thr Tyr Ala Ile
1               5                   10                  15

Thr Ser Thr Leu Leu Leu Ala Ala Ala Val Tyr Ala Ala Val Gly Ala
            20                  25                  30

Val Thr Ser
        35

<210> SEQ ID NO 59
<211> LENGTH: 35

```
<212> TYPE: PRT
<213> ORGANISM: Herpesvirus

<400> SEQUENCE: 59

Gly Thr Tyr Leu Arg Gln Val His Gly Leu Ile Asp Pro Ala Pro Thr
 1               5                  10                  15

His His Arg Ile Val Gly Pro Val Arg Ala Val Met Thr Asn Ala Leu
            20                  25                  30

Leu Leu Gly
        35

<210> SEQ ID NO 60
<211> LENGTH: 35
<212> TYPE: PRT
<213> ORGANISM: Herpesvirus

<400> SEQUENCE: 60

Ile Thr Thr Asp Gly Gly Glu Val Val Ser Leu Thr Ala His Glu Phe
 1               5                  10                  15

Asp Val Val Asp Ile Glu Ser Glu Glu Gly Asn Phe Tyr Val Pro
            20                  25                  30

Pro Asp Val
        35

<210> SEQ ID NO 61
<211> LENGTH: 35
<212> TYPE: PRT
<213> ORGANISM: Herpesvirus

<400> SEQUENCE: 61

Arg Val Val Thr Arg Ala Pro Gly Pro Gln Tyr Arg Arg Ala Ser Asp
 1               5                  10                  15

Pro Pro Ser Arg His Thr Arg Arg Asp Pro Asp Val Ala Arg Pro
            20                  25                  30

Pro Ala Thr
        35

<210> SEQ ID NO 62
<211> LENGTH: 35
<212> TYPE: PRT
<213> ORGANISM: Herpesvirus

<400> SEQUENCE: 62

Arg Ala Glu Phe Asn Asn Arg Pro Leu Lys His Asp Val Gly Leu Ala
 1               5                  10                  15

Val Asp Leu Tyr Ala Leu Gly Gln Thr Leu Leu Glu Leu Leu Val Ser
            20                  25                  30

Val Tyr Val
        35

<210> SEQ ID NO 63
<211> LENGTH: 35
<212> TYPE: PRT
<213> ORGANISM: Herpesvirus

<400> SEQUENCE: 63

Leu Tyr Ala Leu Gly Gln Thr Leu Leu Glu Leu Leu Val Ser Val Tyr
 1               5                  10                  15

Val Ala Pro Ser Leu Gly Val Pro Val Thr Arg Val Pro Gly Tyr Gln
            20                  25                  30

Tyr Phe Asn
```

```
<210> SEQ ID NO 64
<211> LENGTH: 35
<212> TYPE: PRT
<213> ORGANISM: Herpesvirus

<400> SEQUENCE: 64

Gln Arg Gln Ile Val Phe Pro Ala Tyr Asp Met Asp Leu Gly Lys Tyr
1               5                   10                  15

Ile Gly Gln Leu Ala Ser Leu Arg Ala Thr Thr Pro Ser Val Ala Thr
            20                  25                  30

Ala Leu His
        35

<210> SEQ ID NO 65
<211> LENGTH: 35
<212> TYPE: PRT
<213> ORGANISM: Herpesvirus

<400> SEQUENCE: 65

Pro Glu Ala Asp Leu Val Ala Arg Ile Ala Asn Ser Val Phe Val Trp
1               5                   10                  15

Arg Val Val Arg Gly Asp Glu Arg Leu Lys Ile Phe Arg Cys Leu Thr
            20                  25                  30

Val Leu Thr
        35

<210> SEQ ID NO 66
<211> LENGTH: 35
<212> TYPE: PRT
<213> ORGANISM: Herpesvirus

<400> SEQUENCE: 66

Arg Gly Gly Pro Arg Ala Ala Gly Glu Asp Val Leu Asn Asp Val Leu
1               5                   10                  15

Thr Leu Val Pro Gly Thr Ala Lys Pro Arg Ser Leu Val Glu Trp Leu
            20                  25                  30

Asp Arg Gly
        35

<210> SEQ ID NO 67
<211> LENGTH: 35
<212> TYPE: PRT
<213> ORGANISM: Herpesvirus

<400> SEQUENCE: 67

Thr Ala Thr Ala Glu Asp Val Ser Ile Thr Gln Glu Asn Glu Glu Ile
1               5                   10                  15

Leu Ala Leu Val Gln Arg Ala Val Gln Asp Val Thr Arg Arg His Pro
            20                  25                  30

Val Arg Ala
        35

<210> SEQ ID NO 68
<211> LENGTH: 35
<212> TYPE: PRT
<213> ORGANISM: Herpesvirus

<400> SEQUENCE: 68

Asn Pro Asp Pro Arg Thr Pro Gly Glu Leu Pro Asp Leu Asn Val Leu
1               5                   10                  15
```

Tyr Tyr Asn Gly Ala Arg Leu Ser Leu Val Ala Asp Val Gln Gln Leu
            20                  25                  30

Ala Ser Val
        35

<210> SEQ ID NO 69
<211> LENGTH: 35
<212> TYPE: PRT
<213> ORGANISM: Herpesvirus

<400> SEQUENCE: 69

Thr Glu Leu Arg Ser Leu Val Leu Asn Met Val Tyr Ser Ile Thr Glu
1               5                   10                  15

Gly Thr Thr Leu Ile Leu Thr Leu Ile Pro Arg Leu Leu Ala Leu Ser
            20                  25                  30

Ala Gln Asp
        35

<210> SEQ ID NO 70
<211> LENGTH: 35
<212> TYPE: PRT
<213> ORGANISM: Herpesvirus

<400> SEQUENCE: 70

Ala Ser Tyr Val Val Thr His Thr Pro Leu Pro Arg Gly Ile Gly Tyr
1               5                   10                  15

Lys Leu Thr Gly Val Asp Val Arg Arg Pro Leu Phe Ile Thr Tyr Leu
            20                  25                  30

Thr Ala Thr
        35

<210> SEQ ID NO 71
<211> LENGTH: 35
<212> TYPE: PRT
<213> ORGANISM: Herpesvirus

<400> SEQUENCE: 71

Val Gly Gln Pro Gln Tyr Tyr Leu Ala Thr Gly Gly Phe Leu Ile Ala
1               5                   10                  15

Tyr Gln Pro Leu Leu Ser Asn Thr Leu Ala Glu Leu Tyr Val Arg Glu
            20                  25                  30

Tyr Met Arg
        35

<210> SEQ ID NO 72
<211> LENGTH: 35
<212> TYPE: PRT
<213> ORGANISM: Herpesvirus

<400> SEQUENCE: 72

Ala Leu Arg Ser Gln Thr Leu Glu Ser Leu Asp Ala Arg Tyr Val Ser
1               5                   10                  15

Arg Asp Gly Ala Gly Asp Ala Ala Val Trp Phe Glu Asp Met Thr Pro
            20                  25                  30

Ala Glu Leu
        35

<210> SEQ ID NO 73
<211> LENGTH: 35
<212> TYPE: PRT
<213> ORGANISM: Herpesvirus

<400> SEQUENCE: 73

Val Gln Leu Phe Arg Ala Pro Arg Pro Gly Pro Ala Leu Leu Leu
1               5                   10                  15
Leu Ala Ala Gly Leu Phe Leu Gly Ala Ala Ile Trp Trp Ala Val Gly
            20                  25                  30
Ala Arg Leu
        35

<210> SEQ ID NO 74
<211> LENGTH: 35
<212> TYPE: PRT
<213> ORGANISM: Herpesvirus

<400> SEQUENCE: 74

Gly Ala Pro Gly Gly Ala Ile Thr Ala Glu Gln Thr Asn Val Ile Leu
1               5                   10                  15
His Ser Thr Glu Thr Thr Gly Leu Ser Leu Gly Asp Leu Asp Asp Val
            20                  25                  30
Lys Gly Arg
        35

<210> SEQ ID NO 75
<211> LENGTH: 35
<212> TYPE: PRT
<213> ORGANISM: Herpesvirus

<400> SEQUENCE: 75

Gly Lys Pro Tyr Gly Gly Arg Pro Gly Asp Ala Phe Glu Gly Leu Val
1               5                   10                  15
Gln Arg Ile Arg Leu Ile Val Pro Ala Thr Leu Arg Gly Gly Gly
            20                  25                  30
Glu Ser Gly
        35

<210> SEQ ID NO 76
<211> LENGTH: 35
<212> TYPE: PRT
<213> ORGANISM: Herpesvirus

<400> SEQUENCE: 76

Ala Pro Gln Phe His Arg Pro Ser Thr Ile Thr Ala Asp Asn Val Arg
1               5                   10                  15
Ala Leu Gly Met Arg Gly Leu Val Leu Ala Thr Asn Asn Ala Gln Phe
            20                  25                  30
Ile Met Asp
        35

<210> SEQ ID NO 77
<211> LENGTH: 35
<212> TYPE: PRT
<213> ORGANISM: Herpesvirus

<400> SEQUENCE: 77

Pro His Gly Thr Gln Gly Ala Val Arg Glu Phe Leu Arg Gly Gln Ala
1               5                   10                  15
Ala Ala Leu Thr Asp Leu Gly Val Thr His Ala Asn Asn Thr Phe Ala
            20                  25                  30
Pro Gln Pro
        35

```
<210> SEQ ID NO 78
<211> LENGTH: 35
<212> TYPE: PRT
<213> ORGANISM: Herpesvirus

<400> SEQUENCE: 78

Glu Thr Tyr Leu Gln Asp Glu Pro Phe Val Glu Arg Arg Val Ala Ile
1               5                   10                  15

Thr His Pro Leu Arg Gly Glu Ile Gly Gly Leu Gly Ala Leu Phe Val
            20                  25                  30

Gly Val Val
        35

<210> SEQ ID NO 79
<211> LENGTH: 35
<212> TYPE: PRT
<213> ORGANISM: Herpesvirus

<400> SEQUENCE: 79

Asp Thr Ala Thr Ala Leu Ala Gly Leu His Pro Ala Phe Val Val Val
1               5                   10                  15

Leu Lys Thr Leu Phe Ala Asp Ala Pro Glu Thr Pro Val Leu Val Gln
            20                  25                  30

Phe Phe Ser
        35

<210> SEQ ID NO 80
<211> LENGTH: 35
<212> TYPE: PRT
<213> ORGANISM: Herpesvirus

<400> SEQUENCE: 80

Ala Arg Leu Arg Asp Glu Val Val Arg Arg Val Pro Trp Glu Met Asn
1               5                   10                  15

Phe Asp Ala Leu Gly Gly Leu Leu Ala Glu Phe Asp Ala Ala Ala Ala
            20                  25                  30

Asp Leu Ala
        35

<210> SEQ ID NO 81
<211> LENGTH: 35
<212> TYPE: PRT
<213> ORGANISM: Herpesvirus

<400> SEQUENCE: 81

Val Thr Ala Met Asp Leu Val Leu Ala Ala Val Leu Leu Gly Ala Pro
1               5                   10                  15

Val Val Val Ala Leu Arg Asn Thr Thr Ala Phe Ser Arg Glu Ser Glu
            20                  25                  30

Leu Glu Leu
        35

<210> SEQ ID NO 82
<211> LENGTH: 35
<212> TYPE: PRT
<213> ORGANISM: Herpesvirus

<400> SEQUENCE: 82

Leu Met Ala Arg Val Arg Thr Asp Ala Ala Val Phe Asp Pro Asp Val
1               5                   10                  15

Pro Phe Leu Ser Ala Ser Ala Leu Ala Ile Phe Arg Pro Ala Val Thr
```

-continued

```
                    20                  25                  30

Gly Leu Leu
        35

<210> SEQ ID NO 83
<211> LENGTH: 35
<212> TYPE: PRT
<213> ORGANISM: Herpesvirus

<400> SEQUENCE: 83

Ala Asn Leu Thr Thr Pro Ala Tyr Ser Leu Leu Phe Pro Ser Pro Ile
1               5                   10                  15

Val Gln Glu Gly Leu Arg Phe Leu Ala Leu Val Ser Asn Trp Val Thr
            20                  25                  30

Leu Phe Ser
        35

<210> SEQ ID NO 84
<211> LENGTH: 35
<212> TYPE: PRT
<213> ORGANISM: Herpesvirus

<400> SEQUENCE: 84

Val Gly Pro Thr Met Gln Met Ala Asp Asn Ile Glu Gln Leu Leu Arg
1               5                   10                  15

Glu Leu Tyr Val Ile Ala Arg Gly Ala Val Glu Gln Leu Arg Pro Ala
            20                  25                  30

Val Gln Leu
        35

<210> SEQ ID NO 85
<211> LENGTH: 35
<212> TYPE: PRT
<213> ORGANISM: Herpesvirus

<400> SEQUENCE: 85

Ser Val Asp Leu Ser Pro Gln Gly Leu Ala Ala Thr Leu Ser Met Asp
1               5                   10                  15

Trp Leu Leu Ile Asn Glu Leu Leu Gln Val Thr Asp Gly Val Phe Arg
            20                  25                  30

Ala Ser Ala
        35

<210> SEQ ID NO 86
<211> LENGTH: 35
<212> TYPE: PRT
<213> ORGANISM: Herpesvirus

<400> SEQUENCE: 86

Ser Ile Pro Glu Lys Phe Ile Leu Met Ile Leu Ile Glu Gly Val Phe
1               5                   10                  15

Phe Ala Ala Ser Phe Ala Ala Ile Ala Tyr Leu Arg Thr Asn Asn Leu
            20                  25                  30

Leu Arg Val
        35

<210> SEQ ID NO 87
<211> LENGTH: 35
<212> TYPE: PRT
<213> ORGANISM: Herpesvirus

<400> SEQUENCE: 87
```

```
Leu Arg Ser Leu Ser Ile Leu Asn Arg Trp Leu Glu Thr Glu Leu Val
1               5                   10                  15

Phe Val Gly Asp Glu Glu Asp Val Ser Lys Leu Ser Glu Gly Glu Leu
                20                  25                  30

Gly Phe Tyr
        35

<210> SEQ ID NO 88
<211> LENGTH: 35
<212> TYPE: PRT
<213> ORGANISM: Herpesvirus

<400> SEQUENCE: 88

Ser Ser Glu Ile Leu Thr Pro Pro Glu Leu Val Gln Val Pro Asn Ala
1               5                   10                  15

Gln Arg Val Ala Glu His Arg Gly Tyr Val Ala Gly Arg Arg Arg His
                20                  25                  30

Val Ile His
        35

<210> SEQ ID NO 89
<211> LENGTH: 35
<212> TYPE: PRT
<213> ORGANISM: Herpesvirus

<400> SEQUENCE: 89

Glu Gly Ala Gly Ile Gly Val Ala Val Leu Val Ala Val Val Leu Ala
1               5                   10                  15

Gly Thr Ala Val Val Tyr Leu Thr His Ala Ser Ser Val Arg Tyr Arg
                20                  25                  30

Arg Leu Arg
        35

<210> SEQ ID NO 90
<211> LENGTH: 35
<212> TYPE: PRT
<213> ORGANISM: Herpesvirus

<400> SEQUENCE: 90

Thr Arg Thr Glu Phe Arg Leu Gln Ile Trp Arg Tyr Ala Thr Ala Thr
1               5                   10                  15

Asp Ala Glu Ile Gly Thr Ala Pro Ser Leu Glu Glu Val Met Val Asn
                20                  25                  30

Val Ser Ala
        35

<210> SEQ ID NO 91
<211> LENGTH: 35
<212> TYPE: PRT
<213> ORGANISM: Herpesvirus

<400> SEQUENCE: 91

Ile Asp Glu Phe Phe Glu Glu Leu Ala Ile Arg Ile Cys Tyr Tyr Pro
1               5                   10                  15

Arg Ser Pro Gly Gly Phe Val Arg Phe Val Thr Ser Ile Arg Asn Ala
                20                  25                  30

Leu Gly Leu
        35

<210> SEQ ID NO 92
```

```
<211> LENGTH: 35
<212> TYPE: PRT
<213> ORGANISM: Herpesvirus

<400> SEQUENCE: 92

Arg Val Pro Ala Val Ala Trp Ile Gly Val Gly Ala Ile Val Gly Ala
 1               5                  10                  15

Phe Ala Leu Val Ala Ala Leu Val Leu Val Pro Pro Arg Ser Ser Trp
                20                  25                  30

Gly Leu Ser
        35

<210> SEQ ID NO 93
<211> LENGTH: 35
<212> TYPE: PRT
<213> ORGANISM: Herpesvirus

<400> SEQUENCE: 93

Gly Glu Leu Arg Ala Arg Glu Glu Ser Tyr Arg Thr Val Leu Ala Asn
 1               5                  10                  15

Phe Cys Ser Ala Leu Tyr Arg Tyr Leu Arg Ala Ser Val Arg Gln Leu
                20                  25                  30

His Arg Gln
        35

<210> SEQ ID NO 94
<211> LENGTH: 35
<212> TYPE: PRT
<213> ORGANISM: Herpesvirus

<400> SEQUENCE: 94

Ser Arg Gly Arg Thr Arg Asn Asn Tyr Gly Ser Thr Ile Glu Gly Leu
 1               5                  10                  15

Leu Asp Leu Pro Asp Asp Asp Ala Pro Ala Glu Ala Gly Leu Val
                20                  25                  30

Ala Pro Arg
        35

<210> SEQ ID NO 95
<211> LENGTH: 35
<212> TYPE: PRT
<213> ORGANISM: Herpesvirus

<400> SEQUENCE: 95

Asp Pro Ile Ile Gly Thr Ala Ala Ala Val Leu Glu Asn Leu Ala Thr
 1               5                  10                  15

Arg Leu Arg Pro Phe Leu Gln Cys Tyr Leu Lys Ala Arg Gly Leu Cys
                20                  25                  30

Gly Leu Asp
        35

<210> SEQ ID NO 96
<211> LENGTH: 35
<212> TYPE: PRT
<213> ORGANISM: Herpesvirus

<400> SEQUENCE: 96

Leu Asp Asp Leu Cys Ser Arg Arg Leu Ser Asp Ile Lys Asp Ile
 1               5                  10                  15

Ala Ser Phe Val Leu Val Ile Leu Ala Arg Leu Ala Asn Arg Val Glu
                20                  25                  30
```

```
Arg Gly Val
        35

<210> SEQ ID NO 97
<211> LENGTH: 35
<212> TYPE: PRT
<213> ORGANISM: Herpesvirus

<400> SEQUENCE: 97

Gly Val Ser Glu Ile Asp Tyr Thr Thr Val Gly Val Gly Ala Gly Glu
  1               5                  10                  15

Thr Met His Phe Tyr Ile Pro Gly Ala Cys Met Ala Gly Leu Ile Glu
                 20                  25                  30

Ile Leu Asp
        35

<210> SEQ ID NO 98
<211> LENGTH: 35
<212> TYPE: PRT
<213> ORGANISM: Herpesvirus

<400> SEQUENCE: 98

Ser Arg Arg Arg Leu Ser Asp Ile Lys Asp Ile Ala Ser Phe Val Leu
  1               5                  10                  15

Val Ile Leu Ala Arg Leu Ala Asn Arg Val Glu Arg Gly Val Ser Glu
                 20                  25                  30

Ile Asp Tyr
        35

<210> SEQ ID NO 99
<211> LENGTH: 35
<212> TYPE: PRT
<213> ORGANISM: Herpesvirus

<400> SEQUENCE: 99

Pro Leu Ile Arg Ser Gly Gly Phe Ala Val Pro Leu Ile Val Gly Gly
  1               5                  10                  15

Leu Cys Leu Met Ile Leu Gly Met Ala Cys Leu Leu Glu Val Leu Arg
                 20                  25                  30

Arg Leu Gly
        35

<210> SEQ ID NO 100
<211> LENGTH: 35
<212> TYPE: PRT
<213> ORGANISM: Herpesvirus

<400> SEQUENCE: 100

Arg Arg Arg Arg Arg Arg Thr Arg Cys Val Gly Leu Val Ile Ala Cys
  1               5                  10                  15

Leu Val Val Ala Leu Leu Ser Gly Gly Phe Gly Ala Leu Leu Val Trp
                 20                  25                  30

Leu Leu Arg
        35

<210> SEQ ID NO 101
<211> LENGTH: 35
<212> TYPE: PRT
<213> ORGANISM: Herpesvirus

<400> SEQUENCE: 101

Gly His His Val Ser Pro Gly Ser Pro Gly Phe Pro Glu Ser Pro Gly
```

-continued

```
                1               5                  10                 15
Asn Arg Glu Phe His Asp Leu Pro Glu Asn Pro Gly Ser Arg Ala Tyr
                               20                  25                 30

Pro Gly Thr
           35

<210> SEQ ID NO 102
<211> LENGTH: 35
<212> TYPE: PRT
<213> ORGANISM: Herpesvirus

<400> SEQUENCE: 102

Pro His His Ala Pro Ala Ala Pro Ser Asn Pro Gly Leu Ile Ile Gly
  1               5                  10                 15

Ala Leu Ala Gly Ser Thr Leu Ala Val Leu Val Ile Gly Gly Ile Ala
                 20                  25                 30

Phe Trp Val
           35
```

US 8,541,002 B2

VACCINE FOR TREATMENT AND PREVENTION OF HERPES SIMPLEX VIRUS INFECTION

RELATED APPLICATIONS

The application is a National Stage Application of PCT/US2004/029908, filed Sep. 13, 2004, which claims priority under 35 U.S.C. §119(e) to U.S. Provisional Application Ser. No. 60/503,148, entitled "VACCINE FOR TREATMENT AND PREVENTION OF HERPES SIMPLEX VIRUS INFECTION" filed on Sep. 12, 2003, which is herein incorporated by reference in its entirety.

1. INTRODUCTION

The present invention relates to methods and compositions for the prevention and treatment of herpes simplex virus infections.

2. BACKGROUND

2.1. Herpes Virus Infection and Vaccine

The herpesviruses include the herpes simplex viruses (HSV), comprising two closely related variants designated types 1 (HSV-1) and 2 (HSV-2). Primary HSV infections are seldom life threatening in healthy adults, but can have severe consequences in newborns whose mothers have had a primary infection during pregnancy. HSV-1 and HSV-2 are associated in some individuals with frequent and/or painful recurrences that manifest themselves as cold sores and genital herpes, respectively. HSV is a prevalent cause of genital infection in humans, with an estimated annual incidence of 600,000 new cases and with 10 to 20 million individuals experiencing symptomatic chronic recurrent disease. Although continuous administration of antiviral drugs such as acyclovir ameliorates the severity of acute HSV disease and reduces the frequency and duration of recurrent episodes, such chemotherapeutic intervention does not abort the establishment of latency nor does it alter the status of the latent virus. As a consequence, the recurrent disease pattern is rapidly reestablished upon cessation of drug treatment. Currently there exists no effective vaccine for the prevention or treatment of HSV-1 or HSV-2.

Most of the approaches for vaccination available today have been researched for the treatment of HSV infection. Traditional ways of preparing vaccines include the use of either inactivated or attenuated pathogens. A suitable inactivation of the pathogenic microorganism renders it harmless as a biological agent but does not destroy its immunogenicity. Injection of these "killed" particles into a host will then elicit an immune response capable of preventing a future infection with a live microorganism. However, a major concern in the use of inactivated pathogens as vaccines is the failure to inactivate all the microorganisms. Even when this is accomplished, since killed pathogens do not multiply in their host, or for other unknown reasons, the immunity achieved is often incomplete, short lived and requires multiple immunizations. Finally, the inactivation process may alter the microorganism's antigens, rendering them less effective as immunogens. Several HSV vaccines derived from inactivated virions have been evaluated clinically, and proven ineffective.

Attenuation refers to the production of strains of pathogenic microorganisms which have essentially lost their disease-producing ability. Attenuated pathogens often make good immunogens as they actually replicate in the host cell and elicit long lasting immunity However, several problems are encountered with the use of live vaccines, the most worrisome being insufficient attenuation and the risk of reversion to virulence. In addition, by using live vaccines for herpes viruses, latency may be established, and thus there is the potential for reactivation-associated or other chronic disease.

An alternative to the above methods is the use of subunit vaccines. This involves immunization only with those components which contain the relevant immunological material. Because of the risks associated with inactivated and attenuated pathogens, subunit vaccines containing purified viral proteins represent a relatively safe alternative. However, previous clinical experience with HSV subunit vaccines has not been encouraging. A recent phase III trial of an HSV-2 subunit vaccine developed by the Chiron Vaccine Study Group failed to prevent or delay outbreaks in infected individuals (Corey et al, Journal of the American Medical Association 282:331-340, 1999).

An effective vaccine that eliminates or decreases the transmission of HSV-1 and HSV-2 from infected to uninfected individuals would be highly desirable.

2.2. Use of Adjuvants in Vaccines

Vaccines are often formulated and inoculated with various adjuvants. The adjuvants aid in attaining a more durable and higher level of immunity using small amounts of antigen or fewer doses than if the immunogen were administered alone. Presently, aluminum salt-based ("alum") adjuvants are the only immunologic adjuvants used in U.S.-licensed vaccines. However, a variety of novel adjuvants which may be used to augment or replace alum in human vaccines has been under development and in preclinical and clinical evaluation for decades. Adjuvant mechanisms of action include increasing the biological or immunological half-life of vaccine antigens; improving antigen delivery to antigen presenting cells (APCs) and antigen processing and presentation by APCs; and inducing the production of immunomodulatory cytokines.

2.3. Heat Shock Proteins

Heat shock proteins (HSPs), also referred to as stress proteins, were first identified as proteins synthesized by cells in response to heat shock. HSPs have been classified into five families based on molecular weight: HSP100, HSP90, HSP70, HSP60, and smHSP. Many members of these families were found subsequently to be induced in response to other stressful stimuli including nutrient deprivation, metabolic disruption, oxygen radicals, and infection with intracellular pathogens (see Welch, May 1993, Scientific American 56-64; Young, 1990, Annu. Rev. Immunol. 8:401-420; Craig, 1993, Science 260:1902-1903; Gething et al., 1992, Nature 355:33-45; and Lindquist et al., 1988, Annu. Rev. Genetics 22:631-677). Members of the heat shock protein family include hsc70, hsp70, hsp90, hsp110, gp96, grp170, and calreticulin.

Studies on the cellular response to heat shock and other physiological stresses revealed that the HSPs are involved not only in cellular protection against these adverse conditions, but are also in essential biochemical and immunological processes in unstressed cells. HSPs accomplish different kinds of chaperoning functions. For example, members of the HSP70 family, located in the cell cytoplasm, nucleus, mitochondria, or endoplasmic reticulum (Lindquist et al., 1988, Ann. Rev. Genetics 22:631-677), are involved in the presentation of antigens to the cells of the immune system, and are also involved in the transfer, folding and assembly of proteins in normal cells. HSPs are capable of binding proteins or peptides, and releasing the bound proteins or peptides in the presence of adenosine triphosphate (ATP) or acidic conditions (Udono and Srivastava, 1993, J. Exp. Med. 178:1391-1396).

Srivastava et al. demonstrated immune response to methylcholanthrene-induced sarcomas of inbred mice (1988, Immunol. Today 9:78-83). In these studies, it was found that the molecules responsible for the individually distinct immunogenicity of these tumors were glycoproteins of 96 kDa (gp96) and intracellular proteins of 84 to 86 kDa (p84/86) (Srivastava et al., 1986, Proc. Natl. Acad. Sci. USA 83:3407-3411; Ullrich et al., 1986, Proc. Natl. Acad. Sci. USA 83:3121-3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava et al., 1988, Immunogenetics 28:205-207; Srivastava et al., 1991, Cum Top. Microbiol. Immunol. 167:109-123). Further, hsp70 was shown to elicit immunity to the tumor from which it was isolated but not to antigenically distinct tumors. However, hsp70 depleted of peptides was found to lose its immunogenic activity (Udono and Srivastava, 1993, J. Exp. Med. 178:1391-1396). These observations suggested that the heat shock proteins are not immunogenic per se, but form noncovalent complexes with antigenic peptides, and the complexes can elicit specific immunity to the antigenic peptides (Srivastava, 1993, Adv. Cancer Res. 62:153-177; Udono et al., 1994, J. Immunol., 152:5398-5403; Suto et al., 1995, Science 269:1585-1588).

Noncovalent complexes of HSPs and peptide, purified from cancer cells, can be used for the treatment and prevention of cancer and have been described in PCT publications WO 96/10411, dated Apr. 11, 1996, and WO 97/10001, dated Mar. 20, 1997 (U.S. Pat. No. 5,750,119 issued May 12, 1998, and U.S. Pat. No. 5,837,251 issued Nov. 17, 1998, respectively, each of which is incorporated by reference herein in its entirety). The isolation and purification of HSP-peptide complexes has been described, for example, from pathogen-infected cells, and used for the treatment and prevention of infection caused by the pathogen, such as viruses, and other intracellular pathogens, including bacteria, protozoa, fungi and parasites (see, for example, PCT Publication WO 95/24923, dated Sep. 21, 1995). Immunogenic stress protein-antigen complexes can also be prepared by in vitro complexing of stress protein and antigenic peptides, and the uses of such complexes for the treatment and prevention of cancer and infectious diseases has been described in PCT publication WO 97/10000, dated Mar. 20, 1997 (U.S. Pat. No. 6,030,618 issued Feb. 29, 2000). The use of stress protein-antigen complexes for sensitizing antigen presenting cells in vitro for use in adoptive immunotherapy is described in PCT publication WO 97/10002, dated Mar. 20, 1997 (see also U.S. Pat. No. 5,985,270 issued Nov. 16, 1999).

3. SUMMARY OF THE INVENTION

The present invention relates to antigenic peptides of herpesviruses, and to methods of use of such antigenic peptides in the treatment and prevention of infections by herpesviruses, herpes simplex viruses (HSV) type I and II particularly. The present invention provides pharmaceutical compositions comprising antigenic peptides of the infectious agent, and adjuvants, which are able to stimulate an immune response in an animal against the infectious agent and cells infected with the infectious agent. The present invention also provides methods of preparation of the pharmaceutical compositions of the invention.

The invention encompasses compositions comprising one or more antigenic peptides, and compositions comprising antigenic peptides combined with or complexed with adjuvants. Preferably, the antigenic peptides are complexed to stress proteins. The invention further provides pharmaceutical compositions comprising antigenic peptides combined with or complexed with adjuvants, and a pharmaceutically acceptable carrier or excipient.

In one embodiment, the antigenic peptides of the invention comprise amino acid sequences of viral proteins expressed and/or displayed by HSV-2. The amino acid sequences of 102 herpesvirus peptides selected by the inventors are assigned SEQ ID NO: 1 through to SEQ ID NO: 102. These 102 herpesvirus peptides, each consisting of 35 amino acids, are selected on the basis of predictions on the numb& and quality of HLA-binding epitopes present in each of the peptides. Also provided by the invention are variations and fragments of these herpesvirus peptides which comprise one or more of the predicted epitopes present in these peptides. Variations of such herpesvirus peptides include the addition of a heterologous high affinity heat shock protein binding sequence, and optionally a peptide linker.

The invention also provides compositions comprising a mixture of two or more different antigenic peptides; preferably, the antigenic peptides are purified. In various embodiments, the mixture comprises a plurality of different antigenic peptides, wherein only HLA-binding epitopes from one of the 102 herpesvirus peptides or from a selected subset of herpesvirus peptides are present in the antigenic peptides. In a preferred embodiment, a mixture of a plurality of antigenic peptides comprises epitopes that are present only in the herpesvirus peptides having SEQ ID NOs: 1 to 49.

In a composition comprising a mixture of different antigenic peptides, the different antigenic peptides can be present in any proportion relative to each other by weight or by molar amounts. In a specific embodiment, the antigenic peptides of the mixture are present in approximately equal proportions by weight or by molar amounts.

In another embodiment, the invention provides compositions comprising antigenic peptides mixed with or complexed with adjuvants. Depending on the adjuvant and the method applied, an antigenic peptide of the invention can form a covalent or non-covalent molecular complex with an adjuvant. Alternatively, the antigenic peptides can be mixed with an adjuvant in the same composition without requiring the formation of any complex. In a preferred embodiment, the antigenic peptides are complexed with heat shock proteins such as members of the heat shock protein families of HSP60, HSP70, HSP90, HSP100, and sHSPs. In preferred embodiments of the invention, the adjuvant is a stress protein chosen from the group consisting of hsc70, hsp70, hsp90, hsp110, gp96, grp170, and calreticulin. In one specific embodiment, the complexes comprise hsc70 non-covalently complexed to the antigenic peptides, preferably a plurality of different antigenic peptides. In another specific embodiment, the complexes comprise hsp70 non-covalently complexed to the antigenic peptides, preferably a plurality of different antigenic peptides. In another specific embodiment, the complexes comprise hsp70 covalently complexed to the antigenic peptides, for example, by crosslinking with glutaraldehyde or ultraviolet light. In other embodiments, the complexes comprise peptide-binding fragments of heat shock proteins, or functionally active variants, analogs or derivatives of heat shock proteins complexed to the antigenic peptides.

Accordingly, in one embodiment, the invention provides a composition comprising an adjuvant and a plurality of different antigenic peptides, wherein said different antigenic peptides each comprises at least one HLA-binding epitope that is present in a herpesvirus peptide, where the amino acid sequence of said herpesvirus peptide is selected from the group consisting of SEQ ID NO: 1 to 102.

In another embodiment, the invention provides a composition comprising complexes of a stress protein bound to an antigenic peptide, wherein said complexes differ in the sequence of the antigenic peptide, wherein each antigenic peptide comprises at least one HLA-binding epitope that is present in a herpesvirus peptide, the amino acid sequence of said herpesvirus peptide selected from the group consisting of SEQ ID NO: 1 to 102. In a specific embodiment, each antigenic peptide comprises at least one HLA-binding epitope of a different herpesvirus peptide selected from among herpesvirus peptides differing in amino acid sequence, the amino acid sequence of each herpesvirus peptide selected from the group consisting of SEQ ID NO: 1 to 102. The number of different antigenic peptides present in a composition of the invention can vary from 2, 3, 4, 5, 10, 15, 20, 25, 30, 35, 40, 45, 49, 50, 55, 60, 65, 70, 75, 80, 85, 90, 95, 100, to 102, or it can be any integer between 2 and 102. Preferably, a plurality of different antigenic peptides are complexed to the stress protein.

In a preferred embodiment, the invention provides a composition comprising 49 different complexes of a stress protein, noncovalently or covalently, bound to an antigenic peptide, wherein said different complexes each comprises a different antigenic peptide, said different antigenic peptide each comprising one or more HLA-binding epitopes of a single herpesvirus peptide, said herpesvirus peptide consisting of an amino acid sequence selected from the group consisting of SEQ ID NO: 1 to 49.

In another embodiment, the compositions of the invention comprise a number of different complexes of a stress protein bound to an antigenic peptide, wherein said different complexes each comprises a different antigenic peptide, wherein each one of said different antigenic peptide comprises one or more HLA-binding epitope of one of a selection of herpesvirus peptides.

In a more preferred embodiment, the compositions of the invention comprise 49 different complexes of a stress protein bound to an antigenic peptide, wherein said 49 different complexes each comprises a different antigenic peptide, wherein each one of said different antigenic peptide comprises at least one HLA-binding epitope of a different herpesvirus peptide selected from among herpesvirus peptides differing in amino acid sequence, the amino acid sequence of each herpesvirus peptide selected from the group consisting of SEQ ID NO: 1 to 49.

In another preferred embodiment, the compositions of the invention comprise different complexes of a stress protein bound to a herpesvirus peptide consisting of an amino acid sequence selected from the group consisting of SEQ ID NO: 1 to 102.

In another preferred embodiment, the compositions of the invention comprise 49 different complexes of a stress protein, noncovalently or covalently bound to a herpesvirus peptide, wherein said stress proteins in said complexes are bound to each of the herpesvirus peptides consisting of an amino acid sequence selected from the group consisting of SEQ ID NO: 1 to 49.

In yet another embodiment, the invention encompasses compositions prepared by a method comprising complexing in vitro stress proteins with a plurality of different antigenic peptides, wherein said different antigenic peptides each comprises at least one HLA-binding epitope that is present in a single herpesvirus peptide, the amino acid sequence of the herpesvirus peptide selected from the group consisting of SEQ ID NO: 1 to 102.

In a preferred embodiment, the invention provides compositions prepared by complexing in vitro stress proteins with 49 different antigenic peptides, wherein each one of said 49 different antigenic peptides comprises one or more HLA-binding epitopes of a different herpesvirus peptide selected from among herpesvirus peptides differing in amino acid sequence, the amino acid sequence of each herpesvirus peptide selected from the group consisting of SEQ ID NO: 1 to 49. Such complexes may be prepared, e.g., by complexing a purified HSP or a plurality of different HSPs to one species of antigenic peptide and mixing the individual HSP-peptide complexes together. Such complexes may alternatively be prepared by complexing a purified HSP or a plurality of different HSPs to two or more different antigenic peptides in a mixture.

In a more preferred embodiment, the compositions of the invention is prepared by a method comprising the steps of complexing in vitro a stress protein with 49 different herpesvirus peptides consisting of an amino acid sequence selected from the group consisting of SEQ ID NO: 1 to 49.

In various embodiments, the antigenic peptides may comprise a heterologous high affinity heat shock protein binding sequence.

The invention provides pharmaceutical compositions comprising, in a physiologically acceptable carrier, one or more of the different antigenic peptides of the invention and an adjuvant such as an immunostimulatory nucleotide or a saponin (e.g., QS21). In a preferred embodiment, the pharmaceutical composition comprises hsp70 complexed with a plurality of different antigenic peptides of the invention, and QS21. In another preferred embodiment, the pharmaceutical composition comprises hsp70 complexed with one or more different antigenic peptides of the invention, and at least one immunostimulatory oligonucleotide. In a most preferred embodiment, the pharmaceutical composition comprises hsp70 complexed with one or more different antigenic peptides of the invention, QS21, and at least one immunostimulatory oligonucleotide.

The invention provides methods for preparing compositions comprising the antigenic peptides, mixtures of peptides and adjuvants, or peptide-adjuvant complexes described supra. In one embodiment, such a method relates to preparation of a composition for eliciting in a mammal an immune response against HSV-1 or HSV-2, the method comprising complexing in vitro one or more of the antigenic peptides with a stress protein and combining the peptide-stress protein complexes with a pharmaceutically acceptable carrier, thereby generating a noncovalent stress protein-peptide complex. In a specific embodiment, the one or more different antigenic peptides are each produced by chemical synthesis. In another embodiment, the peptides are combined with the one or more adjuvants by covalent complex formation. In another embodiment, the different peptides are combined with the one or more adjuvants by noncovalent complex formation. The invention also provides compositions comprising the pharmaceutical composition and a second treatment modality, such as an additional adjuvant, an antiviral agent, or a biological response modifier. In a further specific embodiment, the antiviral agent is chosen from the group consisting of acyclovir, valacyclovir, pencyclovir, famcyclovir, cidofovir, and phosphonoformic acid. The biological response modifier is selected from the group consisting of α-interferon, γ-interferon, interleukin-2, interleukin-4, interleukin-6, tumor necrosis factor and combinations thereof.

The invention further encompasses kits for use in the treatment or prevention of herpesvirus infection.

In a different aspect of the invention, a method of eliciting an immune response against HSV-1 or HSV-2 in an individual is provided. The method comprises administering to the individual an effective amount of an immunogenic complex comprising at least one of the antigenic peptides described supra and at least one adjuvant. The invention also provides methods for treatment or prevention of infection by a herpesvirus and of any disease caused by a herpesvirus. The methods comprise the step of administering to the individual an immunogenic amount of a pharmaceutical composition comprising one or more of the antigenic peptides of the invention, or antigenic peptides and one or more adjuvants, in a physiologically acceptable carrier.

In a related embodiment, the methods are used for preventing an infectious disease caused by a herpesvirus in an individual for whom preventing such an infectious disease is desired. In another related embodiment, the methods are used for treating an infectious disease caused by a herpesvirus in an individual. In a specific embodiment of this method, the infectious disease is caused by HSV-1 or HSV-2.

The invention further encompasses methods for reducing the severity of disease associated with primary HSV infection, reducing the frequency of reactivation of latent HSV virus, limiting the severity of reactivated disease, or restricting the transmission of virus associated with either primary or reactivated infection, comprising the step of administering to the individual an effective amount of an immunogenic pharmaceutical composition comprising one or more of the antigenic peptides described supra and one or more adjuvants in a physiologically acceptable carrier. The methods of the invention can also be used in inhibiting HSV-1 or HSV-2 replication in an individual. In various embodiments, the therapeutic methods are repeated until the symptoms are alleviated.

In various embodiments, the adjuvant that is present in the composition include but is not limited to a stress protein, a saponin, or at least one immunostimulatory nucleotide. In another embodiment of the method, the heat shock protein is non-covalently complexed to at least one antigenic peptide, and the heat shock protein is selected from the group consisting of hsc70, hsp70, hsp90, hsp110, gp96, grp170, calreticulin, and compositions thereof.

In other embodiments of the invention, antigenic peptide-adjuvant complexes are formed in vitro by incubating at least one antigenic peptide with at least one heat shock protein under conditions and for a period of time sufficient for the formation of the complexes.

4. BRIEF DESCRIPTION OF THE DRAWINGS

FIG. 1A, B. Complexes of the 49 herpesvirus peptides and hsp70 are immunogenic. FIG. 1A. Splenocytes derived from mice treated with a pharmaceutical composition comprising complexes of hsp70 and the 49 herpesvirus peptides produced approximately 140 spot forming cells (SFCs) per $10^6$ splenocytes following stimulation of cultured splenocytes in vitro. Splenocytes derived from mice treated with hsp70 without the 49 peptides produced fewer than 5 SFCs per $10^6$ splenocytes. Splenocytes derived from mice treated with the 49 peptides without hsp70 produced less than 60 SFCs per $10^6$ splenocytes. FIG. 1B. Addition of adjuvant increases this immune response to complexes of the 49 herpesvirus peptides and hsp70. Splenocytes derived from mice treated with a pharmaceutical composition comprising the complexes of hsp70 and the 49 herpesvirus peptides plus QS21 produced approximately 450 SFCs per $10^6$ splenocytes. Splenocytes derived from mice treated with hsp70 without the 49 peptides produced fewer than 5 SFCs per $10^6$ splenocytes. Splenocytes derived from mice treated with the 49 peptides without hsp70 produced over 250 SFCs per $10^6$ splenocytes.

Figure 2:
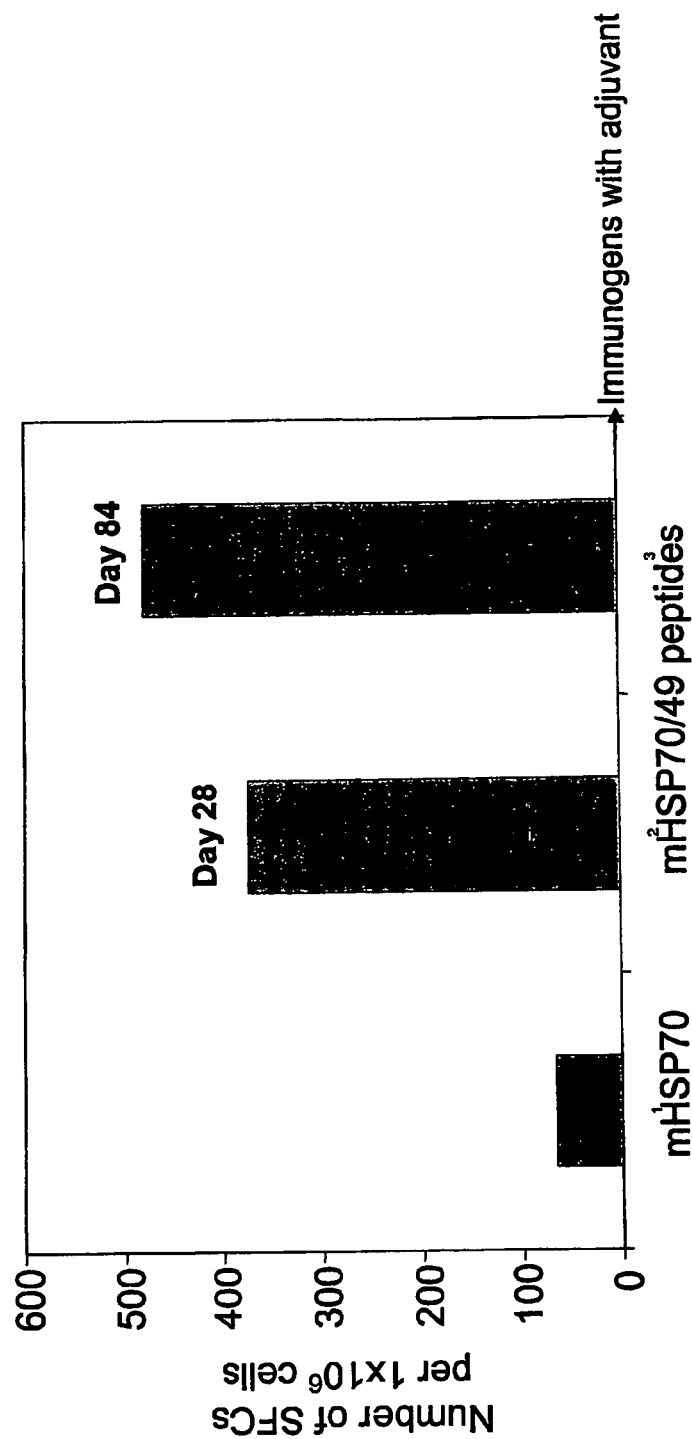

FIG. 2. Immune response obtained with complexes of the 49 herpesvirus peptides and hsp70 is long-lasting. Splenocytes from mice immunized on day 0 and day 14 with a pharmaceutical composition comprising complexes of the 49 herpesvirus peptides and hsp70 complexes plus adjuvant were harvested on days 28 and 84. These splenocytes produced nearly 400 SFCs per $10^6$ splenocytes when harvested at day 28, and nearly 500 SFCs per $10^6$ splenocytes when harvested at day 84. In contrast, splenocytes from mice immunized with hsp70 plus adjuvant alone produced background level of SFCs on day 42.

FIG. 3A-D. Complexes of hsp70 and HSV antigenic peptides protect mice from HSV infection in vivo. Female Swiss Webster mice were immunized i.d. on Day 0, 7 and 14 with the following formulations: (1) GP/CFA, total glycoprotein from HSV-2 infected cell lysates formulated in Freund's adjuvant (Freund's complete adjuvant for the 1st immunization, thereafter Freund's incomplete adjuvant was used) as an immunization positive control; (2) Saline/CFA, Freund's adjuvant formulated with placebo, immunization negative control; (3) mouse HSP70 (mHSP70), 100 µg per dose of mHSP70; (4) QS-21, 10 µg per dose of QS-21; (5) 49 HSV-2 peptides/QS-21, 5.5 µg of the 49 HSV-2 peptides (equivalent to the amount in the complex preparations)+10 µg per dose of QS-21; or (6) mHSP70/49 HSV-2 peptides/QS-21, 100 µg per dose of mHSP70 complexed to 49 HSV-2 peptides (at 1:1 mHSP70 to total peptide molar ratio)+10 µg per dose of QS-21. Mice were treated with depo-provera to synchronize their estrus cycles, and on day 28 were challenged intravaginally with $5 \times 10^5$ pfu of HSV-2 (strain 186). HSV-2 induced disease and mortality were evaluated up to day 49 following initial vaccination. FIG. 3A. Survival (Kaplan-Meier's) curves (Kaplan and Meier, *J Am Stat Assoc.* 50, 457-481, 1958) for GP/CFA ("Glycoproteins/CFA Control"), Saline/CFA ("Mock/CFA Control"), and QS-21 ("Adjuvant") control groups. FIG. 3B. Survival (Kaplan-Meier's) curves (Kaplan and Meier, *J Am Stat Assoc.* 50, 457-481, 1958) for mHSP70, 49 HSV-2 peptides/QS-21 ("49 peptides+adjuvant"), and mHSP70/49 HSV-2 peptides/QS-21 ("mHSP/49 Peptides+adjuvant") groups. Arrow indicates curve with significant difference (P<0.05) by Log-Rank analysis, compared to Saline/CFA (negative control) group. FIG. 3C. Hair loss and erythema (skin redness) development in GP/CFA ("Glycoproteins/CFA Control"), Saline/CFA ("Mock/CFA Control"), and QS-21 ("Adjuvant") control groups. FIG. 3D: Hair loss and erythema (skin redness) development in mHSP70, 49 HSV-2 peptides/QS-21 ("49 peptides+adjuvant"), and mHSP70/49 HSV-2 peptides/QS-21 ("mHSP/49 Peptides+adjuvant") groups. Arrow indicates curves with significant difference (P<0.05) by Log-Rank analysis, compared to Saline/CFA group.

5. DETAILED DESCRIPTION OF THE INVENTION

The present invention relates to pharmaceutical compositions for the treatment and prevention of infectious diseases, in particular infections by herpes simplex viruses (HSV). The pharmaceutical compositions of the invention comprise antigenic peptides of infectious agents, and adjuvants, which are able to stimulate an immune response in an animal against the antigenic peptides of infectious agents. The present invention provides methods of preparation of the pharmaceutical compositions of the invention. The present invention also encompasses methods of use of the pharmaceutical compositions in the treatment and prevention of infections by HSV, including type 1 and type 2 herpes simplex viruses (HSV-1 and HSV-2).

The invention is based on the inventors' selection of antigenic peptides and adjuvants, and the methods by which antigenic peptides and adjuvants are combined and/or complexed to form pharmaceutical compositions. Without being bound by any theory or mechanisms, due to the multivalent nature of the pharmaceutical compositions of the invention and the use of adjuvants that are efficient in antigen presentation, the immune response elicited in a subject against an infectious agent is far more effective than that produced by traditional subunit vaccines.

The invention provides compositions comprising one or more antigenic peptides, compositions comprising antigenic peptides combined with or complexed with adjuvants. Preferably, the antigenic peptides are complexed to heat shock proteins. The invention further provides pharmaceutical compositions comprising antigenic peptides combined with or complexed with adjuvants, and a pharmaceutically acceptable carrier or excipient.

In one embodiment, the antigenic peptides of the invention comprise amino acid sequences of viral proteins expressed and/or displayed by HSV-2. The amino acid sequences of 102 herpesvirus peptides selected by the inventors are assigned SEQ ID NO: 1 through to 102 and are listed in Table 1. These 102 herpesvirus peptides each consists of 35 amino acids. The herpesvirus peptides are selected on the basis of predictions on the number and quality of HLA-binding epitopes present in each of the peptides. Also provided by the invention are variations and fragments of these herpesvirus peptides which comprise one or more of the predicted epitopes in these viral peptides. As used herein, the term "antigenic peptide of the invention" refers to any one of the 102 herpesvirus peptides listed in Table 1 as well as variants and fragments of these herpesvirus peptides that comprise one or more HLA-binding epitopes of the respective herpesvirus peptide. Preferably, an antigenic peptide of the invention comprises only a portion of and not the entire amino acid sequence of a herpes simplex virus type 2 protein from which the herpesvirus peptide of the invention is derived. The amino acid sequence of the herpes simplex virus type 2 protein from which each herpesvirus peptide of the invention is derived is identified by its Genbank accession number shown in Table 1.

The antigenic peptides of the invention can be obtained from natural sources, or produced by chemical synthesis or recombinant DNA technology. Preferably, the antigenic peptides of the invention are purified. Purified antigenic peptides are substantially free of materials that are associated with the peptides in a virus, in a cell, in a cell extract, in a cell culture medium, in an individual, or in a reaction mixture of a peptide synthesis reaction. Nucleotide sequences encoding antigenic peptides of the invention, vectors comprising such nucleotide sequences, and expression vectors comprising such nucleotide sequences, are also encompassed. The invention also encompasses recombinant cells comprising nucleotide sequence(s) encoding one or more different antigenic peptides of the invention, wherein the nucleotide sequence(s) are operatively linked to at least one promoter which facilitates expression of the nucleotide sequence(s) in the cells, resulting in the production of the antigenic peptide(s) of the invention.

The invention also provides compositions comprising a mixture of the antigenic peptides of the invention. In various embodiments, the mixture comprises two or more different antigenic peptides of the invention. The mixture can comprise at least 2, 10, 20, 30, 40, 49, 75, or 100 different antigenic peptides, preferably purified antigenic peptides. In various embodiments, the mixture comprises a plurality of different antigenic peptides, wherein only epitopes from one of the 102 herpesvirus peptides or from a selected subset of the 102 herpesvirus peptides are present in the antigenic peptides. In a preferred embodiment, each of the different antigenic peptides in the mixture comprises one or more HLA-binding epitopes that are present in the herpesvirus peptides, the amino acid sequences of which are assigned SEQ ID NOs: 1 to 49.

In various embodiments, each antigenic peptide in a plurality of antigenic peptides does not contain amino acid sequences that are contiguous with the amino acid sequence of any one of the 102 herpesvirus peptide.

In various embodiments, the plurality of antigenic peptides do not include antigenic peptides comprising epitope(s) of HSV2 proteins other than those comprising the amino acid sequence of SEQ ID NO: 1 to 102, or SEQ ID NO: 1 to 49.

In a specific embodiment, the plurality of antigenic peptides are not obtained or purified from a cell or virus.

In various embodiments, at least 10%, 20%, 30%, 40%, 50%, 60%, 70%, 80%, 90%, or 95% of the antigenic peptides in the plurality of antigenic peptides are different herpesvirus peptides selected from the group consisting of SEQ ID NO: 1 to 102 or SEQ ID NO: 1 to 49.

In a composition comprising a mixture of different antigenic peptides, the different antigenic peptides can be present in any proportion relative to each other by weight or by molar amounts. In a specific embodiment, the antigenic peptides of the mixture are present in approximately equal proportions by weight or by molar amounts.

In another embodiment, the invention provides compositions comprising one or more antigenic peptides mixed with or complexed with adjuvants. Depending on the adjuvant and the method applied, an antigenic peptide of the invention can form a covalent or non-covalent molecular complex with an adjuvant. Alternatively, the antigenic peptides can be mixed with an adjuvant in the same composition without requiring the formation of any complex. Suitable adjuvants for use in various embodiments of the present invention are described in section 5.2 hereinbelow.

In a preferred embodiment, the antigenic peptides of the invention are complexed non-covalently with heat shock proteins including but not limited to members of the following heat shock protein families: Hsp60, Hsp70, Hsp90, Hsp100, and sHSPs. The term "heat shock protein" is used herein synonymously with the term "stress protein." In preferred embodiments, the adjuvant is chosen from the group of heat shock proteins consisting of hsp70, hsc70, hsp90, gp96, calreticulin, hsp110, grp170, and combinations of two or more of the foregoing. In a most preferred embodiment, the adjuvant complexed to the antigenic peptides is hsp70 or hsc70 (Genbank accession number Y00371). In other embodiments, a peptide-binding fragment of a heat shock protein is used to form complexes with the antigenic peptides.

In an alternative embodiment, the complexes are covalent molecular complexes comprising antigenic peptides and heat shock proteins. Preferably, the heat shock protein is hsp70. The covalent complex can be formed by techniques known in the art such as crosslinking with glutaraldehyde or ultraviolet light.

In certain embodiments, the composition comprises complexes of different stress proteins and different antigenic peptides. For example, the composition comprises a mixture of hsp70 and hsc70 complexed with a plurality of different antigenic peptides.

The invention also provides methods for preparing compositions of the invention containing antigenic peptides and adjuvants. In a preferred embodiment, the method comprises complexing in vitro one or more different antigenic peptides with a heat shock protein, thereby generating a population of immunogenic noncovalent HSP-peptide complexes.

In yet another embodiment, a fusion protein comprising a proteinaceous adjuvant, such as a stress protein, and an antigenic peptide is contemplated. Such a fusion protein can be produced by recombinant DNA techniques well known in the art (see, e.g., U.S. Pat. No. 6,524,825, which is incorporated by reference herein in its entirety). For example, a nucleic acid encoding a stress protein can be joined to either end of a nucleic acid sequence encoding the antigenic peptide such that the two protein-coding sequences are sharing a common translational reading frame. The joined nucleic acid sequences are inserted into an appropriate vector selected based on the expression features desired and the nature of the host cell. Following expression in host cells, the fusion protein can be purified by routine biochemical separation techniques or by immunoaffinity methods using an antibody to a part of the fusion protein. Alternatively, the selected vector can add a tag to the fusion protein sequence, e.g., an oligohistidine tag, permitting expression of a tagged fusion protein that can be purified by affinity methods using an antibody or other material having an appropriately high affinity for the tag. Sambrook et al., Molecular Cloning: A Laboratory Manual, 2d Ed., Cold Spring Harbor Laboratory Press (1989); Deutscher, M., Guide to Protein Purification Methods Enzymology, vol. 182, Academic Press, Inc., San Diego, Calif. (1990). A fusion protein can also be prepared chemically.

In an additional embodiment, the fusion protein further comprises a moiety to target the fusion protein to antigen presenting cells. Many such targeting moiety is well known in the art and can be used to form a fusion protein with the antigenic peptide.

In various embodiments, the invention provides pharmaceutical compositions comprising antigenic peptides, adjuvants, and a physiologically acceptable carrier. In specific embodiments, the invention further provides pharmaceutical compositions comprising an immunogenic amount of antigenic peptides and adjuvants, said amount being effective in eliciting an immune response against one of the antigenic peptides and/or herpes simplex viruses in a subject.

The invention also provides methods for treatment or prevention of viral diseases in a subject caused by herpes simplex viruses, preferably by HSV-1 or HSV-2. One embodiment provides a method of treating or preventing such an infectious disease in a subject having such an infectious disease or in whom preventing such an infectious disease is desired, comprising the step of administering to the individual an effective amount of a pharmaceutical composition of the invention comprising a plurality of antigenic peptides, or a plurality of antigenic peptides and adjuvants, in a physiologically acceptable carrier. Preferably, the subject is a mammal, and most preferably a human. In a less preferred embodiment, the adjuvant in a separate composition is administered to the subject sequentially or simultaneously with the administration of the antigenic peptides. In various embodiments of the invention, the administration is parenteral, intravenous, intradermal, transdermal, mucosal or oral. The methods of the invention can also be used for reducing the severity of disease associated with primary HSV infection, reducing the frequency of reactivation of latent HSV virus, limiting the severity of reactivated disease, or restricting the transmission of virus associated with either primary or reactivated infection. In yet another embodiment, the composition is administered to a subject for stimulating in said subject a cytotoxic T cell response against HSV-1 and/or HSV-2. The method can be repeated until the symptoms are alleviated.

In a further embodiment, the pharmaceutical compositions of the invention can be used in combination with one or more other treatment modalities. For example, such treatment modalities include but are not limited to, chemotherapeutic agents such as antiviral agents, antibodies, adjuvants, biological response modifiers, etc. In a preferred embodiment, the antiviral agent is chosen from the group consisting of acyclovir, valacyclovir, pencyclovir, famcyclovir, cidofovir, and phosphonoformic acid.

The invention further encompasses kits for the treatment or prevention of HSV infections.

5.1. Antigenic Peptides

The present invention provides antigenic peptides that comprise amino acid sequences of viral proteins expressed and/or displayed by HSV-2, especially upon infection of host cells. These antigenic peptides can be prepared synthetically, or by recombinant DNA technology, or isolated from natural sources such as whole viruses. The antigenic peptides of the invention can be used in combination with adjuvants of the invention to create pharmaceutical compositions that are useful for treatment and/or prevention of HSV infections. Pharmaceutical compositions comprising the antigenic peptides of the invention are immunogenic and are effective at eliciting a beneficial immune response in a subject.

In one embodiment of the invention, the amino acid sequences of 102 herpesvirus peptides selected by the inventors assigned SEQ ID NO: 1-102 are listed in Table 1. Each of the herpesvirus peptides consists of 35 amino acids and comprises multiple epitopes which are predicted to be present on the corresponding HSV-2 protein. Table 1 lists the protein from which each herpesvirus peptide is derived and the position of the antigenic peptide within the viral protein. Table 1 further lists predicted immunogenic HLA-binding epitopes found within each peptide sequence. Amino acid positions for these epitopes are numbered from the first amino acid in the peptide sequence. For example, peptide RL02-1, encoded by SEQ ID NO:1, has a predicted HLA-B702 binding epitope at residues 2-10. This indicates that for the amino acid sequence of RL02-01, residues NPRTAPRSL out of the total amino acid sequence of RL02-01 (G NPRTAPRSLSLGGHTVRALSPTPPWPGTDDEDDD) is predicted to bind HLA-B702.

Since the proteins of HSV-2 and HSV-1 are highly homologous, many of the epitopes displayed by the herpesvirus peptides of the invention are shared by HSV-1. Accordingly, the pharmaceutical compositions are useful for treatment and/or prevention of HSV-2 as well as HSV-1 infections. As used herein, an "epitope" refers to a region of an antigenic peptide that binds or that is predicted to bind an antibody or major histocompatibility (MHC) molecule of a subject. Preferably, the epitope, upon binding to the MHC molecule, stimulates in vivo an immune response to the antigenic peptide. The peptides of the present invention contain epitopes that are predicted to be capable of binding selected MHC molecules and inducing an immune response. The antigenic peptide epitopes of the invention comprise conserved residues involved in binding proteins encoded by MHC alleles. The antigenic peptide epitopes predicted to bind MHC class I molecules are typically between 8 to 10 residues, while antigenic peptide epitopes predicted to bind MHC class II molecules are typically in the range of 10 to 20 residues.

MHC molecules are classified as either Class I or Class II molecules. Class II MHC molecules are expressed primarily on cells involved in initiating and sustaining immune responses, such as dendritic cells, B lymphocytes, macrophages, etc. Class II MHC molecules are recognized by helper T lymphocytes and induce proliferation of helper T lymphocytes and amplification of the immune response to the particular immunogenic peptide that is displayed. Class I MHC molecules are expressed on almost all nucleated cells and are recognized by cytotoxic T lymphocytes (CTLs), which then destroy the antigen-bearing cells. Cytotoxic T lymphocytes are particularly important in tumor rejection and in fighting viral infections. The CTL recognizes the antigen in the form of a peptide fragment bound to the MHC class I molecules rather than the intact foreign antigen itself. Specific human MHC alleles predicted to bind the antigenic peptides of the invention are listed in Table 1 and include the following Human Leukocyte Antigen (HLA) molecules: HLA-A1, HLA-A201, HLA-A203, HLA-A3, HLA-A2402, HLA-A26, HLA-B702, HLA-B8, HLA-B1510, HLA-B2705, HLA-B2709, HLA-B4402, and HLA-B5101 (Rammensee, et al., Immunogenetics 41, 178-228, 1995). The capacity to bind MHC molecules can be measured in a variety of different ways, such as by inhibition of antigen presentation (Sette, et al., J. Immunol. 141:3893, 1991), in vitro assembly assays (Townsend, et al., Cell 62:285, 1990), and FACS based assays using mutated cells, such as RMA.S (Melief, et al., Eur. J. Immunol. 21:2963, 1991).

As used herein, the term "HLA-binding epitope/epitopes" refers to those epitopes shown to bind an HLA molecule by any of the above assays, or predicted to bind an HLA molecule by a software program (e.g. SYFPEITHI, Rammensee, et al., Immunogenetics 50, 213-219, 1999). Other methods that can be used include those disclosed in Guan, P. et al., (2003) Applied Bioinformatics, 2: 63-66; Blythe, M. J. et al., (2002) Bioinformatics, 18: 434-439; Flower, D. R. and Doytchinova, I. A. (2002). Applied Bioinformatics, 1: 167-176; Yu, K. et al., (2002) Molecular Medicine, 8: 137-48; Brusic, V. et al., (2002) Immunology and Cell Biology, 80: 280-285; Jung, G. et al., (2001) *Biologicals*, 29: 179-181 (describes T cell epitope prediction programme EPIPREDICT); Kwok, W. W. et al., (2001) Trends in Immunology, 22: 583-588; Mallios, R. R. (2001) Bioinformatics, 17: 942-948; Römisch, K. (2001). Trends in Biochemical Sciences, 26: 531; Schirle, M. et al., (2001) Journal of Immunological Methods, 257: 1-16; Singh, H. and Raghava, G. P. S. (2001) Bioinformatics, 17: 1236-1237; Andersen, M. H. et al., (2000) Tissue Antigens, 55: 519-531; Buus, S. (1999). Current Opinion in Immunology, 11: 209-213; Mallios, R. R. (1999) Bioinformatics, 15: 432-439; and Maffei, A. and Harris, P. E. (1998). Peptides, 19: 179-198;

In one embodiment, the invention encompasses antigenic peptides consisting essentially of the amino acid sequence of any one of SEQ ID NOS: 1-102. The peptides can also be modified by the addition or deletion of amino acids. For example, several (1, 2, 3, 4, or 5) additional amino acid residues can be added to or removed from either end or each ends of the herpesvirus peptide providing that the antigenicity or immunogenicity of the antigenic peptide is not destroyed. The peptides of the invention can also be modified by altering the order or composition of certain residues, for example, residues that are located within a HLA-binding epitope. It can readily be appreciated that certain amino acid residues essential for binding to MHC molecules, e.g., those at critical contact sites or conserved residues in an epitope may generally not be altered without an adverse effect on immunogenic activity.

In another embodiment, the invention encompasses antigenic peptides, each comprising a fragment of any of SEQ ID NOS: 1-102, wherein the fragment comprises at least one epitope present in any one of SEQ ID NOS: 1-102. Preferably, the fragment comprises 2, 3, 4, 5, 6, 7, 8, 9, 10 or more epitopes present in any of the SEQ ID NOS: 1-102. Most preferably, an antigenic peptide comprises HLA-binding epitopes that are present in only one of the herpesvirus peptides assigned SEQ ID NOS: 1-102. Typically, an epitope present in a herpesvirus peptide consists essentially of a sequence of between 8 to 10 amino acids. Epitopes present in the herpesvirus peptides of the invention may overlap each other. Accordingly, an antigenic peptide of the invention comprises a fragment of any one of SEQ ID NOS. 1-102 that is at a minimum eight-amino acid long and that can be up to thirty four-amino acids long. Fragments of herpesvirus peptides of intermediate length, i.e., consisting of 9, 10, 11, 12, 13, 14, 15, 16, 17, 18, 19, 20, 21, 22, 23, 24, 25, 26, 27, 28, 29, 30, 31, 32, or 33 amino acids are also encompassed.

In yet another embodiment, the invention provides antigenic peptides that are variants of the viral peptides, wherein the amino acid sequence of an antigenic peptide is at least 50%, 60%, 70%, or 80% similar to one of SEQ ID NOS: 1-102. Preferably, the similarity is 90% and most preferably 95% or higher. Preferably, the variant comprises 2, 3, 4, 5, 6, 7, 8, 9, 10 or more epitopes present in any of the SEQ ID NOS: 1-102. Preferably, the variants comprise mostly or only conservative substitutions of amino acids relative to the amino acid sequence of SEQ ID NO: 1-102. Preferably few if any of the amino acid substitutions occur within an epitope of a herpesvirus peptide. In one embodiment, the amino acid sequence of any of the antigenic peptides of the invention each begins with methionine.

Conservative substitutions of amino acids within the sequence may be selected from other members of the class to which the amino acid belongs. By conservative substitutions is meant replacing an amino acid residue with another which is biologically and/or chemically similar, e.g., one hydrophobic residue for another, or one polar residue for another. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such modifications may be made using well known peptide synthesis procedures as described in e.g., Merrifield, Science 232:341-347 (1986), Barany and Merrifield, The Peptides, Gross and Meienhofer, eds. (New York, Academic Press), pp. 1-284 (1979); and Stewart and Young, Solid Phase Peptide Synthesis, (Rockford, Ill., Pierce), 2d Ed. (1984), incorporated by reference herein.

In yet another embodiment, the invention encompasses antigenic peptides that comprise a high affinity heat shock protein binding sequence. Such binding sequences are typically five to fifteen amino acid residues long and are well known in the art. Such binding sequences are exploited in the present invention to facilitate the non-covalent binding of the segment of peptide that comprises the herpesvirus peptide HLA-binding epitopes of the invention to a heat shock protein, in vitro or in vivo. Many or such binding sequences are heterologous to the herpesvirus peptide from which the HLA binding epitopes are derived. Heterologous high affinity binding sites present in many herpesvirus proteins can be used. Examples of such high affinity heat shock protein binding sequences are disclosed in PCT publication WO 97/06821 corresponding to PCT/US96/13363, Blond-Elguindi, S. et al., "Affinity panning of a library of peptides displayed on bacteriophages reveals the binding specificity of BiP." Cell 75:717-728 (1993); Flynn, G. C. et al., "Peptide binding and release by proteins implicated as catalysts of protein assembly." Science 245:385-390 (1989); Auger, I. et al., "HLA-DR4 and HLA-DR10 motifs that carry susceptibility to rheumatoid arthritis bind 70-kD heat shock proteins." Nature Medicine, 2:306-310 (1996); and Gragerov, A. et al., "Different Specificity of DnaK-peptide binding." J. Molec. Biol. 235:848-854 (1994), which are all incorporated herein by reference in their entireties. Usage of high affinity heat shock protein binding sequences is described, e.g., in Moroi et al., Proc. Nat. Acad. Sci. USA 2000, 97:3485, incorporated herein by reference in its entirety.

One example of a high affinity heat shock protein binding sequence is a heptameric segment having the sequence: Hy(Trp/X)HyXHyXHy, where Hy represents a hydrophobic amino acid residue, particularly tryptophan, leucine, or phenylalanine, and X is any amino acid. Such high affinity heat shock protein binding sequence are preferably present at either one of the ends of an amino acid sequence that comprise the herpesvirus peptide HLA-binding epitopes of the invention. Optionally, the high affinity heat shock protein binding sequence can be joined to either one of the ends by a short peptide linker that consists of several amino acids (e.g., a tripeptide linker having the sequence: glycine-serine-glycine). Such antigenic peptides can be synthesized chemically with the amino acid residues of the high affinity heat shock protein binding sequence joined to the rest of the peptide by a peptide bond. Alternatively, such antigenic peptides can be synthesized by recombinant DNA techniques as a fusion peptide. Accordingly, the antigenic peptides of the invention encompass variants or fragments of the 102 herpesvirus peptides that comprise a high affinity heat shock protein binding sequence and an optional peptide linker.

Included within the scope of the invention are derivatives or analogs of the antigenic peptides of the invention which are modified during or after translation, e.g., by glycosylation, acetylation, phosphorylation, amidation, or derivatization by known protecting/blocking groups, or proteolytic cleavage. Any of numerous chemical modifications may be carried out by known techniques, including but not limited to, reagents useful for protection or modification of free NH2- groups, free COOH— groups, OH— groups, side groups of Trp-, Tyr-, Phe-, His-, Arg-, or Lys-; specific chemical cleavage by cyanogen bromide, hydroxylamine, BNPS-Skatole, acid, or alkali hydrolysis; enzymatic cleavage by trypsin, chymotrypsin, papain, V8 protease, $NaBH_4$; acetylation, formylation, oxidation, reduction; metabolic synthesis in the presence of tunicamycin; etc.

TABLE 1

Amino acid sequences of the herpesvirus peptides, SEQ ID NOS: 1-102, and positions of HLA-binding epitopes within the peptide sequence.

| SEQ ID NO: | Name of Herpesvirus Peptide | Amino Acid Sequence of Herpesvirus Peptide | GenBank ID | Position of Amino Acid Sequence of Herpesvirus Peptide Within HSV-2 Protein | Examples of HLA-Binding Epitopes and Their Amino Acid Positions Within Herpesvirus Peptide Sequence [relevant HLA moiety in brackets] |
|---|---|---|---|---|---|
| 1 | RL02-1 | GNPRTAPRSLSL GGHTVRALSPTP PWPGTDDEDDD | 124135 | 214-248 | Amino acids 2-10 [HLA-B702], 9-17 [HLA-A201], 11-20 [HLA-A201], 21-29 [HLA-B702] |
| 2 | RL02-2 | RYLPIAGVSSVV ALAPYVNKTVT GDCLPVLDMETG | 124135 | 686-720 | Amino acids 2-11 [HLA-A201], 13-21 [HLA-A201], 22-30 [HLA-A201] |
| 3 | RS01-2 | AMSRRYDRAQK GFLLTSLRRAYA PLLARENAALTG | 1869883 | 510-544 | Amino acids 2-11 [HLA-A3], 13-21 [HLA-A201], 25-33 [HLA-A201] |
| 4 | UL01-1 | RAYLVNPFLFA AGFLEDLSHSVF PADTQETTTRRA | 136776 | 90-124 | Amino acids 3-12 [HLA-A201], 14-22 [HLA-A201], 21-30 [HLA-A201] |
| 5 | UL01-3 | ASSQSKPLATQP PVLALSNAPPRR VSPTRGRRRHT | 136776 | 185-219 | Amino acids 6-15 [HLA-B702], 9-17 [HLA-A201], 16-25 [HLA-A201], 20-28 [HLA-B702] |
| 6 | UL10-5 | DEVAPDHEAEL YARVQRPGPVP DAEPIYDTVEGYA | 1869832 | 418-452 | Amino acids 3-11 [HLA-A201], 14-22 [HLA-A3], 23-31 [HLA-B51] |
| 7 | UL13-2 | VNSAETNTHGL AYDVPEGIRRHL RNPKIRRAFTEQ | 1869835 | 441-475 | Amino acids 5-13 [HLA-A1, HLA-A26], 15-23 [HLA-B702], 25-32 [HLA-B8] |
| 8 | UL14-1 | EGVSTQDPRFV GAFMAAKAAHL ELEARLKSRARLE | 1869836 | 34-68 | Amino acids 1-10 [HLA-A26], 7-15 [HLA-B702], 14-22 [HLA-A201], 27-34 [HLA-B8] |

TABLE 1-continued

Amino acid sequences of the herpesvirus peptides, SEQ ID NOS: 1-102, and positions of HLA-binding epitopes within the peptide sequence.

| SEQ ID NO: | Name of Herpesvirus Peptide | Amino Acid Sequence of Herpesvirus Peptide | GenBank ID | Position of Amino Acid Sequence of Herpesvirus Peptide Within HSV-2 Protein | Examples of HLA-Binding Epitopes and Their Amino Acid Positions Within Herpesvirus Peptide Sequence [relevant HLA moiety in brackets] |
|---|---|---|---|---|---|
| 9 | UL14-2 | VKIRVEEQAAR RDFLTAHRRYL DPALSERLDAA DD | 1869836 | 77-111 | Amino acids 4-12 [HLA-A3], 14-22 [HLA-A201], 25-33 [HLA-A201] |
| 10 | UL16-2 | RTLAVRGDASL CQLLFGHPVDA VILRQATRRPRIT | 1869838 | 281-315 | Amino acids 2-11 [HLA-A201], 14-23 [HLA-A201], 22-30 [HLA-A201] |
| 11 | UL17-2 | LGEVTRRFPVLL ENLMRALEGTA PDAFFHTAYALA | 1869839 | 517-551 | Amino acids 3-11 [HLA-A26], 10-19 [HLA-A201], 18-27 [HLA-A3], 23-31 [HLA-B702] |
| 12 | UL20-1 | SRLPPHTQPVFS KRVVMFAWSFL VLKPLELVAAGM | 1869842 | 50-84 | Amino acids 2-10 [HLA-A201], 16-24 [HLA-A201], 22-31 [HLA-A201] |
| 13 | UL20-2 | VAPACIIAAVLA YYVTWLARALL LYVNIKRDRLPL | 1869842 | 93-127 | Amino acids 1-10 [HLA-A201], 10-18 [HLA-A201], 17-26 [HLA-A201], 21-29 [HLA-A201] |
| 14 | UL22-1 | VTTAEFPRDPGQ LLYIPKTYLLGR PRNASLPELPE | 1869844 | 94-128 | Amino acids 6-14 [HLA-B702], 13-20 [HLA-A201], 21-30 [HLA-A201], 24-33 [HLA-B702] |
| 15 | UL22-3 | SSDVPSVALLLF PNGTVIHLLAFD TLPIATIAPGF | 1869844 | 771-805 | Amino acids 4-12 [HLA-B702], 9-17 [HLA-A201], 20-28 [HLA-A201] |
| 16 | UL22-4 | ARLRLEARLGH LVAAILEREQSL VAHALGYQLAFV | 1869844 | 445-479 | Amino acids 4-12 [HLA-A201], 15-23 [HLA-A201], 27-35 [HLA-A201] |
| 17 | UL27-2 | MLEDHEFVPLE VYTRHEIKDSGL LDYTEVQRRNQL | 2815498 | 674-708 | Amino acids 1-9 [HLA-A201], 11-19 [HLA-A3], 18-26 [HLA-A1], 26-34 [HLA-A1] |
| 18 | UL27-3 | YSRPLVSFRYED QGPLIEGQLGEN NELRLTRDALE | 2815498 | 594-628 | Amino acids 1-10 [HLA-A1], 9-17 [HLA-A2402], 20-29 [HLA-A201], 26-34 [HLA-B8] |
| 19 | UL33-1 | LEVIFPTTDAKL NYLSRTQRLASL LTYAGPIKAPD | 1869856 | 55-89 | Amino acids 3-12 [HLA-A201], 15-24 [HLA-A201], 23-31 [HLA-A201] |
| 20 | UL33-2 | TQDTACVHGEL LARKRERFAAVI NRFLDLHQILRG | 1869856 | 96-130 | Amino acids 3-11 [HLA-A26], 12-19 [HLA-B8], 21-29 [HLA-A3] |
| 21 | UL34-1 | DEAFPIEYVLRL MNDWADVPCN PYLRVQNTGVS VL | 1869857 | 61-95 | Amino acids 4-12 [HLA-B702, HLA-A201], 11-20 [HLA-A201], 20-28 [HLA-B702], 25-34 [HLA-A201] |
| 22 | UL36-3 | PQPPLPQPPLPQP PLPQPPLPPVTR TLTPQSRDSV | 1869859 | 2926-2960 | Amino acids 2-10 [HLA-B702], 12-20 [HLA-B702], 19-27 [HLA-A201], 26-35 [HLA-A201] |
| 23 | UL36-4 | ARDVIRETDAFY GDLADLDLQLR AAPPANLYARLG | 1869859 | 640-674 | Amino acids 3-12 [HLA-A3], 14-22 [HLA-A201], 21-30 [HLA-A201], 25-34 [HLA-B702] |
| 24 | UL37-1 | LPETALLAENLP GLLVHRMAVAL PETPEAAFREMD | 1869860 | 100-134 | Amino acids 5-14 [HLA-A201], 13-21 [HLA-A201], 21-29 [HLA-A201] |
| 25 | UL40-2 | ILSPGALAAIEN YVRFSADRLLG LIHMQPLYSAPA | 132624 | 269-303 | Amino acids 1-10 [HLA-A201], 16-24 [HLA-A201], 24-32 [HLA-A201] |

TABLE 1-continued

Amino acid sequences of the herpesvirus peptides, SEQ ID NOS: 1-102, and positions of HLA-binding epitopes within the peptide sequence.

| SEQ ID NO: | Name of Herpesvirus Peptide | Amino Acid Sequence of Herpesvirus Peptide | GenBank ID | Position of Amino Acid Sequence of Herpesvirus Peptide Within HSV-2 Protein | Examples of HLA-Binding Epitopes and Their Amino Acid Positions Within Herpesvirus Peptide Sequence [relevant HLA moiety in brackets] |
|---|---|---|---|---|---|
| 26 | UL40-3 | VHSRVYNIIQLV LFHNNDQARRA YVARTINHPAIR | 132624 | 123-157 | Amino acids 4-13 [HLA-A3], 16-24 [HLA-A1], 26-34 [B27] |
| 27 | UL41-1 | AAPSGAPSKPAL RLAHLFCIRVLR ALGYAYINSGQ | 549322 | 158-192 | Amino acids 6-14 [HLA-B702], 13-22 [HLA-A201], 22-31 [HLA-A201] |
| 28 | UL41-2 | TIAELVEHRYVK YVISLISPKERGP WTLLKRLPIY | 549322 | 408-442 | Amino acids 2-10 [HLA-A1], 13-21 [HLA-A3], 24-32 [HLA-B702] |
| 29 | UL41-3 | GYFTPIAVDLW NVMYTLVVKY QRRYPSYDREAI TL | 549322 | 26-60 | Amino acids 5-13 [HLA-A201], 9-17 [HLA-A201], 17-25 [HLA-A26], 25-33 [HLA-B702] |
| 30 | UL44-1 | GPGASPRLYSVV GPLGRQRLIIEEL TLETQGMYYW | 2842677 | 179-213 | Amino acids 3-11 [HLA-A201], 13-22 [HLA-B702], 21-29 [HLA-A201] |
| 31 | UL44-4 | DRPSAYGTWVR VRVFRPPSLTIHP HAVLEGQPFKA | 2842677 | 219-253 | Amino acids 2-10 [HLA-B702], 13-21 [HLA-A3], 19-28 [HLA-A201], 26-34 [HLA-A3] |
| 32 | UL45-1 | PATLIPRAAAKH LAALTRVQAER SSGYWWVNGD GI | 1869868 | 90-124 | Amino acids 3-11 [HLA-A3], 8-16 [HLA-A201], 18-27 [HLA-A3] |
| 33 | UL46-1 | DPAGDCDPSLH VLLRPTLLPKLL VRAPFKSGAAAA | 1869869 | 148-182 | Amino acids 1-10 [HLA-B702], 13-22 [HLA-A201], 18-26 [HLA-A201], 26-34 [HLA-B702] |
| 34 | UL46-2 | ADPSRPSTDTAL RLSELLAYVSVL YHWASWMLWTA | 1869869 | 208-242 | Amino acids 2-11 [HLA-B702], 13-21 [HLA-A201], 23-32 [HLA-A201] |
| 35 | UL49-1 | FRRGAGPMRAR PRGEVRFLHYD EAGYALYRDSS SD | 186982 | 39-73 | Amino acids 1-9 [HLA-B2705], 11-19 [HLA-B702], 21-29 [BLA-A201], 27-35 [HLA-A3] |
| 36 | UL49-2 | SPTAPWTPRVA GFNKRVFCAAV GRLAATHARLA AV | 186982 | 184-218 | Amino acids 4-13 [HLA-B702], 16-24 [HLA-A3], 27-35 [HLA-A201] |
| 37 | UL53-1 | ATYLLNYAGRI VSSVFLQYPYTK ITRLLCELSVQR | 1869877 | 159-193 | Amino acids 3-11 [HLA-A201], 7-15 [HLA-A201], 16-24 [HLA-A201], 23-31 [HLA-A201] |
| 38 | UL53-2 | LSGIAVRLCYIA VVAGVVLVALR YEQEIQRRLFDL | 1869877 | 304-338 | Amino acids 3-11 [HLA-A201], 12-20 [HLA-A201], 21-29 [HLA-A3], 27-35 [HLA-A26] |
| 39 | UL53-3 | VSIIALTELYFIL RRGSAPKNAEP AAPRGRSKGWS | 1869877 | 259-293 | Amino acids 3-12 [HLA-A201], 12-20 [HLA-A3], 18-26 [HLA-B702], 24-32 [HLA-A3] |
| 40 | UL54-1 | DPIIGTAAAVLE NLATRLRPFLQC YLKARGLCGLD | 124181 | 377-411 | Amino acids 2-10 [HLA-A201], 3-11 [HLA-A201], 5-14 [HLA-A201], 10-18 [HLA-A201], 13-22 [HLA-A201], 17-26 [HLA-A201], 25-34 [HLA-A201] |
| 41 | UL54-2 | LDDLCSRRRLSD IKDIASFVLVILA | 124181 | 410-444 | Amino acids 3-10 [HLA-B8], 12-19 [HLA-B8], 15-23 [HLA- |

TABLE 1-continued

Amino acid sequences of the herpesvirus peptides, SEQ ID NOS: 1-102, and positions of HLA-binding epitopes within the peptide sequence.

| SEQ ID NO: | Name of Herpesvirus Peptide | Amino Acid Sequence of Herpesvirus Peptide | GenBank ID | Position of Amino Acid Sequence of Herpesvirus Peptide Within HSV-2 Protein | Examples of HLA-Binding Epitopes and Their Amino Acid Positions Within Herpesvirus Peptide Sequence [relevant HLA moiety in brackets] |
|---|---|---|---|---|---|
| | | RLANRVERGV | | | A201], 23-31 [HLA-A201], 26-35 [HLA-A201] |
| 42 | US05-2 | IVGILGCAAVGA APTGPASDTTNA TARLPTHPPLI | 137132 | 11-45 | Amino acids 4-13 [HLA-A201], 13-21 [HLA-B702], 20-28 [HLA-A26], 26-34 [HLA-B2705] |
| 43 | US06-1 | RWSYYDSFSAV SEDNLGFLMHA PAFETAGTYLRLV | 419141 | 159-193 | Amino acids 10-19 [HLA-A201], 22-30 [HLA-B702], 26-34 [HLA-A26] |
| 44 | US06-3 | SKAYQQGVTVD SIGMLPRFIPENQ RTVALYSLKIA | 419141 | 230-264 | Amino acids 2-10 [HLA-A201], 8-16 [HLA-A201], 19-27 [HLA-A201], 20-29 [HLA-B702], 24-32 [B2705] |
| 45 | US09-2 | DSVRSSASVPLY PAASPVPAEAY YSESEDEAANDF | 1869893 | 9-43 | Amino acids 2-10 [HLA-A3], 10-18 [HLA-A201], 12-20 [HLA-B702], 27-35 [HLA-B4402] |
| 46 | US10-1 | AGLPSPVPYAPL GSPDPSSPRQRT YVLPRVGIHNA | 1869894 | 93-127 | Amino acids 3-12 [HLA-B702], 16-25 [HLA-A26], 26-35 [HLA-A201] |
| 47 | US10-2 | DRPPESPGSELY PLNAQALAHLQ MLPADHRAFFRT | 1869894 | 145-179 | Amino acids 3-11 [HLA-B702], 13-22 [HLA-A201], 25-33 [HLA-B702] |
| 48 | US11-1 | VSPAHPQTPVG AGSRDLSLKGTP SDGMQPRGADTL | 1869895 | 5-39 | Amino acids 2-10 [HLA-B702], 8-17 [HLA-B702], 26-35 [HLA-A201] |
| 49 | US11-2 | AAGKRGDSGLL RVCAALSIPKPS EAVRPSRIPRAP | 1869895 | 59-93 | Amino acids 2-10 [HLA-B8], 9-17 [HLA-A201], 18-26 [HLA-A201], 25-33 [HLA-A3] |
| 50 | RL2-3 | TGHIGAYVVLV DQTGNVADLLR AAAPAWSRRTL LP | 124135 | 719-753 | Amino acids 3-11 [HLA-A201], 9-17 [HLA-A201], 16-25 [HLA-A203], 25-34 [HLA-B702] |
| 51 | RL2-4 | VRPPDYPTPPAS EWNSLWMTPV GNMLFDQGTLV GA | 124135 | 760-794 | Amino acids 3-11 [HLA-B702], 9-17 [HLA-B702], 16-25 [HLA-A201], 25-33 [HLA-A201] |
| 52 | RS1-1 | GDVALDQACFR ISGAARNSSSFIS GSVARAVPHLG | 1869883 | 456-490 | Amino acids 4-12 [HLA-A201], 15-23 [HLA-B51], 26-34 [HLA-A201] |
| 53 | RS1-3 | GAPDVSALGAQ GVLLLSTRDLAF AGAVEFLGLLAG | 1869883 | 1014-1048 | Amino acids 2-10 [HLA-B702], 7-16 [HLA-A201], 13-21 [HLA-A201], 25-33 [HLA-A201] |
| 54 | RS1-4 | SGEAVDEPAAD GVVSPRQLALL ASMVDEAVRTIPS | 1869883 | 96-130 | Amino acids 4-12 [HLA-A3], 13-22 [HLA-A201], 24-33 [HLA-A201] |
| 55 | UL01-2 | RTPADDVSWRY EAPSVEDYARID GIFLRYHCPGLD | 136776 | 46-80 | Amino acids 3-11 [HLA-A1], 10-19 [HLA-A1], 16-25 [HLA-A201], 26-34 [HLA-A201] |
| 56 | UL10-1 | AWLLQITVLLLA HRISQLAHLIYV LHFACLVYLAA | 1869832 | 147-181 | Amino acids 2-11 [HLA-A201], 10-18 [HLA-A201], 17-25 [HLA-A201], 24-32 [HLA-A201] |
| 57 | UL10-2 | SAPSMLICLTTL FALLVVSLLLVV EGVLCHYVRVL | 1869832 | 248-282 | Amino acids 4-12 [HLA-A201], 12-20 [HLA-A201], 19-27 [HLA-A201], 27-35 [HLA-A201] |

TABLE 1-continued

Amino acid sequences of the herpesvirus peptides, SEQ ID NOS: 1-102, and positions of HLA-binding epitopes within the peptide sequence.

| SEQ ID NO: | Name of Herpesvirus Peptide | Amino Acid Sequence of Herpesvirus Peptide | GenBank ID | Position of Amino Acid Sequence of Herpesvirus Peptide Within HSV-2 Protein | Examples of HLA-Binding Epitopes and Their Amino Acid Positions Within Herpesvirus Peptide Sequence [relevant HLA moiety in brackets] |
|---|---|---|---|---|---|
| 58 | UL10-3 | VPLRLDTQSLLA TYAITSTLLLAA AVYAAVGAVTS | 1869832 | 82-116 | Amino acids 2-10 [HLA-A201], 10-19 [HLA-A201], 21-30 [HLA-A201], 25-33 [HLA-A201] |
| 59 | UL10-4 | GTYLRQVHGLI DPAPTHHRIVGP VRAVMTNALLLG | 1869832 | 191-125 | Amino acids 1-10 [HLA-A201], 9-17 [HLA-A3], 19-27 [HLA-A201], 26-34 [HLA-A26] |
| 60 | UL11-1 | ITTDGGEVVSLT AHEFDVVDIESE EEGNFYVPPDV | 1869833 | 18-52 | Amino acids 2-11 [HLA-A201], 10-19 [HLA-A201], 22-30 [HLA-A1] |
| 61 | UL11-2 | RVVTRAPGPQY RRASDPPSRHTR RRDPDVARPPAT | 1869833 | 53-87 | Amino acids 2-11 [HLA-A3], 14-23 [HLA-A1], 26-34 [HLA-B702] |
| 62 | UL13-1 | RAEFNNRPLKH DVGLAVDLYAL GQTLLELLVSVYV | 1869835 | 365-399 | Amino acids 7-15 [HLA-B702], 14-22 [HLA-A201], 21-29 [HLA-A201], 25-33 [HLA-A201] |
| 63 | UL13-3 | LYALGQTLLELL VSVYVAPSLGV PVTRVPGYQYFN | 1869835 | 383-417 | Amino acids 3-11 [HLA-A201], 7-15 [HLA-A201], 16-25 [HLA-A201], 20-28 [HLA-A201], 25-33 [HLA-A1] |
| 64 | UL13-4 | QRQIVFPAYDM DLGKYIGQLASL RATTPSVATALH | 1869835 | 220-254 | Amino acids 4-12 [HLA-A26], 12-20 [HLA-A201], 22-30 [HLA-A201] |
| 65 | UL16-1 | PEADLVARIANS VFVWRVVRGDE RLKIFRCLTVLT | 1869838 | 38-72 | Amino acids 4-13 [HLA-A201], 12-20 [HLA-A3], 17-26 [HLA-A3], 26-34 [HLA-A201] |
| 66 | UL17-1 | RGGPRAAGEDV LNDVLTLVPGT AKPRSLVEWLD RG | 1869839 | 327-361 | Amino acids 6-15 [HLA-A201], 11-19 [HLA-A201], 17-25 [HLA-A201], 24-32 [HLA-B702] |
| 67 | UL17-3 | TATAEDVSITQE NEEILALVQRAV QDVTRRHPVRA | 1869839 | 242-276 | Amino acids 1-9 [HLA-B51], 11-19 [HLA-B4402], 18-27 [HLA-A201], 26-34 [HLA-A3] |
| 68 | UL18-1 | NPDPRTPGELPD LNVLYYNGARL SLVADVQQLASV | 1869840 | 164-198 | Amino acids 5-13 [HLA-A201], 15-23 [HLA-A201], 24-32 [HLA-A201] |
| 69 | UL18-2 | TELRSLVLNMV YSITEGTTLILTL IPRLLALSAQD | 1869840 | 200-234 | Amino acids 5-14 [HLA-A201], 13-21 [HLA-A201], 23-31 [HLA-A201] |
| 70 | UL22-2 | ASYVVTHTPLPR GIGYKLTGVDV RRPLFITYLTAT | 1869844 | 671-705 | Amino acids 7-16 [HLA-A1], 13-21 [HLA-A201], 23-31 [HLA-A1] |
| 71 | UL27-1 | VGQPQYYLATG GFLIAYQPLLSN TLAELYVREYMR | 2815498 | 431-465 | Amino acids 7-15 [HLA-A201], 13-21 [HLA-A201], 20-28 [HLA-A201], 24-32 [HLA-A201] |
| 72 | UL33-3 | ALRSQTLESLDA RYVSRDGAGDA AVWFEDMTPAEL | 1869856 | 21-55 | Amino acids 1-10 [HLA-A201], 9-17 [HLA-A3], 16-24 [HLA-A201], 27-35 [HLA-B4402] |
| 73 | UL34-2 | VQLFRAPRPGPP ALLLLAAGLFLG AAIWWAVGARL | 1869857 | 242-276 | Amino acids 6-14 [HLA-B702], 13-21 [HLA-A201], 22-31 [HLA-A201], 26-35 [HLA-A201] |

TABLE 1-continued

Amino acid sequences of the herpesvirus peptides, SEQ ID NOS: 1-102, and positions of HLA-binding epitopes within the peptide sequence.

| SEQ ID NO: | Name of Herpesvirus Peptide | Amino Acid Sequence of Herpesvirus Peptide | GenBank ID | Position of Amino Acid Sequence of Herpesvirus Peptide Within HSV-2 Protein | Examples of HLA-Binding Epitopes and Their Amino Acid Positions Within Herpesvirus Peptide Sequence [relevant HLA moiety in brackets] |
|---|---|---|---|---|---|
| 74 | UL34-3 | GAPGGAITAEQTNVILHSTETTGLSLGDLDDVKGR | 1869857 | 105-139 | Amino acids 7-16 [HLA-A201], 15-23 [HLA-A201], 23-32 [HLA-A201] |
| 75 | UL34-4 | GKPYGGRPGDAFEGLVQRIRLIVPATLRGGGGESG | 1869857 | 5-39 | Amino acids 7-15 [HLA-B702], 14-22 [HLA-A201], 18-26 [HLA-A201], 26-34 [HLA-A3] |
| 76 | UL35-1 | APQFHRPSTITADNVRALGMRGLVLATNNAQFIMD | 1869858 | 3-37 | Amino acids 1-9 [HLA-B702], 10-18 [HLA-A201], 19-27 [HLA-A201], 24-33 [HLA-A201] |
| 77 | UL35-2 | PHGTQGAVREFLRGQAAALTDLGVTHANNTFAPQP | 1869858 | 43-77 | Amino acids 3-11 [HLA-A26], 11-19 [HLA-A201], 18-27 [HLA-A201] |
| 78 | UL36-1 | ETYLQDEPFVERRVAITHPLRGEIGGLGALFVGVV | 1869859 | 240-274 | Amino acids 1-9 [HLA-A26], 7-16 [HLA-B702], 13-21 [HLA-A3], 19-27 [HLA-A201], 26-35 [HLA-A201] |
| 79 | UL36-2 | DTATALAGLHPAFVVVLKTLFADAPETPVLVQFFS | 1869859 | 1097-1131 | Amino acids 1-9 [HLA-A201], 8-17 [HLA-A201], 13-21 [HLA-A26], 24-33 [HLA-B702] |
| 80 | UL36-5 | ARLRDEVVRRVPWEMNFDALGGLLAEFDAAAADLA | 1869859 | 1820-1854 | Amino acids 2-11 [HLA-A201], 11-20 [HLA-B702], 14-23 [HLA-A201], 23-31 [HLA-A201] |
| 81 | UL36-6 | VTAMDLVLAAVLLGAPVVVALRNTTAFSRESELEL | 1869859 | 2311-2345 | Amino acids 3-11 [HLA-A201], 12-21 [HLA-A201], 20-29 [HLA-A3], 25-33 [HLA-B702] |
| 82 | UL37-2 | LMARVRTDAAVFDPDVPFLSASALAIFRPAVTGLL | 1869860 | 343-377 | Amino acids 4-12 [HLA-A3], 10-19 [HLA-A201], 18-26 [HLA-A201], 25-34 [HLA-A201] |
| 83 | UL37-3 | ANLTTPAYSLLFPSPIVQEGLRFLALVSNWVTLFS | 1869860 | 215-249 | Amino acids 2-10 [HLA-A201], 9-17 [HLA-A201], 16-24 [HLA-A201], 25-33 [HLA-A201] |
| 84 | UL37-4 | VGPTMQMADNIEQLLRELYVIARGAVEQLRPAVQL | 1869860 | 689-723 | Amino acids 6-14 [HLA-A201], 13-21 [HLA-A201], 21-29 [HLA-A201], 25-34 [HLA-B702] |
| 85 | UL37-5 | SVDLSPQGLAATLSMDWLLINELLQVTDGVFRASA | 1869860 | 1010-1044 | Amino acids 5-13 [HLA-B702], 14-23 [HLA-A201], 18-26 [HLA-A201], 22-30 [HLA-A201] |
| 86 | UL40-1 | SDPEKFILMILIEGVFFAASFAAIAYLRTNNLLRV | 132624 | 172-206 | Amino acids 1-10 [HLA-A201], 7-15 [HLA-A201], 18-27 [HLA-A201], 26-35 [HLA-A201] |
| 87 | UL40-4 | LRSLSILNRWLETELVFVGDEEDVSKLSEGELGFY | 132624 | 46-80 | Amino acids 3-11 [HLA-A201], 10-18 [HLA-A201], 17-26 [HLA-A3], 27-35 [HLA-A1] |
| 88 | UL41-4 | SSEILTPPELVQVPNAQRVAEHRGYVAGRRRHVIH | 549322 | 360-394 | Amino acids 4-13 [HLA-A1], 10-18 [HLA-A3], 18-26 [HLA-A3], 25-33 [HLA-A1] |
| 89 | UL44-2 | EGAGIGVAVLVAVVLAGTAVVYLTHASSVRYRRLR | 2842677 | 446-480 | Amino acids 4-13 [HLA-A201], 14-23 [HLA-A201], 23-31 [HLA-A1] |

TABLE 1-continued

Amino acid sequences of the herpesvirus peptides, SEQ ID NOS: 1-102, and positions of HLA-binding epitopes within the peptide sequence.

| SEQ ID NO: | Name of Herpesvirus Peptide | Amino Acid Sequence of Herpesvirus Peptide | GenBank ID | Position of Amino Acid Sequence of Herpesvirus Peptide Within HSV-2 Protein | Examples of HLA-Binding Epitopes and Their Amino Acid Positions Within Herpesvirus Peptide Sequence [relevant HLA moiety in brackets] |
|---|---|---|---|---|---|
| 90 | UL44-3 | TRTEFRLQIWRY ATATDAEIGTAP SLEEVMVNVSA | 2842677 | 119-153 | Amino acids 2-11 [HLA-A1], 11-20 [HLA-A2402], 18-26 [HLA-B4402], 25-33 [HLA-A201] |
| 91 | UL45-2 | IDEFFEELAIRIC YYPRSPGGFVRF VTSIRNALGL | 1869868 | 137-171 | Amino acids 5-14 [HLA-A1], 15-23 [HLA-B702], 25-33 [HLA-A26] |
| 92 | UL45-3 | RVPAVAWIGVG AIVGAFALVAA LVLVPPRSSWGLS | 1869868 | 23-57 | Amino acids 4-13 [HLA-A201], 12-20 [HLA-A201], 18-26 [HLA-A201], 26-34 [HLA-B702] |
| 93 | UL48-1 | GELRAREESYRT VLANFCSALYR YLRASVRQLHRQ | 2827761 | 157-191 | Amino acids 2-10 [HLA-A3], 13-21 [HLA-A201], 20-29 [HLA-A201], 24-32 [HLA-A201] |
| 94 | UL48-2 | SRGRTRNNYGS TIEGLLDLPDDD DAPAEAGLVAPR | 2827761 | 363-397 | Amino acids 1-9 [HLA-B2705], 11-19 [HLA-A201], 19-27 [HLA-B702], 25-33 [HLA-B702] |
| 95 | UL54-1 | DPIIGTAAAVLE NLATRLRPFLQC YLKARGLCGLD | 124181 | 377-411 | Amino acids 2-10 [HLA-A201], 10-18 [HLA-A201], 17-26 [HLA-A201], 25-34 [HLA-A201] |
| 96 | UL54-2 | LDDLCSRRRLSD IKDIASFVLVILA RLANRVERGV | 124181 | 410-444 | Amino acids 3-10 [HLA-B8], 12-19 [HLA-B8], 15-24 [HLA-A201], 23-31 [HLA-A201] |
| 97 | UL54-3 | GVSEIDYTTVGV GAGETMHFYIP GACMAGLIEILD | 124181 | 443-477 | Amino acids 1-10 [HLA-A201], 11-19 [HLA-A3], 21-30 [HLA-A201], 26-34 [HILA-A201] |
| 98 | UL54-4 | SRRRLSDIKDIAS FVLVILARLANR VERGVSEIDY | 124181 | 415-449 | Amino acids 3-12 [HLA-B2705], 10-19 [HLA-A201], 18-26 [HLA-A201], 26-35 [HLA-A1] |
| 99 | US05-1 | PLIRSGGFAVPLI VGGLCLMILGM ACLLEVLRRLG | 137132 | 43-77 | Amino acids 2-10 [HLA-A201], 11-19 [HLA-A201], 19-27 [HLA-A201], 26-34 [HLA-A201] |
| 100 | US09-1 | RRRRRRTRCVG LVIACLVVALLS GGFGALLVWLLR | 1869893 | 55-89 | Amino acids 4-12 [HLA-B8], 13-21 [HLA-A201], 21-29 [HLA-A201] |
| 101 | US10-3 | GHHVSPGSPGFP ESPGNREFHDLP ENPGSRAYPGT | 1869894 | 36-70 | Amino acids 3-11 [HLA-A3], 14-22 [HLA-B702], 23-31 [HLA-B702] |
| 102 | US06-2 | PHHAPAAPSNPG LIIGALAGSTLA VLVIGGIAFWV | 419141 | 329-363 | Amino acids 17-25 and 22-31 [HLA A201], 7-15 and 4-13 [HLA B702] |

5.1.1. Production of Antigenic Peptides by Chemical Synthesis

The antigenic peptides of the invention can be synthesized by standard chemical methods including the use of a peptide synthesizer. Conventional peptide synthesis or other synthetic protocols well known in the art can be used.

Peptides having the amino acid sequence of an antigenic peptide can be synthesized, for example, by solid-phase peptide synthesis using procedures similar to those described by Merrifield, 1963, J. Am. Chem. Soc., 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton, et al., 1989, Solid Phase Peptide Synthesis: A Practical Approach, IRL Press, and Bodanszky, 1993, Peptide Chemistry, A Practical Textbook, 2nd Ed., Springer-Verlag).

In addition, peptide analogs and derivatives of the antigenic peptides of the invention can be chemically synthesized as described supra. If desired, nonclassical amino acids or chemical amino acid analogs can be introduced as a substitution or addition into the peptide sequence. Non-classical amino acids include, but are not limited to, the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

Purification of the resulting peptide is accomplished using conventional procedures, such as preparative HPLC using gel permeation, partition and/or ion exchange chromatography. The choice of appropriate matrices and buffers are well known in the art and so are not described in detail herein.

5.1.2. Production of Antigenic Peptides Using Recombinant DNA Technology

The antigenic peptides of the invention can also be prepared by recombinant DNA methods known in the art. A nucleic acid sequence encoding an antigenic peptide can be obtained by back translation of the amino acid sequence and synthesized by standard chemical methods, such as the use of an oligonucleotide synthesizer. Alternatively, coding information for antigenic peptides can be obtained from HSV-2 viral DNA template using specifically designed oligonucleotide primers and PCR methodologies. Variations and fragments of the herpesvirus peptides of the invention can be made by altering SEQ ID NOS: 1-102 by substitutions, insertions or deletions that provide for antigenically equivalent molecules. Due to the degeneracy of nucleotide coding sequences, DNA sequences which encode the same or a variation of an amino acid sequence as in SEQ ID NOS: 1-102 may be used in the practice of the present invention. These include, but are not limited to, nucleotide sequences which are altered by the substitution of different codons that encode an antigenically equivalent amino acid residue within the sequence, thus producing a silent or conservative change. The nucleic acid encoding an antigenic peptide can be inserted into an expression vector for propagation and expression in host cells.

As the coding sequence for peptides of the length contemplated herein can be synthesized by chemical techniques, for example, the phosphotriester method of Matteucci et al., J. Am. Chem. Soc. 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired peptide or fusion protein. A number of such vectors and suitable host systems are now available. For expression of the peptide or fusion proteins, the coding sequence will be provided with operably associated start and stop codons, promoter and terminator regions and usually a replication system to provide an expression vector for expression in the desired cellular host.

An expression construct, as used herein, refers to a nucleotide sequence encoding an antigenic peptide operably associated with one or more regulatory regions which enables expression of the peptide in an appropriate host cell. "Operably-associated" refers to an association in which the regulatory regions and the peptide sequence to be expressed are joined and positioned in such a way as to permit transcription, and ultimately, translation.

The regulatory regions necessary for transcription of the peptide can be provided by the expression vector. A translation initiation codon (ATG) may also be provided if the peptide gene sequence lacking its cognate initiation codon is to be expressed. In a compatible host-construct system, cellular transcriptional factors, such as RNA polymerase, will bind to the regulatory regions on the expression construct to effect transcription of the peptide sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to the peptide gene sequence or to insert the peptide gene sequence into the cloning site of a vector, linkers or adapters providing the appropriate compatible restriction sites may be ligated to the ends of the cDNAs by techniques well known in the art (Wu et al., 1987, Methods in Enzymol 152:343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising an antigenic peptide sequence operably associated with regulatory regions can be directly introduced into appropriate host cells for expression and production of the peptide without further cloning. The expression constructs can also contain DNA sequences that facilitate integration of the DNA sequence into the genome of the host cell, e.g., via homologous recombination. In this instance, it is not necessary to employ an expression vector comprising a replication origin suitable for appropriate host cells in order to propagate and express the peptide in the host cells.

A variety of expression vectors may be used including, but not limited to, plasmids, cosmids, phage, phagemids or modified viruses. Typically, such expression vectors comprise a functional origin of replication for propagation of the vector in an appropriate host cell, one or more restriction endonuclease sites for insertion of the peptide gene sequence, and one or more selection markers. Expression vectors may be constructed to carry nucleotide sequences for one or more of the antigenic peptides of the invention. The expression vector must be used with a compatible host cell which may be derived from a prokaryotic or eukaryotic organism including but not limited to bacteria, yeasts, insects, mammals and humans. Such host cells can be transformed to express one or more antigenic peptides, such as by transformation of the host cell with a single expression vector containing one or more nucleotide sequences encoding any of the antigenic peptides of the invention, or by transformation of the host cell with multiple expression vectors encoding different antigenic peptides of the invention.

In bacterial systems, a number of expression vectors may be advantageously selected to produce the antigenic peptides of the invention. For example, when a large quantity of such a protein is to be produced, such as for the generation of pharmaceutical compositions, vectors that direct the expression of high levels of fusion protein products that are readily purified may be desirable. Such vectors include, but are not limited, to the *E. coli* expression vector pUR278 (Ruther et al., 1983, *EMBO J.* 2, 1791), in which the peptide coding sequence may be ligated individually into the vector in frame with the lac Z coding region so that a fusion protein is produced; pIN vectors (Inouye and Inouye, 1985, *Nucleic Acids Res.* 13, 3101-3109; Van Heeke and Schuster, 1989, *J. Biol. Chem* 264, 5503-5509); and the like. pGEX vectors may also be used to express these peptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the antigenic peptide can be released from the GST moiety.

Alternatively, for long term, high yield production of properly processed peptide complexes, stable expression in mammalian cells is preferred. Cell lines that stably express peptide complexes may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while peptide is expressed continuously.

The recombinant cells may be cultured under standard conditions of temperature, incubation time, optical density and media composition. However, conditions for growth of recombinant cells may be different from those for expression of the antigenic peptides. Modified culture conditions and media may also be used to enhance production of the peptides. For example, recombinant cells containing peptides with their cognate promoters may be exposed to heat or other environmental stress, or chemical stress. Any techniques known in the art may be applied to establish the optimal conditions for producing peptide complexes.

In one embodiment of the invention, a codon encoding methionine is added at the 5' end of the nucleotide sequence encoding an antigenic peptide of the invention, to provide a signal for initiation of translation of the peptide. This methionine may remain attached to the antigenic peptide, or the methionine may by removed by the addition of an enzyme or enzymes that can catalyze the cleavage of methionine from the peptide. For example, in both prokaryotes and eukaryotes, N-terminal methionine is removed by a methionine aminopeptidase (MAP) (Tsunasawa et al., 1985, J. Biol. Chem. 260, 5382-5391). Methionine aminopeptidases have been isolated and cloned from several organisms, including *E. coli*, yeast, and rat.

The peptide may be recovered from the bacterial, mammalian, or other host cell types, or from the culture medium, by methods known to those of skill in the art (see, for example, Current Protocols in Immunology, vol. 2, chapter 8, Coligan et al. (ed.), John Wiley & Sons, Inc.; Pathogenic and Clinical Microbiology: A Laboratory Manual by Rowland et al., Little Brown & Co., June 1994; which are incorporated herein by reference in their entireties).

5.2. Vaccine Adjuvants and Formulations

In one embodiment, the pharmaceutical compositions of the invention comprise antigenic peptides of the invention, and a pharmaceutically acceptable carrier or excipient. In this embodiment, the antigenic peptides preferably comprise a high affinity heat shock protein binding site that can facilitate their binding to heat shock proteins in vivo after the pharmaceutical composition is administered to a subject. Adjuvant(s) can be administered separately from such antigenic peptides of the invention.

In another embodiment, the pharmaceutical compositions comprise antigenic peptides of the invention which form a molecular complex with one or more different adjuvant(s), and a pharmaceutically acceptable carrier or excipient. Preferably, the adjuvant is a heat shock protein which forms a non-covalent complex with an antigenic peptide. This preferred embodiment is described separately in Section 5.3. Examples of base buffers include (i) PBS; (ii) 10mM $KPO_4$, 150 mM NaCl; (iii) 10 mM HEPES, 150 mM NaCl; (iv) 10 mM imidazole, 150 mM NaCl; and (v) 20 mM sodium citrate. Excipients that can be used include (i) glycerol (10%, 20%); (ii) Tween 50 (0.05%, 0.005%); (iii) 9% sucrose; (iv) 20% sorbitol; (v) 10 mM lysine; or (vi) 0.01 mM dextran sulfate.

In yet another embodiment, the antigenic peptides of the invention are present in a composition in admixture with one or more adjuvants. Many different adjuvants can be used with the antigenic peptides of the invention. The peptide(s) and adjuvant(s) may be mixed together in the same fluid volume, or complexes of the peptide(s) and adjuvant(s) may be contained within a composition.

A variety of adjuvants may be used in the practice of the invention, including but not limited to systemic adjuvants and mucosal adjuvants. A systemic adjuvant is an adjuvant that can be delivered parenterally. Systemic adjuvants include adjuvants that create a depot effect, adjuvants that stimulate the immune system and adjuvants that do both. An adjuvant that creates a depot effect as used herein is an adjuvant that causes the antigen to be slowly released in the body, thus prolonging the exposure of immune cells to the antigen. This class of adjuvants includes but is not limited to alum (e.g., aluminum hydroxide, aluminum phosphate); or emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720, AirLiquide, Paris, France); MF-59 (a squalene-in-water emulsion stabilized with Span 85 and Tween 80; Chiron Corporation, Emeryville, Calif.; and PROVAX (an oil-in-water emulsion containing a stabilizing detergent and a micelle-forming agent; IDEC, Pharmaceuticals Corporation, San Diego, Calif.).

Other adjuvants stimulate the immune system, for instance, cause an immune cell to produce and secrete cytokines or IgG. This class of adjuvants includes but is not limited to immunostimulatory nucleic acids, such as CpG oligonucleotides; saponins purified from the bark of the *Q. saponaria* tree, such as QS21; poly[di(carboxylatophenoxy) phosphazene (PCPP polymer; Virus Research Institute, USA); derivatives of lipopolysaccharides (LPS) such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.).

Other systemic adjuvants are adjuvants that create a depot effect and stimulate the immune system. These compounds have both of the above-identified functions of systemic adjuvants. This class of adjuvants includes but is not limited to ISCOMs (Immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

The mucosal adjuvants useful according to the invention are adjuvants that are capable of inducing a mucosal immune response in a subject when administered to a mucosal surface in conjunction with complexes of the invention. Mucosal adjuvants include but are not limited to CpG nucleic acids (e.g. PCT published patent application WO 99/61056), bacterial toxins: e.g., Cholera toxin (CT), CT derivatives including but not limited to CT B subunit (CTB) (Wu et al., 1998, Tochikubo et al., 1998); CTD53 (Val to Asp) (Fontana et al., 1995); CTK97 (Val to Lys) (Fontana et al., 1995); CTK104 (Tyr to Lys) (Fontana et al., 1995); CTD53/K63 (Val to Asp, Ser to Lys) (Fontana et al., 1995); CTH54 (Arg to His) (Fontana et al., 1995); CTN107 (His to Asn) (Fontana et al., 1995); CTE114 (Ser to Glu) (Fontana et al., 1995); CTE112K (Glu to Lys) (Yamamoto et al., 1997a); CTS61F (Ser to Phe) (Yamamoto et al., 1997a, 1997b); CTS 106 (Pro to Lys) (Douce et al., 1997, Fontana et al., 1995); and CTK63 (Ser to Lys) (Douce et al., 1997, Fontana et al., 1995), Zonula occludens toxin (zot), *Escherichia coli* heat-labile enterotoxin, Labile Toxin (LT), LT derivatives including but not limited to LT B subunit (LTB) (Verweij et al., 1998); LT7K (Arg to Lys) (Komase et al., 1998, Douce et al., 1995); LT61F (Ser to Phe) (Komase et al., 1998); LT112K (Glu to Lys) (Komase et al., 1998); LT118E (Gly to Glu) (Komase et al., 1998); LT146E (Arg to Glu) (Komase et al., 1998); LT192G (Arg to Gly) (Komase et al., 1998); LTK63 (Ser to Lys) (Marchetti et al., 1998, Douce et al., 1997, 1998, Di Tommaso et al., 1996); and LTR72 (Ala to Arg) (Giuliani et al., 1998), *Pertussis* toxin, PT. (Lycke et al., 1992, Spangler B D, 1992, Freytag and Clemments, 1999, Roberts et al., 1995, Wilson et al., 1995) including PT-9K/129G (Roberts et al., 1995, Cropley et al., 1995); Toxin derivatives (see below) (Holmgren et al., 1993, Verweij et al., 1998, Rappuoli et al., 1995, Freytag and Clements, 1999); Lipid A derivatives (e.g., monophosphoryl lipid A, MPL) (Sasaki et al., 1998, Vancott et al., 1998; Muramyl Dipeptide (MDP) derivatives (Fukushima et al., 1996, Ogawa et al., 1989, Michalek et al., 1983, Morisaki et al., 1983); bacterial outer membrane proteins (e.g., outer surface protein A (OspA) lipoprotein of *Borrelia burgdorferi*, outer membrane protine of *Neisseria meningitidis*) (Marinaro et al., 1999, Van de Verg et al., 1996); oil-in-water emulsions (e.g., MF59) (Barchfield et al., 1999, Verschoor et al., 1999, O'Hagan, 1998); aluminum salts (Isaka et al., 1998, 1999); and Saponins (e.g., QS21, Aquila Biopharmaceuticals, Inc., Farmington, Mass.) (Sasaki et al., 1998, MacNeal et al., 1998), ISCOMs, MF-59 (a squalene-in-water emulsion stabilized with Span 85 and Tween 80; Chiron Corporation, Emeryville, Calif.); the Seppic ISA series of Montanide adjuvants (e.g., Montanide ISA 720; AirLiquide, Paris, France); PROVAX (an oil-in-water emulsion containing a stabilizing detergent and a micell-forming agent; IDEC Pharmaceuticals Corporation, San Diego, Calif.); Syntext Adjuvant Formulation (SAF; Syntex Chemicals, Inc., Boulder, Colo.); poly[di(carboxylatophenoxy)]phosphazene (PCPP polymer; Virus Research Institute, USA) and *Leishmania* elongation factor (Corixa Corporation, Seattle, Wash.).

The antigenic peptides and adjuvants may be combined in many ways. For example, different peptides may be mixed together first to form a mixture and then complexed with an adjuvant or adjuvants to form a composition. As another example, different antigenic peptides may be complexed individually with an adjuvant or adjuvants, and the resulting batches of peptide-adjuvant complexes may then be mixed to form a composition. The adjuvant can be administered prior to, during, or following administration of the antigenic peptides. Administration of the adjuvant and antigenic peptides can be at the same or different administration sites. In a preferred embodiment, the antigenic peptides of the invention are complexed with heat shock proteins as described in Section 5.3. Antigenic peptide-HSP complexes can be covalent or non-covalent; methods of forming such complexes is described in Section 5.3.2. infra.

In addition to the adjuvant that is complexed to or mixed with the antigenic peptides of the invention, additional adjuvant(s) can be added to the composition comprising the complexes of peptides and first adjuvant and administered as a single composition. Alternatively, the additional adjuvants can be co-administered in combination with the complexes of peptides and first adjuvant. Preferred examples of such additional adjuvants include saponins, and immunostimulatory nucleic acids. In specific embodiments, the second adjuvant added to the composition comprising HSPs and the antigenic peptides is QS-21.

5.2.1. Preparation of the Pharmaceutical Compositions

The invention encompasses pharmaceutical compositions comprising the antigenic peptides of the present invention either by itself as the active ingredient or in combination with one or more adjuvants, for the prevention and treatment of HSV-1 and HSV-2. In a specific embodiment, the invention encompasses pharmaceutical compositions comprising the antigenic peptides of the invention mixed or complexed with HSPs. In a preferred embodiment, the pharmaceutical compositions are prepared using Phosphate Buffered Saline (PBS). The vaccine formulation of the invention may be prepared by any method that results in a stable, sterile, preferably injectable formulation.

The concentration of the peptides used in the pharmaceutical compositions of the invention may be at least 10% weight by volume (w/v), at least 15% (w/v), at least 20% (w/v), at least 25% (w/v), or at least 30% (w/v). Alternatively, the combined concentration of the peptides and adjuvants used in the pharmaceutical compositions of the invention may be at least 10% (w/v), at least 15% (w/v), at least 20% (w/v), at least 25% (w/v), or at least 30% (w/v). The concentration at which the efficacy of a vaccine formulation of the invention is enhanced can be determined using standard methods known to one skilled in the art, e.g., determined by the antibody or T-cell response to the peptide-adjuvant mixture or complex relative to a control formulation, e.g., a formulation comprising the peptide or adjuvant alone.

The amount of antigenic peptides and adjuvants used in the pharmaceutical compositions of the invention may vary depending on the chemical nature and the potency of the antigenic peptides and adjuvants. Typically, the starting concentration of antigenic peptides and adjuvants in the vaccine formulation of the invention is the amount that is conventionally used for eliciting the desired immune response, using the conventional routes of administration, e.g., intramuscular injection. The concentration of the antigenic peptides and adjuvants is then adjusted, e.g., by dilution using a diluent, in the pharmaceutical compositions of the invention so that an effective protective immune response is achieved as assessed using standard methods known in the art and described herein.

Pharmaceutical compositions of the invention can be optionally prepared as lyophilized product, which may then be formulated for oral administration or reconstituted to a liquid form for parenteral administration.

Pharmaceutical compositions of the invention can additionally be formulated to contain other agents including bulking agents, stabilizing agents, buffering agents, sodium chloride, calcium salts, surfactants, antioxidants, chelating agents, other excipients, and combinations thereof.

Bulking agents are preferred in the preparation of lyophilized formulations of the vaccine composition. Such bulking agents form the crystalline portion of the lyophilized product and may be selected from the group consisting of mannitol, glycine, alanine, and hydroxyethyl starch (HES). Mannitol, glycine, or alanine are preferably present in an amount of 4-10%, and HES is preferably present in an amount of 2-6%.

Stabilizing agents may be selected from the group consisting of sucrose, trehalose, raffinose, and arginine. These agents are preferably present in amounts between 1-4%. Sodium chloride can be included in the present formulations preferably in an amount of 100-300 mM, or if used without the aforementioned bulking agents, can be included in the formulations in an amount of between 300-500 mM NaCl. Calcium salts include calcium chloride, calcium gluconate, calcium glubionate, or calcium gluceptate.

Buffering agents can be any physiologically acceptable chemical entity or combination of chemical entities which have a capacity to act as buffers, including but not limited to histidine, TRIS [tris-(hydroxymethyl)-aminomethane], BIS-Tris Propane (1,3-bis-[tris-(hydroxymethyl)methylamino]-propane), PIPES [piperazine-N,N'-bis-(2-ethanesulfonic acid)], MOPS [3-(N-morpholino)ethanesulfonic acid], HEPES (N-2-hydroxyethyl-piperazine-N'-2-ethanesulfonic acid), MES [2-(N-morpholino)ethanesulfonic acid], and ACES (N-2-acetamido-2-aminoethanesulfonic acid). Typically, the buffering agent is included in a concentration of 10-50 mM. Surfactants, if present, are preferably in a concentration of 0.1% or less, and may be chosen from the group including but not limited to polysorbate 20, polysorbate 80, pluronic polyols, and BRIJ 35 (polyoxyethylene 23 laurel ether). Antioxidants, if used, must be compatible for use with a pharmaceutical preparation, and are preferably water soluble. Suitable antioxidants include homocysteine, glutathione, lipoic acid, 6-hydroxy-2,5,7,8-tetramethylchroman-2-carboxylic acid (Trolox), methionine, sodium thiosulfate, platinum, glycine-glycine-histidine (tripeptide), and butylatedhydroxytoluene (BHT). Chelating agents should preferably bind metals such as copper and iron with greater affinity than calcium, if a calcium salt is being used in the composition. A preferred chelator is deferoxamine.

Many formulations known in the art can be used in the present invention. For example, U.S. Pat. No. 5,763,401 describes a therapeutic formulation, comprising 15-60 mM sucrose, up to 50 mM NaCl, up to 5 mM calcium chloride, 65-400 mM glycine, and up to 50 mM histidine. The following specific formulations were identified as being stable: (1) 150 mM NaCl, 2.5 mM calcium chloride, and 165 mM mannitol; and (2) 1% sucrose, 30 mM sodium chloride, 2.5 mM calcium chloride, 20 mM histidine, and 290 mM glycine.

U.S. Pat. No. 5,733,873 discloses formulations which include between 0.01-1 mg/ml of a surfactant. This patent discloses formulations having the following ranges of excipients: polysorbate 20 or 80 in an amount of at least 0.01 mg/ml, preferably 0.02-1.0 mg/ml; at least 0.1 M NaCl; at least 0.5 mM calcium salt; and at least 1 mM histidine. More particularly, the following specific formulations are also disclosed: (1) 14.7-50-65 mM histidine, 0.31-0.6 M NaCl, 4 mM calcium chloride, 0.001-0.02-0.025% polysorbate 80, with or without 0.1% PEG 4000 or 19.9 mM sucrose; and (2) 20 mg/ml mannitol, 2.67 mg/ml histidine, 18 mg/ml NaCl, 3.7 mM calcium chloride, and 0.23 mg/ml polysorbate 80.

The use of low or high concentrations of sodium chloride has been described, for example U.S. Pat. No. 4,877,608 teaches formulations with relatively low concentrations of sodium chloride, such as formulations comprising 0.5 mM-15 mM NaCl, 5 mM calcium chloride, 0.2 mM-5 mM histidine, 0.01-10 mM lysine hydrochloride and up to 10% maltose, 10% sucrose, or 5% mannitol.

U.S. Pat. No. 5,605,884 teaches the use of formulations with relatively high concentrations of sodium chloride. These formulations include 0.35 M-1.2 M NaCl, 1.5-40 mM calcium chloride, 1 mM-50 mM histidine, and up to 10% sugar such as mannitol, sucrose, or maltose. A formulation comprising 0.45 M NaCl, 2.3 mM calcium chloride, and 1.4 mM histidine is exemplified.

International Patent Application WO 96/22107 describes formulations which include the sugar trehalose, for example formulations comprising: (1) 0.1 M NaCl, 15 mM calcium chloride, 15 mM histidine, and 1.27 M (48%) trehalose; or (2) 0.011% calcium chloride, 0.12% histidine, 0.002% TRIS, 0.002% Tween 80, 0.004% PEG 3350, 7.5% trehalose; and either 0.13% or 1.03% NaCl.

U.S. Pat. No. 5,328,694 describes a formulation which includes 100-650 mM disaccharide and 100 mM-1.0 M amino acid, for example (1) 0.9 M sucrose, 0.25 M glycine, 0.25 M lysine, and 3 mM calcium chloride; and (2) 0.7 M sucrose, 0.5 M glycine, and 5 mM calcium chloride.

5.3. Heat Shock Proteins and Methods of Use 5.3.1. Heat Shock Proteins

Heat shock proteins, which are also referred to interchangeably herein as stress proteins, useful in the practice of the instant invention can be selected from among any cellular protein that satisfies the following criteria. Stress proteins are capable of binding other proteins or peptides, capable of releasing the bound proteins or peptides in the presence of adenosine triphosphate (ATP) or under acidic conditions; and show at least 35% homology with any protein having the above properties. Preferably, the intracellular concentration of such protein increases when a cell is exposed to a stressful stimulus. In addition to those heat shock proteins that are induced by stress, the HSP60, HSP70, HSP90, HSP100, sHSPs, and PDI families also include proteins that are related to stress-induced HSPs in sequence similarity, for example, having greater than 35% amino acid identity, but whose expression levels are not altered by stress. Therefore it is contemplated that the definition of stress protein or heat shock protein (HSP) embraces other proteins, mutants, analogs, and variants thereof having at least 35% to 55%, preferably 55% to 75%, and most preferably 75% to 85% amino acid identity with members of these families whose expression levels in a cell are enhanced in response to a stressful stimulus.

In addition to the major HSP families described supra, an endoplasmic reticulum resident protein, calreticulin, has also been identified as yet another heat shock protein useful for eliciting an immune response when complexed to antigenic molecules (Basu and Srivastava, 1999, J. Exp. Med. 189:797-202). Other stress proteins that can be used in the invention include but are not limited to grp78 (or BiP), protein disulfide isomerase (PDI), hsp110, and grp170 (Lin et al., 1993, Mol. Biol. Cell, 4:1109-1119; Wang et al., 2001, J. Immunol., 165:490-497). Many members of these families were found subsequently to be induced in response to other stressful stimuli including, but not limited to, nutrient deprivation, metabolic disruption, oxygen radicals, hypoxia and infection with intracellular pathogens. (See Welch, May 1993, *Scientific American* 56-64; Young, 1990, *Annu. Rev. Immunol.* 8:401-420; Craig, 1993, *Science* 260:1902-1903; Gething, et al., 1992, *Nature* 355:33-45; and Lindquist, et al., 1988, *Annu. Rev. Genetics* 22:631-677), the disclosures of which are incorporated herein by reference. It is contemplated that HSPs/stress proteins belonging to all of these families can be used in the practice of the instant invention.

The major HSPs can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch, et al., 1985, *J. Cell. Biol.* 101:1198-1211). In contrast, hsp90 and hsp60 proteins are abundant at normal temperatures in most, but not all, mammalian cells and are further induced by heat (Lai, et al., 1984, *Mol. Cell. Biol.* 4:2802-10; van Bergen en Henegouwen, et al., 1987, *Genes Dev.* 1:525-31).

In various embodiments, nucleotide sequences encoding heat shock protein within a family or variants of a heat shock protein can be identified and obtained by hybridization with a probe comprising nucleotide sequence encoding an HSP under conditions of low to medium stringency.

By way of example and not limitation, procedures using such conditions of low stringency are as follows (see also Shilo and Weinberg, 1981, Proc. Natl. Acad. Sci. USA 78:6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for signal detection. If necessary, filters are washed for a third time at 65-68° C. before signal detection. Other conditions of low stringency which may be used are well known in the art (e.g., as employed for cross-species hybridizations).

In various embodiments of the invention where HSPs are used, it is contemplated that peptide-binding fragments of HSPs and functionally active derivatives, analogs, and variants of HSPs can also be used. The term HSP peptide-binding fragment is used to refer to a polypeptide that comprises a domain that is capable of becoming noncovalently associated with a peptide to form a complex and eliciting an immune response, but that is not a full-length HSP. The term variant of HSPs refers to a polypeptide that is capable of becoming noncovalently associated with a peptide to form a complex and eliciting an immune response, but that shares a high degree of sequence similarity with a HSP. To determine a region of identity between two amino acid sequences or nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul, et al., 1990, J. Mol. Biol. 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used (see http://www.ncbi.nlm.nih-.gov). Another preferred, non-limiting example of a mathematical algorithm utilized for the comparison of sequences is the algorithm of Myers and Miller, 1988, CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In one embodiment, for example, hsp70 and hsc70 peptide-binding domain derivatives and analogs can be designed. By computer modeling the three dimensional structure of the Hsp70 peptide-binding site, variants of members of the hsp70 family including hsc70 variants can be designed in which amino acid residues not involved in peptide binding or structurally important determinants may be substituted for the wild-type residues.

In a specific embodiment, an HSP peptide-binding fragment of the invention comprises a peptide-binding domain that is contiguous on its N-terminal side with a variable number of amino acids that naturally flank the peptide-binding domain on the N-terminal side and that is contiguous on the C-terminal side with a variable number of amino acids that naturally flank the peptide-binding domain on the C-terminal side, See for example, the peptide-binding fragments of HSPs disclosed in United States patent publication US 2001/0034042, which is incorporated herein by reference in its entirety.

Amino acid sequences and nucleotide sequences of naturally occurring HSPs are generally available in sequence databases, such as GenBank. Computer programs, such as Entrez, can be used to browse the database, and retrieve any amino acid sequence and genetic sequence data of interest by accession number. These databases can also be searched to identify sequences with various degrees of similarities to a query sequence using programs, such as FASTA and BLAST, which rank the similar sequences by alignment scores and statistics. Such nucleotide sequences of non-limiting examples of HSPs that can be used for preparation of the HSP peptide-binding fragments of the invention are as follows: human Hsp70, Genbank Accession No. NM_005345, Sargent et al., 1989, Proc. Natl. Acad. Sci. U.S.A., 86:1968-1972; human Hsc70: Genbank Accession Nos. P11142, Y00371; human Hsp90, Genbank Accession No. X15183, Yamazaki et al., Nucl. Acids Res. 17:7108; human gp96: Genbank Accession No. X15187, Maki et al., 1990, Proc. Natl. Acad Sci., 87: 5658-5562; human BiP: Genbank Accession No. M19645; Ting et al., 1988, DNA 7: 275-286; human Hsp27, Genbank Accession No. M24743; Hickey et al., 1986, Nucleic Acids Res. 14:4127-45; mouse Hsp70: Genbank Accession No. M35021, Hunt et al., 1990, Gene, 87:199-204; mouse gp96: Genbank Accession No. M16370, Srivastava et al., 1987, Proc. Natl. Acad. Sci., 85:3807-3811; and mouse BiP: Genbank Accession No. U16277, Haas et al., 1988, Proc. Natl. Acad. Sci. U.S.A., 85: 2250-2254. Due to the degeneracy of the genetic code, the term "HSP nucleic acid sequence", as used herein, refers not only to the naturally occurring nucleotide sequence but also encompasses all the other degenerate DNA sequences that encode the HSP.

The HSPs in the pharmaceutical preparations of the invention can be prepared by purification from tissues, or by recombinant DNA techniques. HSPs can be purified from tissues in the presence of ATP or under acidic conditions (pH 1 to pH 6.9), for subsequent in vitro complexing to one or more antigenic peptides. See Peng, et al., 1997, J. Immunol. Methods, 204:13-21; Li and Srivastava, 1993, EMBO J. 12:3143-3151, which are incorporated herein by reference in their activities. Purified heat shock proteins are substantially free of materials that are associated with the proteins in a cell, in a cell extract, in a cell culture medium, or in an individual.

Using the defined amino acid or cDNA sequences of a given HSP or a peptide-binding domains thereof, one can make a genetic construct which is transfected into and expressed in a host cell. The recombinant host cells may contain one or more copies of a nucleic acid sequence comprising a sequence that encodes an HSP or a peptide-binding fragment, operably associated with regulatory region(s) that drives the expression of the HSP nucleic acid sequence in the host cell. Recombinant DNA techniques can be readily utilized to generate recombinant HSP genes or fragments of HSP genes, and standard techniques can be used to express such HSP gene fragments. Any nucleic acid sequence encoding an HSP peptide-binding domain, including cDNA and genomic DNA, can be used to prepare the HSPs or peptide-binding fragments of the invention. An HSP gene fragment containing the peptide-binding domain can be inserted into an appropriate cloning vector and introduced into host cells so that many copies of the gene sequence are generated. A large number of vector-host systems known in the art may be used such as, but not limited to, bacteriophages such as lambda derivatives, or plasmids such as pBR322, pUC plasmid derivatives, the Bluescript vectors (Stratagene) or the pET series of vectors (Novagen). Any technique for mutagenesis known in the art can be used to modify individual nucleotides in a DNA sequence, for purpose of making amino acid substitution(s) in the expressed peptide sequence, or for creating/deleting restriction sites to facilitate further manipulations.

The HSPs or peptide-binding fragments may be expressed as fusion proteins to facilitate recovery and purification from the cells in which they are expressed. For example, the HSP or fragment may contain a signal sequence leader peptide to direct its translocation across the endoplasmic reticulum membrane for secretion into culture medium. Further, the HSP or fragment may contain an affinity label, such as a affinity label, fused to any portion of the HSP or fragment not involved in binding antigenic peptide, such as for example, the carboxyl terminal. The affinity label can be used to facilitate purification of the protein, by binding to an affinity partner molecule. A variety of affinity labels known in the art may be used, such as, but not limited to, the immunoglobulin constant regions, polyhistidine sequence (Petty, 1996, Metal-chelate affinity chromatography, in Current Protocols in Molecular Biology, Vol. 2, Ed. Ausubel et al., Greene Publish. Assoc. & Wiley Interscience), glutathione S-transferase (GST; Smith, 1993, Methods Mol. Cell Bio. 4:220-229), the E. coli maltose binding protein (Guan et al., 1987, Gene 67:21-30), and various cellulose binding domains (U.S. Pat. Nos. 5,496,934; 5,202,247; 5,137,819; Tomme et al., 1994, Protein Eng. 7:117-123), etc.

Such recombinant HSPs or fragments can be assayed for antigenic peptide binding activity (see for example, Klappa et al., 1998, EMBO J., 17:927-935) for their ability to elicit an immune response. It is preferred that the recombinant HSP produced in the host cell or library cell is of the same species as the intended recipient of the immunogenic composition. Recombinant human HSP is most preferred.

In one embodiment, the HSP isolated from tissue is a mixture of different HSPs, for example, hsp70 and hsc70. In Section 6, the HSPs used were either hsp70 isolated from murine tissue or recombinant human hsc70. In a most preferred embodiment, the pharmaceutical compositions comprise purified human hsc70 produced by recombinant DNA methods, for example using human hsc70 sequence as described in Dworniczak and Mirault, Nucleic Acids Res. 15:5181-5197 (1987) and Genbank accession no. P11142 and/or Y00371.

5.3.2. Preparation of Heat Shock Protein-Peptide Complexes

Described herein are exemplary methods for complexing in vitro a HSP with a population of antigenic peptides of the invention. In one embodiment, the complexing reaction can result in the formation of a covalent bond between a HSP and a peptide. In a preferred embodiment, the complexing reaction results in the formation of a non-covalent association between a HSP and a peptide. In various embodiments, the complexes formed in vitro are optionally purified. Purified complexes of heat shock proteins and antigenic peptides are substantially free of materials that are associated with such complexes in a cell, or in a cell extract. Where purified heat shock proteins and purified antigenic peptides are used in an in vitro complexing reaction, the term "purified" complexes of heat shock proteins and antigenic peptides do not exclude a composition that also comprises free HSP and peptides not in complexes.

Prior to complexing, HSPs can be pretreated with ATP or exposed to acidic conditions to remove any peptides that may be non-covalently associated with the HSP of interest. Acidic conditions are any pH levels in the range pH 1 to pH 6.9, including the ranges pH 1-pH 2, pH 2-pH 3, pH 3-pH 4, pH 4-pH 5, pH 5-pH 6, and pH 6-pH 6.9. When the ATP procedure is used, excess ATP is removed from the preparation by the addition of apyranase as described by Levy, et al., 1991, Cell 67:265-274. When acidic conditions are used, the buffer is readjusted to neutral pH by the addition of pH modifying reagents. The molar ratio of each or all antigenic peptides to HSP can be any ratio from 0.01:1 to 102:1, including but not limited to 0.01:1, 0.02:1, 0.05:1. 0.1:1. 0.2:1, 0.5:1, 1:1, 2:1, 3:1, 5:1, 10:1, 20:1, 30:1, 40:1, 49:1, up to 102:1. A preferred, exemplary protocol for the noncovalent complexing of a population of peptides to an HSP in vitro is discussed below:

The population of antigenic peptides (1 µg) and the pretreated HSP (9 µg) are admixed to give an approximately 5 peptides (or proteins): 1 HSP molar ratio. The population of antigenic peptides can comprise a mixture of the different antigenic peptide species of the invention. Then, the mixture is incubated for 15 minutes to 3 hours at 4° to 50° C. in a suitable binding buffer such as phosphate buffered saline pH7.4, or one containing 20 mM sodium phosphate, pH 7.2, 350 mM NaCl, 3 mM $MgCl_2$ and 1 mM phenyl methyl sulfonyl fluoride (PMSF). The preparations are then optionally purified by centrifugation through a Centricon 10 assembly (Millipore) to remove any unbound peptide. The non-covalent association of the proteins/peptides with the HSPs can be assayed by High Performance Liquid Chromatography (HPLC) or Mass Spectrometry (MS).

In an alternative embodiment of the invention, preferred for producing non-covalent complexes of hsp70 to peptides, 5 to 10 micrograms of purified hsp70 is incubated with equimolar quantities of peptides in 20 mM sodium phosphate buffer pH 7.5, 0.5M NaCl, 3 mM $MgCl_2$ and 1 mM ADP in a volume of 100 microliter at 37° C. for 1 hr. This incubation mixture can optionally be centrifuged one or more times if necessary, through a Centricon 10 assembly (Millipore) to remove any unbound peptide.

In an alternative embodiment of the invention, preferred for producing non-covalent complexes of gp96 or hsp90 to peptides, 5 to 10 micrograms of purified gp96 or hsp90 is incubated with equimolar or excess quantities of the peptides in a suitable buffer such as one containing 20 mM sodium phosphate buffer pH 7.5, 0.5M NaCl, 3 mM $MgCl_2$ at 60-65° C. for 5 to 20 min. This incubation mixture is allowed to cool to room temperature and can be optionally centrifuged one or more times if necessary, through a Centricon 10 assembly (Millipore) to remove any unbound peptide.

Following complexing with peptides, immunogenic HSP complexes can optionally be assayed using, for example, the mixed lymphocyte target cell assay (MLTC) described below. In a preferred embodiment, the complexes are measured by enzyme-linked immunospot (ELISPOT) assay (Taguchi T, et al., J Immunol Methods 1990; 128: 65-73). Once HSP-peptide complexes have been isolated and diluted, they can be optionally characterized further in animal models using the preferred administration protocols and excipients discussed below.

As an alternative to making non-covalent complexes of HSPs and peptides, the antigenic peptides can be covalently attached to HSPs.

In one embodiment, HSPs are covalently coupled to peptides by chemical crosslinking. Chemical crosslinking methods are well known in the art. For example, in a preferred embodiment, glutaraldehyde crosslinking may be used. Glutaraldehyde crosslinking has been used for formation of covalent complexes of peptides and HSPs (see Barrios et al., 1992, Eur. J. Immunol. 22: 1365-1372). Preferably, 1-2 mg of HSP-peptide complex is crosslinked in the presence of 0.002% glutaraldehyde for 2 hours. Glutaraldehyde is removed by dialysis against phosphate buffered saline (PBS) overnight (Lussow et al., 1991, Eur. J. Immunol. 21: 2297-2302). Alternatively, a HSP and peptides can be crosslinked by ultraviolet (UV) crosslinking under conditions known in the art.

Complexes of HSP and antigenic peptides from separate covalent and/or non-covalent complexing reactions can optionally be combined to form a composition before administration to a subject. In a specific embodiment, one HSP is complexed to 49 of the antigenic peptides of the invention. In various embodiments, each antigenic peptide in the plurality of antigenic peptides complexed to HSP does not contain herpesvirus amino acid sequences contiguous with that of each of the respective herpesvirus peptide. In various embodiments, the plurality of antigenic peptides complexed to HSP do not include antigenic peptides comprising epitope(s) of HSV2 proteins other than those comprising the amino acid sequence of SEQ ID NO: 1 to 49, respectively. In a specific embodiment, the plurality of complexes of heat shock proteins and antigenic peptides are not obtained or purified from a cell. In various embodiments, at least 10%, 20%, 30%, 40%, 50%, 60%, 70%, 80%, 90%, or 95% of the antigenic peptides in the complexes are the different herpesvirus peptides selected from the group consisting of SEQ ID NO: 1 to 102 or SEQ ID NO: 1 to 49.

In a preferred embodiment, hsp70 and/or hsc70 is complexed to the herpesvirus peptides having the amino acid sequences of SEQ ID NOS:1-49. In another preferred embodiment, the composition comprises 49 different complexes of a stress protein noncovalently bound to an antigenic peptide, wherein said 49 different complexes each comprise a different antigenic peptide, wherein each one of said different antigenic peptide comprises one or more HLA-binding epitope of one of each herpesvirus peptide consisting of an amino acid sequence selected from the group consisting of SEQ ID NO: 1 to 49. More preferably, the stress protein is human hsc70, and most preferably, the antigenic peptides complexed to hsc70 are the herpesvirus peptides SEQ ID NO: 1 to 49.

5.4. Uses

The present invention also provides methods of uses of the compositions of the invention. The pharmaceutical compositions comprising antigenic peptides, or antigenic peptides and adjuvants, can be used for treating and/or preventing infections by herpesviruses. The compositions can be used to make medicaments and vaccines for use by individuals or subjects in whom treatment or prevention of HSV infection is desired. In various embodiments, such individual or subject is an animal that can be infected by herpesviruses, preferably a mammal, a non-human primate, and most preferably human. The term "animal" as used herein includes but is not limited to companion animals, such as cats and dogs; zoo animals; wild animals, including deer, foxes and raccoons; farm animals, livestock and fowl, including horses, cattle, sheep, pigs, turkeys, ducks, and chickens, and laboratory animals, such as rodents, rabbits, and guinea pigs.

5.4.1. Treatment of Herpes Virus Infection

The pharmaceutical compositions of the invention can be used alone or in combination with other therapies for the treatment of acute or chronic (primary or recurrent) HSV infection.

Infection by HSV-1 and HSV-2 are associated in many individuals with frequent and/or painful recurrences that manifest themselves as eruptions of the skin or mucous membranes, specifically as oral/labial cold sores (in HSV-1 infection) or genital blisters (in HSV-2 infection). Live virus can be shed from these vesicles. Transmission is usually by contact. The virus may migrate to nerve cells where it remains in a resting latent state. Frequency and site of recurrence may vary. Reactivation of the viruses and recurrence of the infection and symptoms can be set off by a variety of factors including fever, sun exposure, menstrual period, immunosuppression, stress, or physical contact.

Initial infection with HSV-1 is characterized by oral sores that last approximately 10-14 days, often accompanied by fever, headache, and body aches. Initial infection with HSV-2 is characterized by multiple painful blisters and may be accompanied by fever and a general feeling of illness. Administration of the pharmaceutical compositions of the invention at the first signs of HSV infection would have the effects of decreasing the severity and/or length of the symptoms, for example decreasing the numbers of sores, decreasing the pain associated with the sores, decreasing fever and feelings of illness, and/or decreasing the length of time the herpetic sores are present from over a week to a few days or less.

The pharmaceutical compositions of the invention may be administered when a primary infection is detected, or prior to or during an episode of recurrent infection for the amelioration of symptoms. The goals of the therapeutic methods include but are not limited to reducing the severity of disease associated with primary infection; reducing the frequency of reactivation of latent virus; limiting the severity of reactivated disease; and restricting the transmission of virus associated with either primary or reactivated infection.

Recurrent HSV-1 infection is characterized by oral cold sores and redness and swelling of the area, lasting for about one week. Recurrent HSV-2 infection begins with symptoms of tingling, discomfort, itching, or aching of the genital area, followed several hours to several days later by the appearance of painful blisters that break open, leaving sores. A typical episode of genital herpes lasts for about one week. Administration of the pharmaceutical compositions of the invention at the first signs of recurrent HSV infection, preferably at the first signs of discomfort or swelling in the oral or genital area, would produce therapeutic benefits such as decreasing the severity and/or length of the symptoms, for example decreasing the numbers of sores, decreasing the pain associated with the sores, and/or decreasing the length of time the herpetic sores are present from a week to a few days or less. For example, administration of a pharmaceutical preparation of the peptides and adjuvants of the invention at the initial signs of herpes-related blister formation would have the effect of reducing or eliminating the formation and eruption of such blisters, thereby reducing or eliminating the discomfort associated with the disease and also reducing viral shedding.

Administration can begin at the first sign of viral infection or reactivation, followed by boosting doses until at least symptoms are substantially abated and for a period thereafter. Treatment of an infected individual with the compositions of the invention may hasten resolution of the infection. For those individuals susceptible (or predisposed) to frequent recurrent infection the compositions are particularly useful in methods for reducing the frequency of such recurrent infection. For example, the composition may be administered after such infected individuals have been exposed to factors that are known or suspected to set off a recurrent infection, such as sun exposure or fever.

The pharmaceutical compositions can also be administered to symptomless individuals who are nevertheless infected by HSV, and are carriers of HSV. Such individuals can be identified by the presence of anti-HSV antibodies in their circulation.

5.4.2. Prevention of Herpes Virus Infection

The pharmaceutical compositions of the invention can also be used for immunization against herpesviruses, particularly HSV-1 and HSV-2. Prophylactic administration of a pharmaceutical composition to an individual can confer protection against a future infection by HSV-1 or HSV-2. For example, if an immunized individual is exposed to the virus, the individual may not show any symptoms of HSV infection, and/or the viruses are inactivated before infecting large number of cells and replicating productively in the immunized individual.

The methods of preventing a primary infection by HSV can be applied to a population generally or to a selected subpopulation, for example, to prevent spreading of the virus within a population or to control an epidemic. The methods are particularly applicable to individuals who are immunosuppressed, immunocompromised or at elevated risk for acquiring HSV, such as healthcare providers, HIV-positive individuals or family members and partners of HSV-infected individuals.

5.4.3. Combination Therapy

Combination therapy refers to the use of pharmaceutical compositions of the invention with another modality to prevent or treat the infectious disease. The administration of the pharmaceutical compositions of the invention can augment the effect of anti-infectives, and vice versa. In one embodiment, this additional form of modality is a non-HSP modality, i.e., this modality does not comprise HSP as a component. This approach is commonly termed combination therapy, adjunctive therapy or conjunctive therapy (the terms are used interchangeably herein). With combination therapy, additive potency or additive therapeutic effect can be observed. Synergistic outcomes where the therapeutic efficacy is greater than additive can also be expected. The use of combination therapy can also provide better therapeutic profiles than the administration of the treatment modality, or the pharmaceutical compositions of the invention alone. The additive or synergistic effect may allow the dosage and/or dosing frequency of either or both modalities be adjusted to reduce or avoid unwanted or adverse effects.

In various specific embodiments, the combination therapy comprises the administration of pharmaceutical compositions of the invention to a subject treated with a treatment modality wherein the treatment modality administered alone is not clinically adequate to treat the subject such that the subject needs additional effective therapy, e.g., a subject is unresponsive to a treatment modality without administering the pharmaceutical compositions of the invention. Included in such embodiments are methods comprising administering the pharmaceutical compositions of the invention to a subject receiving a treatment modality wherein said subject has responded to therapy yet suffers from side effects, relapse, develops resistance, etc. Such a subject might be non-responsive or refractory to treatment with the treatment modality alone, i.e., at least some significant portion of pathogens are not inactivated, or the frequency and/or severity of recurrent infection remains unchanged. The embodiments provide that the methods of the invention comprising administration of the pharmaceutical compositions of the invention to a subject refractory to a treatment modality alone can improve the therapeutic effectiveness of the treatment modality when administered as contemplated by the methods of the invention. The determination of the effectiveness of a treatment modality can be assayed in vivo or in vitro using methods known in the art. In one embodiment, the pharmaceutical preparations of the invention are administered in combination with a second treatment modality comprising a different HSV vaccine. Such an HSV vaccine can be a subunit vaccine, a DNA vaccine, or a attenuated virus vaccine.

In one embodiment, an infectious disease is refractory or non-responsive where the number of lesions and/or pathogens has not been significantly reduced, or has increased.

In one embodiment, a lesser amount of the second treatment modality is required to produce a therapeutic benefit in a subject. In specific embodiments, a reduction of about 10%, 20%, 30%, 40% and 50% of the amount of second treatment modality can be achieved. The amount of second treatment modality to be used with the peptides and adjuvants, including amounts in a range that does not produce any observable therapeutic benefits, can be determined by dose-response experiments conducted in animal models by methods well known in the art.

In one preferred embodiment, the pharmaceutical composition is used in combination with a second treatment modality, such as a chemotherapeutic agent. Currently approved HSV treatments include the acyclic nucleoside analogs acyclovir, valacyclovir, pencyclovir, and famcyclovir, phosphonate analogs such as cidofovir, and pyrophosphate analogs such as foscarnet/phosphonoformic acid. These nucleoside analogs target the viral polymerase. Additional HSV therapies that may also be used include protease inhibitors such as N-acyl analogs of 5-methylthieno[2,3-d]oxazinone; helicase inhibitors such as the 2-amino thiazole compound T157602; ribonucleotide reductase inhibitors such as the compound BILD1633; uracil-DNA glycosylase inhibitors such as 6-(4-octylanilino)-uracil; thymidine kinase inhibitors such as 6-azapyrimidine-2'-deoxynucleosides or $N^2$-phenylguanine compounds including 9-(4-hydroxybutyl)-$N^2$-phenylguanine; and other viral polymerase inhibitors including enantiomeric nucleosides such as D-cyclohexenyl-G and L-cyclohexenyl-C (reviewed in Villareal E C, Progress in Drug Research 60:263-307, 2003). In a preferred embodiment, said second treatment modality is an antiviral drug such as acyclovir, valacyclovir, pencyclovir, famcyclovir, cidofovir, and phosphonoformic acid. Concurrent administration of antigenic peptides and adjuvants and a second treatment modality means that the peptides and adjuvants are given at reasonably the same time as the second treatment modality. This method provides that the two administrations are performed within a time frame of less than one minute to about five minutes, or up to about sixty minutes from each other, for example, at the same doctor's visit.

In another embodiment, the pharmaceutical compositions of the invention are used in combination with one or more antibodies, including but not limited to polyclonal antibodies, monoclonal antibodies, chimeric antibodies. antibody fragments, single chain antibodies, and the like. Preferably, the antibodies bind herpesvirus particles and/or their components.

In another embodiment, the pharmaceutical compositions of the invention are used in combination with one or more biological response modifiers. One group of biological response modifiers is the cytokines. In one such embodiment, a cytokine is administered to a subject receiving the pharmaceutical compositions of the invention. In another such embodiment, the pharmaceutical compositions of the invention are administered to a subject receiving a chemotherapeutic agent such as an antiviral agent, antibody, adjuvant, or biological response modifier, in combination with a cytokine. In various embodiments, one or more cytokine(s) can be used and are selected from the group consisting of IL-1α, IL-1β, IL-2, IL-3, IL-4, IL-5, IL-6, IL-7, IL-8, IL-9, IL-10, IL-11, IL-12, IFNα, IFNβ, IFNγ, TNFα, TNFβ, G-CSF, GM-CSF, TGF-β, IL-15, IL-18, GM-CSF, INF-γ, INF-α, SLC, endothelial monocyte activating protein-2 (EMAP2), MIP-3α, MIP-3β, or an MHC gene, such as HLA-B7. Additionally, other exemplary cytokines include other members of the TNF family, including but not limited to TNF-α-related apoptosis-inducing ligand (TRAIL), TNF-α-related activation-induced cytokine (TRANCE), TNF-α-related weak inducer of apoptosis (TWEAK), CD40 ligand (CD40L), lymphotoxin alpha (LT-α), lymphotoxin beta (LT-β), OX40 ligand (OX40L), Fas ligand (FasL), CD27 ligand (CD27L), CD30 ligand (CD30L), 41BB ligand (41BBL), APRIL, LIGHT, TL1, TNFSF16, TNFSF17, and AITR-L, or a functional portion thereof. See, e.g., Kwon et al., 1999, Curr. Opin. Immunol. 11:340-345 for a general review of the TNF family. Preferably, the pharmaceutical compositions of the invention are administered prior to the treatment modalities.

In other embodiments, pharmaceutical compositions of the invention are used in combination with one or more biological response modifiers which are agonists or antagonists of various ligands, receptors and signal transduction molecules of the immune system. For examples, the biological response modifiers include but are not limited to agonists of Toll-like receptors (TLR-2, TLR-7, TLR-8 and TLR-9); LPS; agonists of 41BB, OX40, ICOS, and CD40; and antagonists of Fas ligand, PD1, and CTLA-4. These agonists and antagonists can be antibodies, antibody fragments, peptides, peptidomimetic compounds, polysaccharides, and small molecules.

In a preferred embodiment, pharmaceutical compositions of the invention are used in combination with one or more additional adjuvants such as saponins and immunostimulatory nucleic acids. For example, the adjuvant in the pharmaceutical composition is a stress protein which is complexed with the antigenic peptides of the invention; the additional adjuvant used in combination can be a saponin, such as QS21, and the like, including but not limited to those disclosed in U.S. Pat. Nos. 5,057,540; 5,273,965; 5,443,829; 5,650,398; 6,231,859; and 6,524,584.

Many immunostimulatory nucleic acids are oligonucleotides comprising an unmethylated CpG motif, are mitogenic to vertebrate lymphocytes, and are known to enhance the immune response. See Woolridge, et al., 1997, Blood 89:2994-2998. Such oligonucleotides are described in International Patent Publication Nos. WO 01/22972, WO 01/51083, WO 98/40100 and WO 99/61056, each of which is incorporated herein in its entirety, as well as U.S. Pat. Nos. 6,207,646, 6,194,388, 6,218,371, 6,239,116, 6,429,199, and 6,406,705, each of which is incorporated herein in its entirety. Other kinds of immunostimulatory oligonucleotides such as phosphorothioate oligodeoxynucleotides containing YpG- and CpR-motifs have been described by Kandimalla et al. in "Effect of Chemical Modifications of Cytosine and Guanine in a CpG-Motif of Oligonucleotides: Structure-Immunostimulatory Activity Relationships." Bioorganic & Medicinal Chemistry 9:807-813 (2001), incorporated herein by reference in its entirety. Also encompassed are immunostimulatory oligonucleotides that lack CpG dinucleotides which when administered by mucosal routes (including low dose administration) or at high doses through parenteral routes, augment antibody responses, often as much as did the CpG nucleic acids, however the response was Th2-biased (IgG1>>IgG2a). See United States Patent Publication No. 20010044416 A1, which is incorporated herein by reference in its entirety. Methods of determining the activity of immunostimulatory oligonucleotides can be performed as described in the aforementioned patents and publications. Moreover, immunostimulatory oligonucleotides can be modified within the phosphate backbone, sugar, nucleobase and internucleotide linkages in order to modulate the activity. Such modifications are known to those of skill in the art.

In a preferred embodiment, the invention provides pharmaceutical compositions comprising, in a physiologically acceptable carrier, one or more of the antigenic peptides of this invention and an adjuvant such as at least one immunostimulatory oligonucleotide or a saponin (e.g., QS21). The pharmaceutical composition can comprise hsp70 complexed with one or more antigenic peptides of the invention, combined with QS21. In another embodiment, the pharmaceutical composition comprises hsp70 complexed with one or more antigenic peptides of the invention, combined with immunostimulatory oligonucleotides. In a most preferred embodiment, the pharmaceutical composition comprises hsp70 complexed with one or more antigenic peptides of the invention, combined with QS21 and immunostimulatory oligonucleotides.

5.4.4. Dosage

The dosage of antigenic peptides, and the dosage of any additional treatment modality such as an adjuvant if combination therapy is to be administered, depends to a large extent on the weight and general state of health of the subject being treated as well as the amount of vaccine composition administered, the frequency of treatment and the route of administration. Amounts effective for this use will also depend on the stage and severity of the disease and the judgment of the prescribing physician, but generally range for the initial immunization (that is, for therapeutic administration) from about 1.0 µg to about 5000 µg of antigenic peptide for a 70 kg patient, followed by boosting dosages of from about 1.0 µg to about 1000 µg of antigenic peptide pursuant to a boosting regimen over weeks to months depending upon the patient's response and condition by measuring specific CTL activity in the patient's blood. Regimens for continuing therapy, including site, dose and frequency may be guided by the initial response and clinical judgment. Dosage ranges and regimens for adjuvants are known to those in the art, see, e.g., Vogel and Powell, 1995, A Compendium of Vaccine Adjuvants and Excipients; M. F. Powell, M. J. Newman (eds.), Plenum Press, New York, pages 141-228.

Preferred adjuvants include QS21 and CpG oligonucleotides. Preferred dosage ranges for QS21 are 1 µg to 200 µg per administration. Most preferred dosages for QS21 are 10, 25, and 50 µg per administration.

In specific embodiments comprising HSPs complexed to antigenic peptides, depending on the route of administration and the type of HSPs in the pharmaceutical compositions of the invention, the amount of HSP in the HSP preparation can range, for example, from 0.1 to 1000 µg per administration. The amount of hsp70- and/or gp96 complexes administered is 0.1, 0.2, 0.5, 1, 2, 5, 10, 20, 30, 40, 50, 60, 70, 80, 90, 100, 200, 250, 300, 400, 500 or 600 micrograms. In one embodiment, the preferred amounts of gp96 or hsp70 are in the range of 10 to 600 µg per administration and 0.1 to 100 µg if the HSP preparation is administered intradermally. In another embodiment, an amount of hsp70- and/or gp96-antigenic peptide complexes is administered that is in the range of about 0.1 microgram to about 600 micrograms, and preferably about 1 micrograms to about 60 micrograms for a human patient. Preferably, the amount is less than 100 micrograms. Most preferably, the amount of hsp70- and/or gp96 complexes administered is 5 micrograms, 25 micrograms, or 50 micrograms. Preferably, the complexes of HSP and the antigenic peptides are purified.

The dosage for hsp-90 peptide complexes in a human patient provided by the present invention is in the range of about 5 to 5,000 micrograms. Preferably, the the amount of hsp90 complexes administered is 5, 10, 20, 25, 50, 60, 70, 80, 90, 100, 200, 250, 500, 1000, 2000, 2500, or 5000 microgram, the most preferred dosage being 100 microgram. For intradermal administration of hsp 90, the preferred amounts are about 5 to 50 µg per administration.

In one embodiment, for the therapeutic regimen of the present invention, a dosage substantially equivalent to that seen to be effective in smaller non-human animals (e.g., mice or guinea pigs) is effective for human administration, optionally subject to a correction factor not exceeding a fifty fold increase, based on the relative lymph node sizes in such mammals and in humans. Specifically, interspecies dose-response equivalence for stress proteins (or HSPs) noncovalently bound to or mixed with antigenic molecules for a human dose is estimated as the product of the therapeutic dosage observed in mice and a single scaling ratio, not exceeding a fifty fold increase.

In another embodiment, the present invention provides dosages of the complexes of antigenic peptides, optionally combined with adjuvants, that are much smaller than the dosages estimated by extrapolation. For example, according to the invention, an amount of Hsp70-antigenic peptide complexes and/or gp96-antigenic peptide complexes is administered that is, preferably, in the range of about 2 microgram to about 150 micrograms for a human patient, the preferred human dosage being the same as used in a 25 g mouse. The dosage for hsp-90 peptide complexes in a human patient provided by the present invention is, preferably, in the range of about 10 to 1,000 micrograms, the preferred dosage being 20 micrograms.

The doses recited above can be given once or repeatedly, such as daily, every other day, weekly, biweekly, or monthly, for a period up to a year or over a year. Doses are preferably given once weekly for a period of about 4-6 weeks, and the mode or site of administration is preferably varied with each administration. In a preferred example, subcutaneous administrations are given, with each site of administration varied sequentially. Thus, by way of example and not limitation, the first injection may be given subcutaneously on the left arm, the second on the right arm, the third on the left belly, the fourth on the right belly, the fifth on the left thigh, the sixth on the right thigh, etc. The same site may be repeated after a gap of one or more injections. Also, split injections may be given. Thus, for example, half the dose may be given in one site and the other half on an other site on the same day.

Alternatively, the mode of administration is sequentially varied, e.g., weekly injections are given in sequence subcutaneously, intradermally, intramuscularly, intravenously or intraperitoneally.

After 4-6 weeks, further injections are preferably given at two-week intervals over a period of time of one month. Later injections may be given monthly. The pace of later injections may be modified, depending upon the patient's clinical progress and responsiveness to the immunotherapy.

In one embodiment, the pharmaceutical composition is administered to a subject at reasonably the same time as an additional treatment modality or modalities. This method provides that the two administrations are performed within a time frame of less than one minute to about five minutes, or up to about sixty minutes from each other, for example, at the same doctor's visit.

In another embodiment, the complexes of antigenic peptides and adjuvants and an additional treatment modality or modalities are administered at exactly the same time. In yet another embodiment the complexes of antigenic peptides and adjuvants and an additional treatment modality or modalities are administered in a sequence and within a time interval such that the complexes of the invention and the additional treatment modality or modalities can act together to provide an increased benefit than if they were administered alone. In another embodiment, the complexes of the invention and an additional treatment modality or modalities are administered sufficiently close in time so as to provide the desired therapeutic or prophylactic outcome. Each can be administered simultaneously or separately, in any appropriate form and by any suitable route. In one embodiment, the complexes of the invention and the additional treatment modality or modalities are administered by different routes of administration. In an alternate embodiment, each is administered by the same route of administration. The complexes of the invention can be administered at the same or different sites, e.g. arm and leg. When administered simultaneously, the complexes of the invention and an additional treatment modality or modalities may or may not be administered in admixture or at the same site of administration by the same route of administration.

In various embodiments, the complexes of the invention and an additional treatment modality or modalities are administered less than 1 hour apart, at about 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In other embodiments, the complexes of the invention and vaccine composition are administered 2 to 4 days apart, 4 to 6 days apart, 1 week a part, 1 to 2 weeks apart, 2 to 4 weeks apart, one month apart, 1 to 2 months apart, or 2 or more months apart. In preferred embodiments, the complexes of the invention and an additional treatment modality or modalities are administered in a time frame where both are still active. One skilled in the art would be able to determine such a time frame by determining the half life of each administered component.

In one embodiment, the complexes of the invention and an additional treatment modality or modalities are administered within the same patient visit. In a specific preferred embodiment, the complexes of the invention is administered prior to the administration of an additional treatment modality or modalities. In an alternate specific embodiment, the complexes of the invention is administered subsequent to the administration of an additional treatment modality or modalities.

In certain embodiments, the complexes of the invention and an additional treatment modality or modalities are cyclically administered to a subject. Cycling therapy involves the administration of the complexes of the invention for a period of time, followed by the administration of a modality for a period of time and repeating this sequential administration. Cycling therapy can reduce the development of resistance to one or more of the therapies, avoid or reduce the side effects of one of the therapies, and/or improve the efficacy of the treatment. In such embodiments, the invention contemplates the alternating administration of a complexes of the invention followed by the administration of a modality 4 to 6 days later, preferable 2 to 4 days, later, more preferably 1 to 2 days later, wherein such a cycle may be repeated as many times as desired. In certain embodiments, the complexes of the invention and the modality are alternately administered in a cycle of less than 3 weeks, once every two weeks, once every 10 days or once every week. In a specific embodiment, complexes of the invention is administered to a subject within a time frame of one hour to twenty four hours after the administration of a modality. The time frame can be extended further to a few days or more if a slow- or continuous-release type of modality delivery system is used.

5.4.5. Routes of Administration

In an embodiment of the invention, antigenic peptides and adjuvants may be administered using any desired route of administration. Non-mucosal routes of administration include, but are not limited to, intradermal and topical administration. Mucosal routes of administration include, but are not limited to, oral, rectal and nasal administration. Advantages of intradermal administration include use of lower doses and rapid absorption, respectively. Advantages of subcutaneous or intramuscular administration include suitability for some insoluble suspensions and oily suspensions, respectively. Preparations for mucosal administrations are suitable in various formulations as described below.

Many methods may be used to introduce the pharmaceutical compositions described above, these include but are not limited to oral, intradermal, intramuscular, intraperitoneal, intravenous, subcutaneous, and intranasal routes.

Solubility and the site of the administration are factors which should be considered when choosing the route of administration of the antigenic peptides and adjuvants of the invention. The mode of administration can be varied, including, but not limited to, e.g., subcutaneously, intravenously, intraperitoneally, intramuscularly, intradermally or mucosally. Mucosal routes can further take the form of oral, rectal and nasal administration.

If the antigenic peptides and adjuvants are water-soluble, then it may be formulated in an appropriate buffer, for example, phosphate buffered saline or other physiologically compatible solutions, preferably sterile. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, or rectal administration.

For oral administration, the pharmaceutical preparation may be in liquid form, for example, solutions, syrups or suspensions, or may be presented as a drug product for reconstitution with water or other suitable vehicle before use. Such a liquid preparation may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical preparation may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

The antigenic peptides and adjuvants for oral administration may be suitably formulated to be released in a controlled and/or timed manner.

For buccal administration, the preparation of antigenic peptides and adjuvants may take the form of tablets or lozenges formulated in conventional manner.

The preparation may be formulated for parenteral administration by injection, e.g., by bolus injection or continuous infusion. Formulations for injection may be presented in unit dosage form, e.g., in ampoules or in multi-dose containers, with an added preservative. The preparation may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The preparation may also be formulated in a rectal preparation such as a suppository or retention enema, e.g., containing conventional suppository bases such as cocoa butter or other glycerides.

In addition to the formulations described previously, the preparation may also be formulated as a depot preparation. Such long acting formulations may be administered by implantation (for example, subcutaneously or intramuscularly) or by intramuscular injection. Thus, for example, the preparation may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

For administration by inhalation, the preparation for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

5.4.6. Kits

Kits are also provided for carrying out the prophylactic and therapeutic methods of the present invention. The kits may optionally be accompanied by instructions on how to use the various components of the kits.

In a specific embodiment, a kit comprises a first container containing antigenic peptides of the invention; and a second container containing an adjuvant or adjuvants that, when administered before, concurrently with, or after the administration of the peptides in the first container, is effective to induce an immune response against the antigenic peptides. In another embodiment, a kit comprises a first container containing antigenic peptides of the invention; a second container containing an adjuvant or adjuvants; and a third container containing a second treatment modality, such as an antiviral agent for oral or topical administration. In yet another embodiment, the kit comprises a container containing both the antigenic peptides and adjuvants in one container, and a second container containing a second treatment modality, such as an antiviral agent for oral or topical administration; or an additional adjuvant, such as a saponin, including but not limited to QS21. Additional containers may be present for additional treatment modalities that can be used in combination. Preferably, the antigenic peptides and adjuvants in the container are in the form of complexes, such as HSP-antigenic peptide complexes. More preferably, the antigenic peptides and adjuvants in the container are present in pre-determined amounts effective to treat or prevent HSV infection or an episode of recurrent infection. If desired, the pharmaceutical compositions can be presented in a pack or dispenser device which may contain one or more unit dosage forms containing the complexes. The pack may for example comprise metal or plastic foil, such as a blister pack. The pack or dispenser device may be accompanied by instructions for administration.

5.4.7. Monitoring of Specific Immune Response in Animal Models

The broad host range of HSV has allowed the use of a number of animal models for the study of viral latency. Such animal models can be used for studies of the efficacy of the pharmaceutical compositions of the invention, or to test, formulate, or determine dosages for various stages of disease progression. Murine models of HSV infection have been explored extensively and have yielded a wide array of insights into the mechanisms of antiviral immunity. See Mester J C, Rouse B T, "The mouse model and understanding immunity to herpes simplex virus.", Rev Infect Dis. 1991 November-December; 13 Suppl 11:S935-45. Rev Infect Dis. 1984 January-February; 6(1):33-50. The guinea pig has also been used a model. See Hsiung G D, Mayo D R, Lucia H L, Landry M L. "Genital herpes: pathogenesis and chemotherapy in the guinea pig model." Rev Infect Dis. 1984 January-February; 6(1):33-50. Any such model can be used to study and titrate the pharmaceutical compositions of the invention.

Recurrent lesions from herpes simplex virus (HSV) occur after reactivation of latent HSV in neurons of sensory ganglion, axonal transport of reactivated virus, and HSV replication on the skin. Three animal systems—the rabbit, the guinea pig, and the mouse—have provided the means for generating the vast majority of data now available concerning HSV latency and reactivation.

Infection of rabbit eyes leads to a latent infection in which virus can be recovered from the trigeminal nerve ganglia only following explant and co-cultivation with indicator cells. In addition, virus can be sporadically recovered from the eye following periods of latency. Of particular use is the fact that the reactivation can be efficiently induced by the iontophoresis of epinephrine into the eye—a procedure described in Hill and colleague at the LSU Eye Center. This model has been very important in establishing the requirement for LAT (the latency associated transcript) expression for efficient reactivation.

Vaginal inoculation of female guinea pigs with HSV-1 or HSV-2 results in obvious primary infection with some mortality. Following recovery, survivors of primary infection periodically display vesicular recrudescence in the vaginal area from which infectious virus and/or viral DNA can be recovered. This model, developed by L. Stanberry at the University of Cincinnati Medical School (see Rev. Infect. Dis. 1991, 13 Suppl. 11:S920-3 for review), can be used for testing the pharmaceutical compositions of the invention.

There are several HSV mouse models, including: 1) the foot-pad/dorsal root ganglia model; and 2) the mouse eye/trigeminal ganglia model. Direct demonstration of the ability of HSV to establish and maintain a latent infection in neuronal cells was accomplished at the University of California, Los Angeles (Javier R T et al., Science 1986, 234:746-8) using mouse foot-pad infection which is followed by latent infection of spinal ganglia. This model system is roughly analogous to genital infection of HSV in humans, and has been central to describing many of the parameters of HSV latent infection including the identification of the neuron as the site of latent infection, axonal transport of virus through the sciatic nerve, ability of non-replicating virus to establish latent infections, and the characterization of restricted transcription of the latency specific transcription unit during the latent phase of infection. Following infection of the foot-pad, local pathology is observed with clear evidence of involvement of the central nervous system (CNS), the mice that recover are evidently physiologically normal. When dorsal root ganglia are dissected and cultured (either whole or following disruption) on feeder cells, HSV-induced cytopathology can be detected within 4-12 days. This explant recovery of HSV from such latently infected spinal ganglia has been an extremely useful and relatively inexpensive means of assaying the presence of viral genomes within the tissue in question. A second murine model for HSV-1 and HSV-2 latency involves the infection of the cornea which is followed by virus latency in the trigeminal ganglia. As in the foot pad model, latent HSV genomes express LAT in a portion of those neurons maintaining them, and virus can be recovered by co-cultivation of explanted ganglia.

6. EXAMPLES

6.1. Synthesis of Antigenic Peptides

A number of antigenic peptides of the invention were synthesized by chemical synthesis as described in Section 5.1.1. As seen in Table 2, peptides having amino acid sequences of SEQ ID NOS: 1-49 were successfully synthesized using this method. Peptides synthesized and purified to a purity of greater than 85% by HPLC, and further having peptide identity confirmed by mass spectrometry, were considered to "Pass" these purity and confirmation requirements for synthesis, as indicated in the column heading "Chemical Synthesis". Table 2 also lists the solubility of these antigenic peptides in water or Dimethyl Sulfoxide (DMSO). Some of the 102 herpesvirus peptides apparently cannot be synthesized efficiently by the method used to yield practical amounts of materials for testing. However, such antigenic peptides of the invention can still be synthesized by recombinant DNA technology using the methods described in Section 5.1.2., or by another different chemical manufacturing method known in the art.

A turbidity assay was used to assess the solubility of the peptides. Turbidity assays used either a Varian Cary double-beam spectrophotometer, or a Molecular Devices Spectromax absorbance plate reader (for high throughput experiments). The spectrophotometer assay read every 2 nm between 340 nm and 360 nm, and averaged the values. Samples were analyzed in duplicate using a quartz microcuvette that holds about 200 uL. The plate reader assay used a 96-well plate format that read every 4 nm between 340 nm and 360 nm and averaged those values. Samples in this assay were run in triplicate.

Prior to administration of the pharmaceutical compositions to animals, water soluble peptides were stored at 2 mg/mL, while DMSO soluble peptides were stored at 10 mg/mL.

Table 2. Solubility and Synthesis of Antigenic Peptides

| SEQ ID NO: | Name of Viral Peptide | Chemical Synthesis | Solubility |
|---|---|---|---|
| 1 | RL02-1 | Pass | water |
| 2 | RL02-2 | Pass | DMSO |
| 3 | RS01-2 | Pass | water |
| 4 | UL01-1 | Pass | water |
| 5 | UL01-3 | Pass | water |
| 6 | UL10-5 | Pass | water |
| 7 | UL13-2 | Pass | water |
| 8 | UL14-1 | Pass | water |
| 9 | UL14-2 | Pass | water |
| 10 | UL16-2 | Pass | water |
| 11 | UL17-2 | Pass | water |
| 12 | UL20-1 | Pass | water |
| 13 | UL20-2 | Pass | DMSO |
| 14 | UL22-1 | Pass | water |
| 15 | UL22-3 | Pass | DMSO |
| 16 | UL22-4 | Pass | water |
| 17 | UL27-2 | Pass | water |
| 18 | UL27-3 | Pass | water |
| 19 | UL33-1 | Pass | water |
| 20 | UL33-2 | Pass | water |
| 21 | UL34-1 | Pass | DMSO |
| 22 | UL36-3 | Pass | water |
| 23 | UL36-4 | Pass | DMSO |
| 24 | UL37-1 | Pass | DMSO |
| 25 | UL40-2 | Pass | water |
| 26 | UL40-3 | Pass | water |
| 27 | UL41-1 | Pass | water |
| 28 | UL41-2 | Pass | water |
| 29 | UL41-3 | Pass | DMSO |
| 30 | UL44-1 | Pass | water |
| 31 | UL44-4 | Pass | water |
| 32 | UL45-1 | Pass | water |
| 33 | UL46-1 | Pass | water |
| 34 | UL46-2 | Pass | DMSO |
| 35 | UL49-1 | Pass | water |
| 36 | UL49-2 | Pass | water |
| 37 | UL53-1 | Pass | DMSO |
| 38 | UL53-2 | Pass | DMSO |
| 39 | UL53-3 | Pass | water |
| 40 | UL54-1 | Pass | water |
| 41 | UL54-2 | Pass | water |
| 42 | US05-2 | Pass | water |
| 43 | US06-1 | Pass | DMSO |
| 44 | US06-3 | Pass | water |

-continued

| SEQ ID NO: | Name of Viral Peptide | Chemical Synthesis | Solubility |
|---|---|---|---|
| 45 | US09-2 | Pass | water |
| 46 | US10-1 | Pass | water |
| 47 | US10-2 | Pass | water |
| 48 | US11-1 | Pass | water |
| 49 | US11-2 | Pass | water |

6.2. Preparation of HSP-Antigenic Complexes

Human hsc70 was prepared using the methods of recombinant DNA technology. Briefly, the nucleic acid molecules encoding human hsc70 protein (Genbank Accession Y00371) were obtained and subcloned by recombinant DNA methodologies into a suitable bacterial expression vector. The pET-24a(+) expression vector (Novagen) containing the human Hsc70 cDNA (obtained from ATCC, catalog #771252) was transformed into competent E. coli BL21(DE3) strain cells for recombinant protein expression. Mouse HSP-70 was purified by ATP Agarose affinity chromatography. The purification process comprised the following steps: (a) homogenization of mouse tissue in Hepes/MgCl$_2$ buffer; (b) clarification of the homogenate by centrifugation followed by filtration of the supernatant; (c) conditioning of the filtrate with NaCl solution; (d) ATP-affinity chromatography; (e) buffer exchange/de-salting of the ATP-affinity column eluate using dia-filtration procedure; and (f) DEAE-Ion exchange chromatography and elution of the bound HSP-70 with sodium phosphate/NaCl, pH 7.2 buffer). These hsc70 and hsp70 preparations were then complexed to the antigenic peptides of the invention as follows.

Fourteen μM of mouse tissue-derived hsp70 (mHSP70) was incubated in a buffer containing 20 mM, sodium phosphate pH 7.4 and 150 mM sodium chloride with 14 μM of the 49 HSV-2 peptide pool (~0.29 μM of each individual peptide) to provide a final HSP:peptide ratio of 1:1 at 37° C. for 30 minutes. The HSP-peptide complex was subsequently mixed with 10 μg QS21 using a stock solution of 10 mg/mL QS21 in PBS.

6.3. Determination of Immunogenicity and Efficacy of HSP-Peptide Complexes in Vitro C57BL/6 mice were immunized intradermally on Days 0 and 7 with 100 μg per dose of pharmaceutical preparation containing (i) complexes of mHSP70 and the 49 HSV-2 peptides (at 1:1 mHSP70:49 peptides molar ratio), (ii) 5.5 μg of a pool of the 49 peptides alone (equivalent to that in the complex preparation), or (iii) 100 μg of mHSP70 alone, without (FIG. 1A) or with (FIG. 1B) 10 μg per dose of QS-21. On Day 14, the mice were euthanized, and their splenocytes were subjected to IFN-γ ELISPOT analysis (Fujihashi et al., J. Immunol. Methods 160:181-189, 1993). Shown in FIGS. 1A and 1B are numbers of IFN-γ secreting cells (SFCs) per 1×10$^6$ bulk splenocytes (pooled from 3 mice) after in vitro restimulation with (i) 10 μg/ml of the pool of 49 peptides, (ii) 10 μg/ml of OVA peptide (an irrelevant antigen), or (iii) culture medium only (no antigen) for 40 hours. Quantification of spots were conducted by ZellNet Consulting, Inc. (555 North Avenue, Suite 25S, Fort Lee, N.J. 07024).

As seen in FIG. 1A, splenocytes derived from mice treated with the pharmaceutical composition comprising complexes of hsp70 and the 49 peptides produced approximately 140 SFCs per 10$^6$ splenocytes. Splenocytes derived from mice treated with hsp70 without the 49 peptides produced fewer than 5 SFCs per 10$^6$ splenocytes. Splenocytes derived from mice treated with the 49 peptides without hsp70 produced less than 60 SFCs per 10$^6$ splenocytes. The results demonstrated that the complexes of hsp70 and HSV-2 peptides are more immunogenic than hsp70 or the peptides alone. The addition of adjuvant increased this immune response, as seen in FIG. 1B. Splenocytes derived from mice treated with a pharmaceutical composition comprising the complexes of hsp70 plus the 49 peptides plus QS21 adjuvant produced approximately 450 SFCs per 10$^6$ splenocytes. Splenocytes derived from mice treated with hsp70 without the 49 peptides produced fewer than 5 SFCs per 10$^6$ splenocytes. Splenocytes derived from mice treated with the 49 peptides without hsp70 produced over 250 SFCs per 10$^6$ splenocytes. The results demonstrated that complexes of hsp70 and the herpesvirus peptides of the invention are highly immunogenic in combination with a second adjuvant.

For further immunogenicity (ELISPOT) studies, the pharmaceutical composition was injected intradermally in 100 μl volume such that each mouse (strain C57BL/6) received 100 μg hsp70 and 5.5 μg total peptide pool. The vaccination was repeated 1 week later. Control groups were immunized with (i) peptides alone plus QS21 or (ii) hsp70 alone plus QS21. One week after the last vaccination, mice were sacrificed and spleens were harvested. 1×10$^6$ splenocytes were then distributed in each well of a 96 well plate pre-coated with anti-IFN-γ antibody. To stimulate the lymphocytes, 10 μg of the 49 peptide pool was added to the wells and the plates were incubated for 40 hours at 37° C., 5% CO$_2$. Following the incubation, cells were washed off the plates. The plates were then incubated with secondary biotin-conjugated anti-IFN-γ antibodies and subsequently with Strepavidin-conjugated horseradish peroxidase. The plates were finally developed with AEC (3-amino-9-ethyl-carbazole) as substrate. The cytokine spots were then analyzed using a Zellnet ELISPOT reader. The number of spots in each well, representing cytokine-secreting cells on a single cell basis, was enumerated and plotted. Splenocytes derived from mice treated with a pharmaceutical composition comprising the complexes of hsp70 plus the 49 peptides produced over 300 SFCs per 10$^6$ splenocytes. Splenocytes derived from mice treated with hsp70 without the 49 peptides produced fewer than 20 SFCs per 10$^6$ splenocytes. Splenocytes derived from mice treated with the 49 peptides without hsp70 produced approximately 80 SFCs per 10$^6$ splenocytes. These results provided additional support for the finding that complexes of hsp70 and herpesvirus peptides of the invention are highly immunogenic.

The herpesvirus antigen-specific response was long-lasting (FIG. 2). Splenocytes from mice immunized on day 0 and day 14 with a pharmaceutical composition comprising complexes of 49 peptides and hsp70 plus an adjuvant were harvested on days 28 and 84. These splenocytes produced nearly 500 SFCs per 10$^6$ splenocytes when harvested at day 28, and nearly 500 SFCs per 10$^6$ splenocytes when harvested at day 84. In contrast, splenocytes from mice immunized with hsp70 plus adjuvant alone produced fewer than 100 SFCs per 10$^6$ splenocytes. This data demonstrated that complexes of herpesvirus peptides and stress proteins provide an immune memory response, indicating that vaccines such as the pharmaceutical composition provided herein can provide long term immunization against infection by herpesvirus.

6.4. Determination of Immunogenicity and Efficacy of HSP-Peptide Complexes In Vivo Studies were carried out in female mice to determine whether hsp70-herpesvirus peptide complexes in QS-21 adjuvant formulation provided protection from HSV challenge in vivo.

For these evaluations of the pharmaceutical compositions, female Swiss Webster mice were immunized intradermally on Days 0, 7 and 14 with the following formulations (FIG. 3A,B,C, or D):

1. GP/CFA, total glycoprotein from HSV-2 infected cell lysates formulated in Freund's adjuvant (Freund's complete adjuvant for the 1st immunization, thereafter Freund's incomplete adjuvant was used) as an immunization positive control;
2. Saline/CFA, Freund's adjuvant formulated with placebo, immunization negative control;
3. mHSP70, 100 µg per dose of mHSP70;
4. QS-21, 10 µg per dose of QS-21;
5. 49 HSV-2 peptides/QS-21, 5.5 µg of 49 HSV-2 peptides (equivalent to the amount in the complex preparations)+10 µg per dose of QS-21; OR
6. mHSP70/49 HSV-2 peptides/QS-21, 100 µg per dose of mHSP70 complexed to 49 HSV-2 peptides (at 1:1 mHSP70 to total peptide molar ratio)+10 µg per dose of QS-21.

Mice were treated with depo-provera to synchronize their estrus cycles, and on day 28 were challenged intravaginally with $5 \times 10^5$ pfu of HSV-2 (strain 186). HSV-2 induced disease and mortality were evaluated up to day 49 following vaccination.

FIG. 3A shows survival curves (Kaplan and Meier, *J Am Stat Assoc.* 50, 457-481, 1958) for GP/CFA ("Glycoproteins/CFA Control"), Saline/CFA ("Mock/CFA Control"), and QS-21 ("Adjuvant") control groups. FIG. 3B shows survival curves (Kaplan and Meier, *J Am Stat Assoc.* 50, 457-481, 1958) for mHSP70, 49 HSV-2 peptides/QS-21 ("49 peptides+adjuvant"), and mHSP70/49 HSV-2 peptides/QS-21 ("mHSP/49 Peptides+adjuvant") groups. The arrow in FIG. 3B indicates that the mHSP/49 Peptides+adjuvant curve shows a significant difference (P<0.05) by Log-Rank analysis, compared to Saline/CFA (negative control) group. Thus, mice immunized with mHSP70/49 (at 1:1 mHSP70 to total peptide molar ratio)+10 µg per dose of QS-21 have significantly improved survival following viral challenge compared to Saline/CFA negative control. Similar results were also obtained for inbred BALB/c mice.

FIG. 3C shows hair loss and erythema (skin redness) development in GP/CFA ("Glycoproteins/CFA Control"), Saline/CFA ("Mock/CFA Control"), and QS-21 ("Adjuvant") control groups. FIG. 3D shows hair loss and erythema (skin redness) development in (i) mHSP70, (ii) 49 HSV-2 peptides/QS-21 ("49 peptides+adjuvant"), and (iii) mHSP70/49 HSV-2 peptides/QS-21 ("mHSP/49 Peptides+adjuvant") groups. The arrow in FIG. 3D indicates that the mHSP/49 Peptides+adjuvant curve shows a significant difference (P<0.05) by Log-Rank analysis, compared to Saline/CFA group. Thus, mice immunized with mHSP70/49 HSV-2 peptides (at 1:1 mHSP70 to total peptide molar ratio)+10 µg per dose of QS-21 have significantly reduced hair loss and erythema following viral challenge compared to the Saline/CFA negative control.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

---

What is claimed is:

1. A composition comprising at least ten different purified complexes of a stress protein noncovalently bound to an antigenic peptide, wherein said complexes each comprise a different antigenic peptide, and wherein each one of said different antigenic peptides comprises one or more HLA-binding epitopes of a different herpesvirus peptide selected from among herpesvirus peptides differing in amino acid sequence, wherein for ten of said complexes the amino acid sequence of each herpesvirus peptide is selected from the group consisting of SEQ ID NO: 3, 9, 21, 34, 35, 36, 37, 41, 42, and 44, wherein each one of said different antigenic peptides does not comprise the entire amino acid sequence of a herpes simplex virus protein.

2. The composition of claim 1, wherein the stress protein is a member of the hsp60, hsp70, or hsp90 family of stress proteins.

3. The composition of claim 1, wherein the stress protein is hsc70, Hsp70, hsp90, hsp110, grp170, gp96, calreticulin, or combinations of two or more thereof.

4. The composition of claim 1, wherein the stress protein is a human stress protein.

5. The composition of claim 1 which further comprises one or more adjuvants.

6. The composition of claim 5, wherein the adjuvant is a saponin or an immunostimulatory nucleic acid.

7. A kit comprising a first container comprising the composition of claim 1, and at least one container comprising an adjuvant, a chemotherapeutic agent, an antibody, or a biological response modifier.

8. A method of eliciting an immune response against HSV-1 or HSV-2 in an individual, the method comprising administering to the individual an immunogenic amount of the composition of claim 1.

9. The method of claim 8, further comprising administering to the individual an adjuvant, an antibody, a biological response modifier, or a chemotherapeutic agent.

10. The method of claim 9, wherein said chemotherapeutic agent is chosen from the group consisting of acyclovir, valacyclovir, pencyclovir, famcyclovir, cidofovir, and phosphonoformic acid, and combinations thereof.

11. The method of claim 9, wherein said biological response modifier is IL-1α, IL-1β, IL-2, IL-3, IL-4, IL-5, IL-6, IL-7, IL-8, IL-9, IL-10, IL-11, IL-12, IFNα, IFN-β, IFN-γ, TNFα, TNF β, G-CSF, GM-CSF, or TGF β.

12. The method of claim 8, wherein the individual is a human.

13. The composition of claim 1, wherein said different purified complexes are not obtained or purified from a cell.

14. The composition of claim 1, wherein said different antigenic peptides do not include antigenic peptides comprising epitope(s) of HSV2 proteins other than those comprising the amino acid sequence of SEQ ID NO: 3, 9, 21, 34, 35, 36, 37, 41, 42, and 44, respectively.

15. The composition of claim 1, wherein at least 50% of said at least ten plurality of different complexes comprise a herpesvirus peptide having an amino acid sequence selected from the group consisting of SEQ ID NO: 3, 9, 21, 34, 35, 36, 37, 41, 42, and 44.

16. The composition of claim 1, wherein each of said different antigenic peptides do not comprise amino acid sequences that are adjacent to the amino acid sequence of each of the respective herpesvirus peptides.

17. The composition of claim 3, wherein the stress protein is hsp70 or hsc70.

18. The composition of claim 17, further comprising at least one other purified complex of a stress protein noncovalently bound to an antigenic peptide, wherein the antigenic peptide of the at least one other purified complex comprises one or more HLA-binding epitopes of a herpesvirus peptide having an amino acid sequence selected from the group consisting of SEQ ID NO: 4-8, 16-18, 20, 23-25, 29, 33, 38, 39, 43, and 45-49.

19. The composition of claim 18, further comprising QS-21.

20. The composition of claim 19, wherein the amount of the stress protein in the composition is in a range of 10 μg to 600 μg.

21. The composition of claim 20, wherein the amount of the QS-21 in the composition is 10 μg, 25 μg, or 50 μg.

22. The composition of claim 1 further comprising at least one other purified complex of a stress protein noncovalently bound to an antigenic peptide, wherein the antigenic peptide of the at least one other purified complex comprises one or more HLA-binding epitopes of a herpesvirus peptide having an amino acid sequence selected from the group consisting of SEQ ID NO: 4-8, 16-18, 20, 23-25, 29, 33, 38, 39, 43, and 45-49.

23. The composition of claim 1 further comprising at least one other purified complex of a stress protein noncovalently bound to an antigenic peptide, wherein the antigenic peptide of the at least one other purified complex comprises one or more HLA-binding epitopes of a herpesvirus peptide having an amino acid sequence selected from the group consisting of SEQ ID NO: 1-2, 4-8, 10-20, 22-33, 38-40, 43, and 45-49.

24. The composition of claim 2 further comprising at least one other purified complex of a stress protein noncovalently bound to an antigenic peptide, wherein the antigenic peptide of the at least one other purified complex comprises one or more HLA-binding epitopes of a herpesvirus peptide having an amino acid sequence selected from the group consisting of SEQ ID NO: 1-2, 4-8, 10-20, 22-33, 38-40, 43, and 45-102.

25. The method of claim 8, wherein the composition is administered to the individual biweekly.

26. The method of claim 8, wherein the composition is administered to the individual by intradermal, subcutaneous, or mucosal administration.

27. The method of claim 8, wherein the stress protein is a member of the hsp60, hsp70, or hsp90 family of stress proteins.

28. The method of claim 27, wherein the stress protein is hsp70 or hsc70.

29. The method of claim 28, wherein the composition further comprises at least one other purified complex of a stress protein noncovalently bound to an antigenic peptide, wherein the antigenic peptide of the at least one other purified complex comprises one or more HLA-binding epitopes of a herpesvirus peptide having an amino acid sequence selected from the group consisting of SEQ ID NO: 4-8, 16-18, 20, 23-25, 29, 33, 38, 39, 43, and 45-49.

30. The method of claim 29, wherein the composition further comprises QS-21.

31. The method of claim 30, wherein the amount of the stress protein in the composition is in a range of 10 µg to 600 µg.

32. The method of claim 31, wherein the amount of the QS-21 in the composition is 10 µg, 25 µg, or 50 µg.

33. The method of claim 21, wherein the composition further comprises at least one other purified complex of a stress protein noncovalently bound to an antigenic peptide, wherein the antigenic peptide of the at least one other purified complex comprises one or more HLA-binding epitopes of a herpesvirus peptide having an amino acid sequence selected from the group consisting of SEQ ID NO: 4-8, 16-18, 20, 23-25, 29, 33, 38, 39, 43, and 45-49.

34. The method of claim 8, wherein, prior to administering the immunogenic amount of the composition of claim 1, antibodies against an HSV antigen are detectable in serum from the individual.

35. The method of claim 8, wherein, prior to administering the immunogenic amount of the composition of claim 1, antibodies against an HSV antigen are not detectable in serum from the individual.

36. A composition, comprising a plurality of different purified complexes of a stress protein noncovalently bound to an antigenic peptide, wherein said plurality of different complexes each comprise a different antigenic peptide, and wherein each one of said different antigenic peptides comprises one or more HLA-binding epitopes of a different herpesvirus peptide selected from among herpesvirus peptides differing in amino acid sequence, the amino acid sequence of each herpesvirus peptide selected from the group consisting of SEQ ID NO: 3, 9, 21, 34, 35, 36, 37, 41, 42, and 44, wherein each one of said different antigenic peptides is in a range of 8 amino acids to 45 amino acids in length.

37. The composition of claim 36, wherein each one of said different antigenic peptides is in a range of 30 amino acids to 40 amino acids in length.

38. The composition of claim 1, wherein the composition comprises at least 20 different purified complexes of a stress protein noncovalently bound to an antigenic peptide.

39. The composition of claim 1, wherein the composition comprises at least 30 different purified complexes of a stress protein noncovalently bound to an antigenic peptide.

40. The composition of claim 15, wherein each of said at least ten different complexes comprise a herpesvirus peptide having an amino acid sequence selected from the group consisting of SEQ ID NO: 3, 9, 21, 34, 35, 36, 37, 41, 42, and 44.

41. The composition of claim 36, further comprising at least one other purified complex of a stress protein noncovalently bound to an antigenic peptide, wherein the antigenic peptide of the at least one other purified complex comprises one or more HLA-binding epitopes of a herpesvirus peptide having an amino acid sequence selected from the group consisting of SEQ ID NO: 4-8, 16-18, 20, 23-25, 29, 33, 38, 39, 43, and 45-49.

42. The composition of claim 41, wherein the antigenic peptide in the at least one other purified complex is in a range of 8 amino acids to 45 amino acids in length.

43. The composition of claim 41, wherein the antigenic peptide in the at least one other purified complex is in a range of 30 amino acids to 40 amino acids in length.

* * * * *

UNITED STATES PATENT AND TRADEMARK OFFICE
CERTIFICATE OF CORRECTION

PATENT NO. : 8,541,002 B2
APPLICATION NO. : 10/571716
DATED : September 24, 2013
INVENTOR(S) : Alemseged Truneh et al.

It is certified that error appears in the above-identified patent and that said Letters Patent is hereby corrected as shown below:

On the Title Page, Item [75]:

Inventor "Xiaoyan Mo" should read --Annie Xiaoyan Mo--

In the Claims:

Column 102, Claim 15, line 37, "said at least ten plurality of different complexes comprise a" should read --said at least ten different complexes comprise a--

Column 103, Claim 24, line 11, "The composition of claim 2 further comprising at least" should read --The composition of claim 1 further comprising at least--

Column 103, Claim 33, line 43, "The method of claim 21, wherein the composition" should read --The method of claim 8, wherein the composition--

Signed and Sealed this
Seventh Day of January, 2014

Margaret A. Focarino
*Commissioner for Patents of the United States Patent and Trademark Office*

UNITED STATES PATENT AND TRADEMARK OFFICE
CERTIFICATE OF CORRECTION

PATENT NO.        : 8,541,002 B2
APPLICATION NO.   : 10/571716
DATED             : September 24, 2013
INVENTOR(S)       : Alemseged Truneh et al.

It is certified that error appears in the above-identified patent and that said Letters Patent is hereby corrected as shown below:

On the title page:

Item (75) Inventors: "Chuanliang Liu" should be changed to --Aston Chuanliang Liu--

Signed and Sealed this
Twenty-ninth Day of September, 2015

Michelle K. Lee
*Director of the United States Patent and Trademark Office*